United States Patent
Chen et al.

(10) Patent No.: US 11,667,650 B2
(45) Date of Patent: * Jun. 6, 2023

(54) THIENO-INDENO-MONOMERS AND POLYMERS

(71) Applicants: CLAP Co., Ltd., Seoul (KR); King Abdullah University of Science and Technology, Thuwal (SA)

(72) Inventors: Hu Chen, Thuwal (SA); Weimin Zhang, Thuwal (SA); Michael Hurhangee, London (GB); Iain McCulloch, Eastleigh (GB); Pascal Hayoz, Basel (CH); Daniel Kaelblein, Ludwigshafen (DE)

(73) Assignees: CLAP CO., LTD., Seoul (KR); KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/508,164

(22) Filed: Oct. 22, 2021

(65) Prior Publication Data

US 2022/0041617 A1     Feb. 10, 2022

Related U.S. Application Data

(63) Continuation of application No. 16/462,437, filed as application No. PCT/EP2017/081633 on Dec. 6, 2017, now Pat. No. 11,225,489.

(30) Foreign Application Priority Data

Dec. 6, 2016   (EP) .................................... 16202363
Dec. 29, 2016  (EP) .................................... 16207319

(51) Int. Cl.
  *C07D 495/04*   (2006.01)
  *C08G 61/12*    (2006.01)
  (Continued)

(52) U.S. Cl.
  CPC ......... *C07D 495/04* (2013.01); *C08G 61/126* (2013.01); *H10K 85/113* (2023.02);
  (Continued)

(58) Field of Classification Search
  CPC ...... C08G 2261/3223; C08G 2261/126; C08G 2261/124; C08G 2261/95; C08G 2261/91;
  (Continued)

(56) References Cited

U.S. PATENT DOCUMENTS

2005/0082525 A1   4/2005   Heeney
2013/0320316 A1   12/2013  Park
2015/0144847 A1   5/2015   D'Lavari et al.

FOREIGN PATENT DOCUMENTS

CN          105061463 A        11/2015
WO     WO 2013/159862 A1      10/2013
WO     WO 2018/065350 A1       4/2018

OTHER PUBLICATIONS

International Search Report dated Jun. 28, 2018 in PCT/EP2017/081633 filed on Dec. 6, 2017.

(Continued)

*Primary Examiner* — Shane Fang

(74) *Attorney, Agent, or Firm* — Norton Rose Fulbright US LLP

(57) ABSTRACT

Polymers comprising at least one unit of formulae (Continued)

-continued

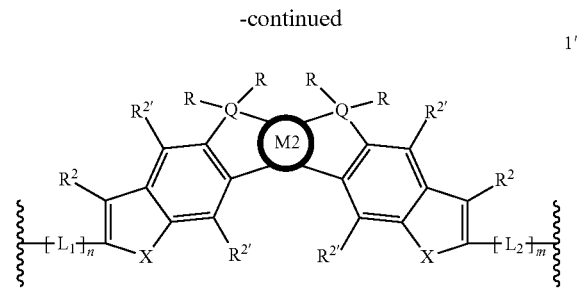

and compounds of the formulae

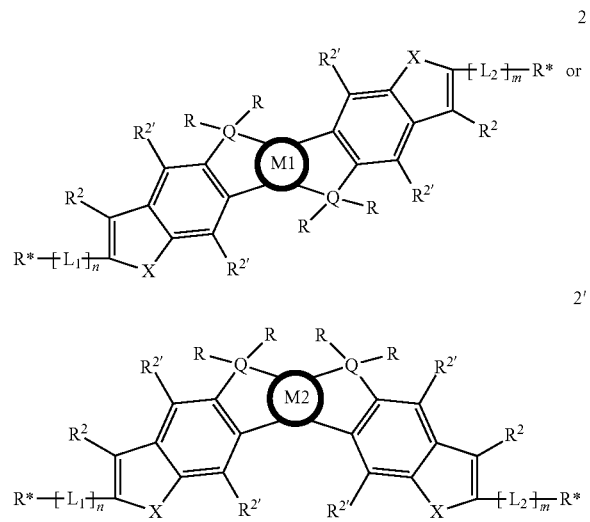

wherein, in formulae 1, 1', 2 and 2'
n is 0, 1, 2, 3 or 4
m is 0, 1, 2, 3 or 4
M1 and M2 are independently of each other an aromatic or heteroaromatic monocyclic or bicyclic ring system;
X is at each occurrence selected from the group consisting of O, S, Se or Te,
Q is at each occurrence selected from the group consisting of C, Si or Ge
R is at each occurrence selected from the group consisting of hydrogen, $C_{1-100}$-alkyl, $C_{2-100}$-alkenyl, $C_{2-100}$-alkynyl, $C_{5-12}$-cycloalkyl, $C_{6-18}$-aryl, a 5 to 20 membered heteroaryl, C(O)—$C_{1-100}$-alkyl, C(O)—$C_{5-12}$-cycloalkyl and C(O)—O$C_{1-100}$-alkyl.
$R^2$, $R^{2'}$, $R^{2''}$, $R^*$ are at each occurrence independently selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, $OR^{21}$, OC(O)—$R^{21}$, C(O)—$OR^{21}$, C(O)—$R^{21}$, $NR^{21}R^{22}$, $NR^{21}$—C(O)$R^{22}$, C(O)—$NR^{21}R^{22}$, $N[C(O)R^{21}][C(O)R^{22}]$, $SR^{21}$, halogen, CN, $SiR^{Sis}R^{Sit}R^{Siu}$ and OH,
$L^1$ and $L^2$ are independently from each other and at each occurrence selected from the group consisting of $C_{6-30}$-arylene, 5 to 30 membered heteroarylene,

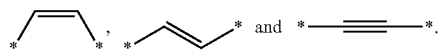

8 Claims, 4 Drawing Sheets

(51) Int. Cl.
    *H10K 85/10*    (2023.01)
    *H10K 85/60*    (2023.01)
(52) U.S. Cl.
    CPC ....... *H10K 85/151* (2023.02); *H10K 85/6576* (2023.02); *C08G 2261/124* (2013.01); *C08G 2261/146* (2013.01); *C08G 2261/1412* (2013.01); *C08G 2261/3243* (2013.01); *C08G 2261/3246* (2013.01); *C08G 2261/344* (2013.01); *C08G 2261/414* (2013.01); *C08G 2261/91* (2013.01); *C08G 2261/92* (2013.01); *C08G 2261/95* (2013.01)
(58) Field of Classification Search
    CPC ..... C07D 417/14; C07D 495/22; H01L 51/00; H01L 51/0074; H01L 51/0071; H01L 51/0072; H01L 51/0073; H01L 51/0558
    See application file for complete search history.

(56) References Cited

OTHER PUBLICATIONS

Li, Z. et al., "Alternating Copolymers of Cyclopenta[2,1-b;3,4-b'] dithiophene and Thieno[3,4-c]pyrrole-4,6-dione for High-Performance Polymer Solar Cells", Advanced Functional Materials, vol. 21, No. 17, 2011, XP001571450, pp. 3331-3336.
Chen. C-H. et al., "Donor-Acceptor Random Copolymers Based on a Ladder-Type Nonacyclic Unit: Synthesis, Characterization, and Photovoltaic Applications", Macromolecules, vol. 44, No. 21, 2011, XP055082172, pp. 8415-8424.
Yoshino. K. et al., "Dependence of luminescence in five membered heterocyclic conducting polymers on molecular structure and temperature", Journal of Applied Physics, vol. 68, No. 12, 1990, XP055374098, pp. 5976-5980.
Chen, H. et al., "Dithiopheneindenofluorene (TIF) Semiconducting Polymers with Very High Mobility in Field-Effect Transistors", Advanced Materials, vol. 29, No. 36, 2017, XP055480985, 6 pages.

THIENO-INDENO-MONOMERS AND POLYMERS

This application is a continuation application of U.S. application Ser. No. 16/462,437 tiled May 20, 2019, now U.S. Pat. No. 11,225,489, which is a National Stage of PCT/EP2017/0817633 filed Dec. 6, 2017 and claims the benefit of EP16207319.1 filed Dec. 29, 2016 and EP16202363.4 filed Dec. 6, 2016.

The present invention relates to new monomers and polymers made thereof, in particular thieno-indeno-monomers and polymers, to a process for the preparation of these monomers and polymers, to intermediates, to electronic devices comprising these polymers, as well as to the use of these polymers as semiconducting material.

Organic semiconducting materials can be used in electronic devices such as organic photovoltaic devices (OPVs), organic field-effect transistors (OFETs), organic light emitting diodes (OLEDs), organic photodiodes (OPDs) and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

For application in organic photovoltaic devices (OPVs), organic field-effect transistors (OFETs), and organic photodiodes (OPDs), it is further desirable that the organic semiconducting materials show high charge carrier mobility.

For application in organic photovoltaic devices (OPVs) and organic photodiodes (OPDs), the organic semiconducting materials should also show a strong absorption of the visible light.

It was the object of the present invention to provide organic semiconducting materials. This object is solved by the polymers of the invention, a process for preparing the polymers, intermediates for preparing the polymers electronic devices containing the polymers and the use of the polymers.

The polymers of the present invention comprise at least one unit of formula

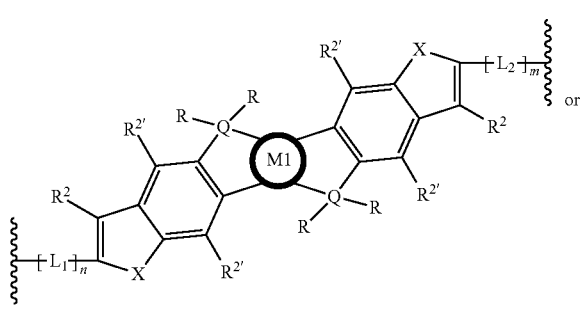

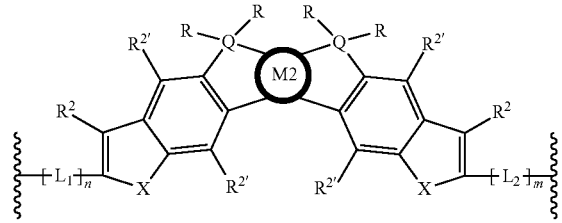

Also part of the invention are compounds of the formulae

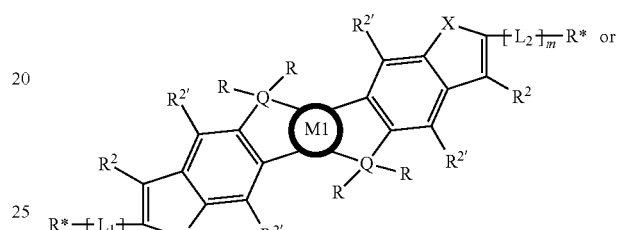

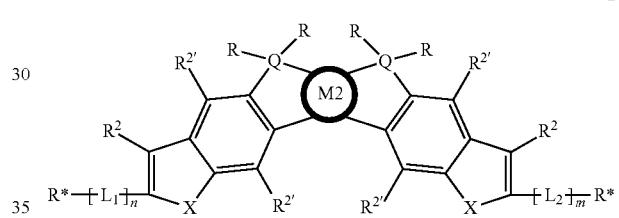

wherein, in formulae 1, 1', 2 and 2'
n is 0, 1, 2, 3 or 4
m is 0, 1, 2, 3 or 4
M1 and M2 are independently of each other an aromatic or heteroaromatic monocyclic or bicyclic ring system;
X is at each occurrence selected from the group consisting of O, S, Se or Te, preferably O, S or Se, more preferably S or Se, most preferably S;
Q is at each occurrence selected from the group consisting of C, Si or Ge, preferably C or Si, most preferably C;
R is at each occurrence selected from the group consisting of H, $C_{1-100}$-alkyl, $C_{2-100}$-alkenyl, $C_{2-100}$-alkynyl, $C_{5-12}$-cycloalkyl, $C_{6-18}$-aryl, a 5 to 20 membered heteroaryl, C(O)—$C_{1-100}$-alkyl, C(O)—$C_{5-12}$-cycloalkyl and C(O)—$OC_{1-100}$-alkyl,
wherein
$C_{1-100}$-alkyl, $C_{2-100}$-alkenyl and $C_{2-100}$-alkynyl can be substituted with one to forty substituents independently selected from the group consisting of $C_{5-8}$-cycloalkyl, $C_{6-14}$-aryl, 5 to 14 membered heteroaryl, $OR^a$, OC(O)—$R^a$, C(O)—$OR^a$, C(O)—$R^a$, $NR^aR^b$, $NR^a$—C(O)$R^b$, C(O)—$NR^aR^b$, N[C(O)$R^a$][C(O)$R^b$], $SR^a$, Si($R^{Sia}$)($R^{Sib}$)($R^{Sic}$), —O—Si($R^{Sia}$)($R^{Sib}$)($R^{Sic}$), halogen, CN, and $NO_2$; and at least two $CH_2$-groups, but not adjacent $CH_2$-groups, of $C_{1-100}$-alkyl, $C_{2-100}$-alkenyl and $C_{2-100}$-alkynyl can be replaced by O or S,
$C_{5-12}$-cycloalkyl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)$—$R^a$, $C(O)$—$OR^a$, $C(O)$—$R^a$, $NR^aR^b$, $NR^a$—$C(O)R^b$, $C(O)$—$NR^aR^b$, $N[C(O)R^a][C(O)R^b]$, $SR^a$, $Si(R^{Sia})(R^{Sib})(R^{Sic})$, —O—$Si(R^{Sia})(R^{Sib})(R^{Sic})$, halogen, CN, and $NO_2$; and one or two $CH_2$-groups, but not adjacent $CH_2$-groups, of $C_{5-12}$-cycloalkyl can be replaced by O, S, OC(O), CO, $NR^a$ or $NR^a$—CO, $C_{6-18}$-aryl and 5 to 20 membered heteroaryl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)$—$R^a$, $C(O)$—$OR^a$, $C(O)$—$R^a$, $NR^aR^b$, $NR^a$—$C(O)R^b$, $C(O)$—$NR^aR^b$, $N[C(O)R^a][C(O)R^b]$, $SR^a$, $Si(R^{Sia})(R^{Sib})(R^{Sic})$, —O—$Si(R^{Sia})(R^{Sib})(R^{Sic})$, halogen, CN, and $NO_2$, wherein $R^a$ and $R^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-14}$-aryl, O-5 to 14 membered heteroaryl, —[O—$SiR^{Sid}R^{Sie}]_o$—$R^{Sif}$, $NR^5R^6$, halogen and O—C(O)—$R^5$, wherein o is an integer from 1 to 50, $R^{Sid}$, $R^{Sie}$, $R^{Sif}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-14}$-aryl, O-5 to 14 membered heteroaryl, —[O—$SiR^{Sig}R^{Sih}]_p$—$R^{Sii}$, $NR^{50}R^{60}$, halogen and O—C(O)—$R^{50}$;

wherein p is an integer from 1 to 50, $R^{Sig}R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, 0-$Si(CH_3)_3$, $NR^{500}R^{600}$, halogen and O—C(O)—$R^{500}$, $R^5$, $R^6$, $R^{50}$, $R^{60}$, $R^{500}$ and $R^{600}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, and 5 to 14 membered heteroaryl, $C_{1-60}$-alkyl, $C_{2-60}$-alkenyl and $C_{2-60}$-alkynyl can be substituted with one to twenty substituents selected from the group consisting of $C_{5-6}$-cycloalkyl, $C_{6-10}$-aryl, $OR^c$, $OC(O)$—$R^c$, $C(O)$—$OR^c$, $C(O)$—$R^c$, $NR^cR^d$, $NR^c$—$C(O)R^d$, $C(O)$—$NR^cR^d$, $N[C(O)R^c][C(O)R^d]$, $SR^c$, $Si(R^{Sij})(R^{Sik})(R^{Sil})$, —O—$Si(R^{Sij})(R^{Sik})(R^{Sil})$, halogen, CN, and $NO_2$ and at least two $CH_2$-groups, but not adjacent $CH_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, $OR^c$, $OC(O)$—$R^c$, $C(O)$—$OR^c$, $C(O)$—$R^c$, $NR^cR^d$, $NR^c$—$C(O)R^d$, $C(O)$—$NR^cR^d$, $N[C(O)R^c][C(O)R^d]$, $SR^c$, $Si(R^{Sij})(R^{Sik})(R^{Sil})$, —O—$Si(R^{Sij})(R^{Sik})(R^{Sil})$, halogen, CN, and $NO_2$; and one or two $CH_2$-groups, but not adjacent $CH_2$-groups, of $C_{5-8}$-cycloalkyl can be replaced by O, S, OC(O), CO, $NR^c$ or $NR^c$—CO, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, $OR^c$, $OC(O)$—$R^c$, $C(O)$—$OR^c$, $C(O)$—$R^c$, $NR^cR^d$, $NR^c$—$C(O)R^d$, $C(O)$—$NR^cR^d$, $N[C(O)R^c][C(O)R^d]$, $SR^c$, $Si(R^{Sij})(R^{Sik})(R^{Sil})$, —O—$Si(R^{Sij})(R^{Sik})(R^{Sil})$, halogen, CN and $NO_2$;

wherein $R^c$ and $R^d$ are independently selected from the group consisting of H, $C_{1-30}$-alkyl, $C_{2-30}$-alkenyl and $C_{2-30}$-alkynyl, $R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, 0-5 to 10 membered heteroaryl, —[O—$SiR^{Sim}R^{Sin}]$, —$R^{Sio}$, $NR^7R^8$, halogen, and O—C(O)—$R^7$, wherein q is an integer from 1 to 50, $R^{Sim}$, $R^{Sin}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, —[O—$SiR^{Sip}R^{Siq}]_r$—$R^{Sir}$, $NR^{70}R^{80}$, halogen, and O—C(O)—$R^{70}$;

wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, O—$Si(CH_3)_3$, $NR^{700}R^{800}$, halogen and O—C(O)—$R^{700}$, $R^7$, $R^8$, $R^{70}$, $R^{80}$, $R^{700}$ and $R^{800}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, and 5 to 10 membered heteroaryl, $C_{1-30}$-alkyl, $C_{2-30}$-alkenyl and $C_{2-30}$-alkynyl can be substituted with one to ten substituents selected from the group consisting of halogen, CN and $NO_2$, $R^2$, $R^{2'}$, $R^{2''}$, $R^*$ are at each occurrence independently selected from the group consisting of hydrogen, $C_{1-30}$-alkyl, $C_{2-30}$-alkenyl, $C_{2-30}$-alkynyl, $C_{5-12}$-cycloalkyl, $C_{6-18}$-aryl, 5 to 20 membered heteroaryl, OR$^{21}$, OC(O)—R$^{21}$, C(O)—OR$^{21}$, C(O)—R$^{21}$, NR$^{21}$R$^{22}$, NR$^{21}$—C(O)R$^{22}$, C(O)—NR$^{21}$R$^{22}$, N[C(O)R$^{21}$][C(O)R$^{22}$], SR$^{21}$, halogen, CN, SiR$^{Sis}$R$^{Sit}$R$^{Siu}$ and OH,
wherein
R$^{21}$ and R$^{22}$ and are independently selected from the group consisting of H, C$_{1\text{-}30}$-alkyl, C$_{2\text{-}30}$-alkenyl, C$_{2\text{-}30}$-alkynyl, C$_{5\text{-}12}$-cycloalkyl, C$_{6\text{-}18}$-aryl and 5 to 20 membered heteroaryl, and C$_{1\text{-}30}$-alkyl, C$_{2\text{-}30}$-alkenyl and C$_{2\text{-}30}$-alkynyl can be substituted with one to ten substituents independently selected from the group consisting of C$_{5\text{-}8}$-cycloalkyl, C$_{6\text{-}14}$-aryl, 5 to 14 membered heteroaryl, OR$^e$, OC(O)—R$^e$, C(O)—OR$^e$, C(O)—R$^e$, NR$^e$R$^f$, NR$^e$—C(O)R$^f$, C(O)—NR$^e$R$^f$, N[C(O)R$^e$][C(O)R$^f$], SR$^e$, halogen, CN, SiR$^{Sis}$R$^{Sit}$R$^{Siu}$ and NO$_2$; and at least two CH$_2$-groups, but not adjacent CH$_2$-groups, of C$_{1\text{-}30}$-alkyl, C$_{2\text{-}30}$-alkenyl and C$_{2\text{-}30}$-alkynyl can be replaced by O or S, C$_{5\text{-}12}$-cycloalkyl can be substituted with one to six substituents independently selected from the group consisting of C$_{1\text{-}20}$-alkyl, C$_{2\text{-}20}$-alkenyl and C$_{2\text{-}20}$-alkynyl, C$_{5\text{-}8}$-cycloalkyl, C$_{6\text{-}14}$-aryl, 5 to 14 membered heteroaryl, OR$^e$, OC(O)—R$^e$, C(O)—OR$^e$, C(O)—R$^e$, NR$^e$R$^f$, NR$^e$—C(O)R$^f$, C(O)—NR$^e$R$^f$, N[C(O)R$^e$][C(O)R$^f$], SR$^e$, halogen, CN, SiR$^{Sis}$R$^{Sit}$R$^{Siu}$ and NO$_2$; and one or two CH$_2$-groups, but not adjacent CH$_2$-groups, of C$_{5\text{-}12}$-cycloalkyl can be replaced by O, S, OC(O), CO, NR$^e$ or NR$^e$—CO, C$_{6\text{-}18}$-aryl and 5 to 20 membered heteroaryl can be substituted with one to six substituents independently selected from the group consisting of C$_{1\text{-}20}$-alkyl, C$_{2\text{-}20}$-alkenyl, C$_{2\text{-}20}$-alkynyl, C$_{5\text{-}8}$-cycloalkyl, C$_{6\text{-}14}$-aryl, 5 to 14 membered heteroaryl, OR$^e$, OC(O)—R$^e$, C(O)—OR$^e$, C(O)—R$^e$, NR$^e$R$^f$, NR$^e$—C(O)R$^f$, C(O)—NR$^e$R$^f$, N[C(O)R$^e$][C(O)R$^f$], SR$^e$, halogen, CN, SiR$^{Sis}$R$^{Sit}$R$^{Siu}$ and NO$_2$,
wherein
R$^{Sis}$, R$^{Sit}$ and R$^{Siu}$ are independently from each other selected from the group consisting of H, C$_{1\text{-}20}$-alkyl, C$_{2\text{-}20}$-alkenyl, C$_{2\text{-}20}$-alkynyl, C$_{5\text{-}6}$-cycloalkyl, phenyl and O—Si(CH$_3$)$_3$, R$^e$ and R$^f$ are independently selected from the group consisting of H, C$_{1\text{-}20}$-alkyl, C$_{2\text{-}20}$-alkenyl, C$_{2\text{-}20}$-alkynyl, C$_{5\text{-}8}$-cycloalkyl, C$_{6\text{-}14}$-aryl, and 5 to 14 membered heteroaryl,
wherein
C$_{1\text{-}20}$-alkyl, C$_{2\text{-}20}$-alkenyl and C$_{2\text{-}20}$-alkynyl can be substituted with one to five substituents selected from the group consisting of C$_{5\text{-}6}$-cycloalkyl, C$_{6\text{-}10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;
C$_{5\text{-}8}$-cycloalkyl can be substituted with one to five substituents selected from the group consisting of C$_{1\text{-}10}$-alkyl, C$_{2\text{-}10}$-alkenyl, C$_{2\text{-}10}$-alkynyl, C$_{5\text{-}6}$-cycloalkyl, C$_{6\text{-}10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;
C$_{6\text{-}14}$-aryl and 5 to 14 membered heteroaryl can be substituted with one to five substituents independently selected from the group consisting of C$_{1\text{-}10}$-alkyl, C$_{2\text{-}10}$-alkenyl, C$_{2\text{-}10}$-alkynyl, C$_{5\text{-}6}$-cycloalkyl, C$_{6\text{-}10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;
wherein
R$^g$ and R$^h$ are independently selected from the group consisting of H, C$_{1\text{-}10}$-alkyl, C$_{2\text{-}10}$-alkenyl and C$_{2\text{-}10}$-alkynyl,
wherein
C$_{1\text{-}10}$-alkyl, C$_{2\text{-}10}$-alkenyl and C$_{2\text{-}10}$-alkynyl can be substituted with one to five substituents selected from the group consisting of halogen, CN and NO$_2$, L$^1$ and L$^2$ are independently from each other and at each occurrence selected from the group consisting of C$_{6\text{-}30}$-arylene, 5 to 30 membered heteroarylene,

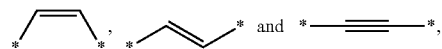

wherein
C$_{6\text{-}30}$-arylene and 5 to 30 membered heteroarylene can be substituted with one to six substituents R$^3$ at each occurrence selected from the group consisting of C$_{1\text{-}30}$-alkyl, C$_{2\text{-}30}$-alkenyl, C$_{2\text{-}30}$-alkynyl, C$_{5\text{-}12}$-cycloalkyl, C$_{6\text{-}18}$-aryl and 5 to 20 membered heteroaryl, OR$^{31}$, OC(O)—R$^{31}$, C(O)—OR$^{31}$, C(O)—R$^{31}$, NR$^{31}$R$^{32}$, NR$^{31}$—C(O)R$^{32}$, C(O)—NR$^{31}$R$^{32}$, N[C(O)R$^{31}$][C(O)R$^{32}$], SR$^{31}$, halogen, CN, SiR$^{Siv}$R$^{Siw}$R$^{Six}$ and OH, and
wherein

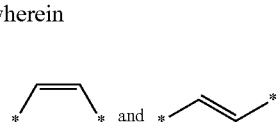

can be substituted with one or two substituents R$^4$ at each occurrence selected from the group consisting of C$_{1\text{-}30}$-alkyl, C$_{2\text{-}30}$-alkenyl, C$_{2\text{-}30}$-alkynyl, C$_{5\text{-}12}$-cycloalkyl, C$_{6\text{-}18}$-aryl and 5 to 20 membered heteroaryl, C(O)—R$^{41}$, C(O)—NR$^{41}$R$^{42}$, C(O)—OR$^{41}$ and CN,
wherein
R$^{31}$, R$^{32}$, R$^{41}$ und R$^{42}$ are independently from each other and at each occurrence selected from the group consisting of H, C$_{1\text{-}30}$-alkyl, C$_{2\text{-}30}$-alkenyl, C$_{2\text{-}30}$-alkynyl, C$_{5\text{-}12}$-cycloalkyl, C$_{6\text{-}18}$-aryl and 5 to 20 membered heteroaryl, and
wherein
C$_{1\text{-}30}$-alkyl, C$_{2\text{-}30}$-alkenyl and C$_{2\text{-}30}$-alkynyl can be substituted with one to ten substituents independently selected from the group consisting of C$_{5\text{-}8}$-cycloalkyl, C$_{6\text{-}14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, SiR$^{Siv}$R$^{Siw}$R$^{Six}$ and NO$_2$; and at least two CH$_2$-groups, but not adjacent CH$_2$-groups of C$_{1\text{-}30}$-alkyl, C$_{2\text{-}30}$-alkenyl and C$_{2\text{-}30}$-alkynyl can be replaced by O or S, C$_{5\text{-}12}$-cycloalkyl can be substituted with one to six substituents independently selected from the group consisting of C$_{1\text{-}20}$-alkyl, C$_{2\text{-}20}$-alkenyl and C$_{2\text{-}20}$-alkynyl, C$_{5\text{-}8}$-cycloalkyl, C$_{6\text{-}14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, SiR$^{Siv}$R$^{Siw}$R$^{Six}$ and NO$_2$; and one or two CH$_2$-groups, but not adjacent CH$_2$-groups, of C$_{5\text{-}12}$-cycloalkyl can be replaced by O, S, OC(O), CO, NR$^i$ or NR$^i$—CO, $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$, wherein $R^{Siv}$, $R^{Siw}$, $R^{Six}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—$Si(CH_3)_3$, $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, wherein $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$;

wherein $R^k$ and $R^l$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$, Halogen can be F, Cl, Br and I.

X are preferably at each occurrence the same.

Q are preferably at each occurrence the same.

$R^2$ are preferably at each occurrence the same.

R* are preferably at each occurrence the same.

$C_{1-4}$-alkyl, $C_{1-10}$-alkyl, $C_{1-20}$-alkyl, $C_{1-30}$-alkyl, $C_{1-36}$-alkyl, $C_{1-50}$-alkyl, $C_{1-60}$-alkyl and $C_{1-100}$-alkyl can be branched or unbranched. Examples of $C_{1-4}$-alkyl are methyl, ethyl, n-propyl, isopropyl, n-butyl, sec-butyl, isobutyl and tert-butyl. Examples of $C_{1-10}$-alkyl are $C_{1-4}$-alkyl, n-pentyl, neopentyl, isopentyl, n-(1-ethyl)propyl, n-hexyl, n-heptyl, n-octyl, n-(2-ethyl)hexyl, n-nonyl and n-decyl. Examples of $C_{1-20}$-alkyl are $C_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl, $C_{1-36}$-alkyl, $C_{1-50}$-alkyl, $C_{1-60}$-alkyl and $C_{1-100}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$).

$C_{2-10}$-alkenyl, $C_{2-20}$-alkenyl, $C_{2-30}$-alkenyl, $C_{2-60}$-alkenyl and $C_{2-100}$-alkenyl can be branched or unbranched. Examples of $C_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of $C_{2-20}$-alkenyl, $C_{2-60}$-alkenyl and $C_{2-100}$-alkenyl are $C_{2-10}$-alkenyl and linoleyl ($C_{18}$), linolenyl ($C_{18}$), oleyl ($C_{18}$), and arachidonyl ($C_{20}$). Examples of $C_{2-30}$-alkenyl are $C_{2-20}$-alkenyl and erucyl ($C_{22}$).

$C_{2-10}$-alkynyl, $C_{2-20}$-alkynyl, $C_{2-30}$-alkynyl, $C_{2-60}$-alkynyl and $C_{2-100}$-alkynyl can be branched or unbranched. Examples of $C_{2-10}$-alkynyl are ethynyl, 2-propynyl, 2-butynyl, 3-butynyl, pentynyl, hexynyl, heptynyl, octynyl, nonynyl and decynyl. Examples of $C_{2-20}$-alkynyl, $C_{2-30}$-alkynyl, $C_{2-60}$-alkynyl and $C_{2-100}$-alkynyl are undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-6}$-cycloalkyl are cyclopentyl and cyclohexyl. Examples of $C_{5-8}$-cycloalkyl are $C_{5-6}$-cycloalkyl and cycloheptyl and cyclooctyl. $C_{5-12}$-cycloalkyl are $C_{5-8}$-cycloalkyl and cyclononyl, cyclodecyl, cycloundecyl and cyclododecyl.

Examples of $C_{6-10}$-aryl are phenyl,

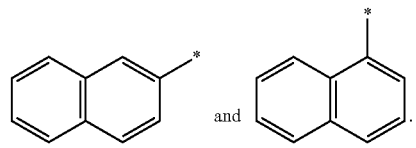 [SMILES: *c1ccc2ccccc2c1 ; *c1cccc2ccccc12]

Examples of $C_{6-14}$-aryl are $C_{6-10}$-aryl and

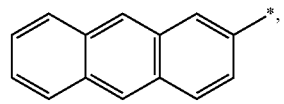

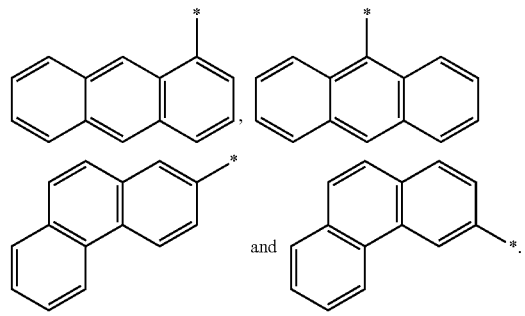

Examples of $C_{6-18}$-aryl are $C_{6-14}$-aryl and

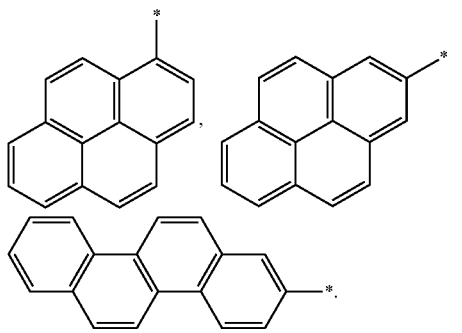

5 to 10 membered heteroaryl are 5 to 10 membered monocyclic or polycyclic, such as dicyclic, tricyclic or tetracyclic, ring systems, which comprise at least one heteroaromatic ring, and which may also comprise non-aromatic rings, which may be substituted by =O.

5 to 14 membered heteroaryl are 5 to 14 membered monocyclic or polycyclic, such as dicyclic, tricyclic or tetracyclic, ring systems, which comprise at least one heteroaromatic ring, and which may also comprise non-aromatic rings, which may be substituted by =O.

5 to 20 membered heteroaryl are 5 to 20 membered monocyclic or polycyclic, such as dicyclic, tricyclic or tetracyclic, ring systems, which comprise at least one heteroaromatic ring, and which may also comprise non-aromatic rings, which may be substituted by =O.

Examples of 5 to 10 membered heteroaryl are

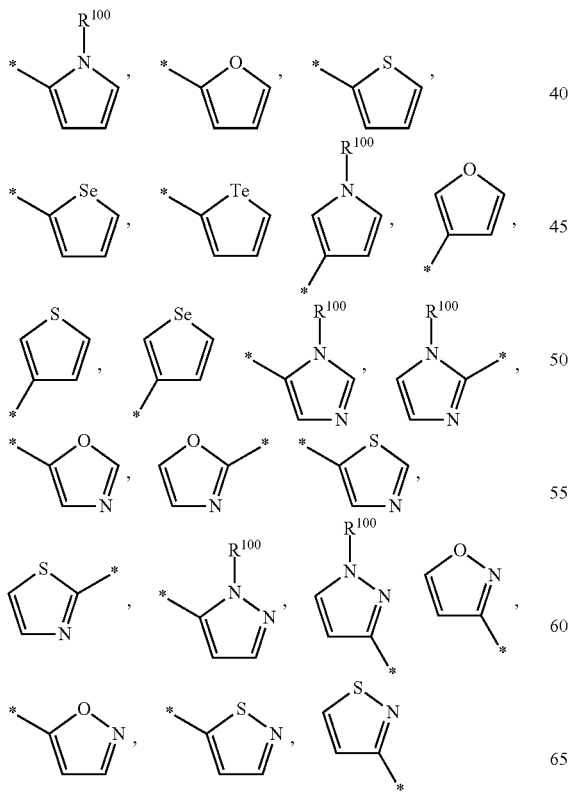

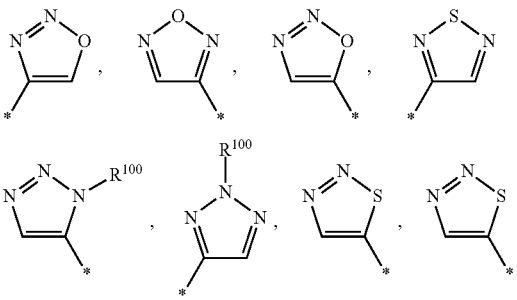

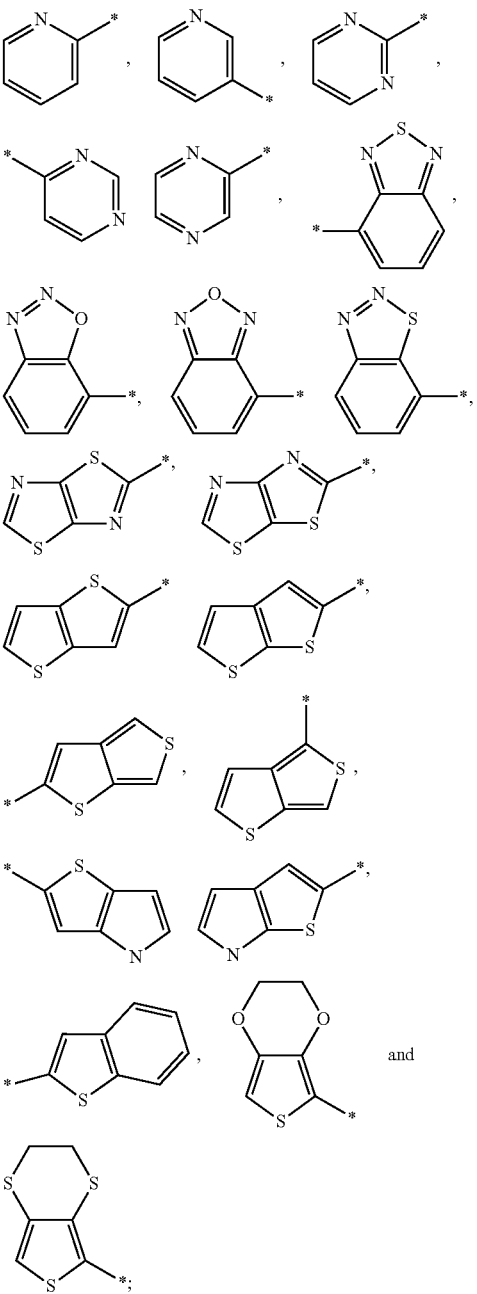

Examples of 5 to 14 membered heteroaryl are the examples given for the 5 to 10 membered heteroaryl and
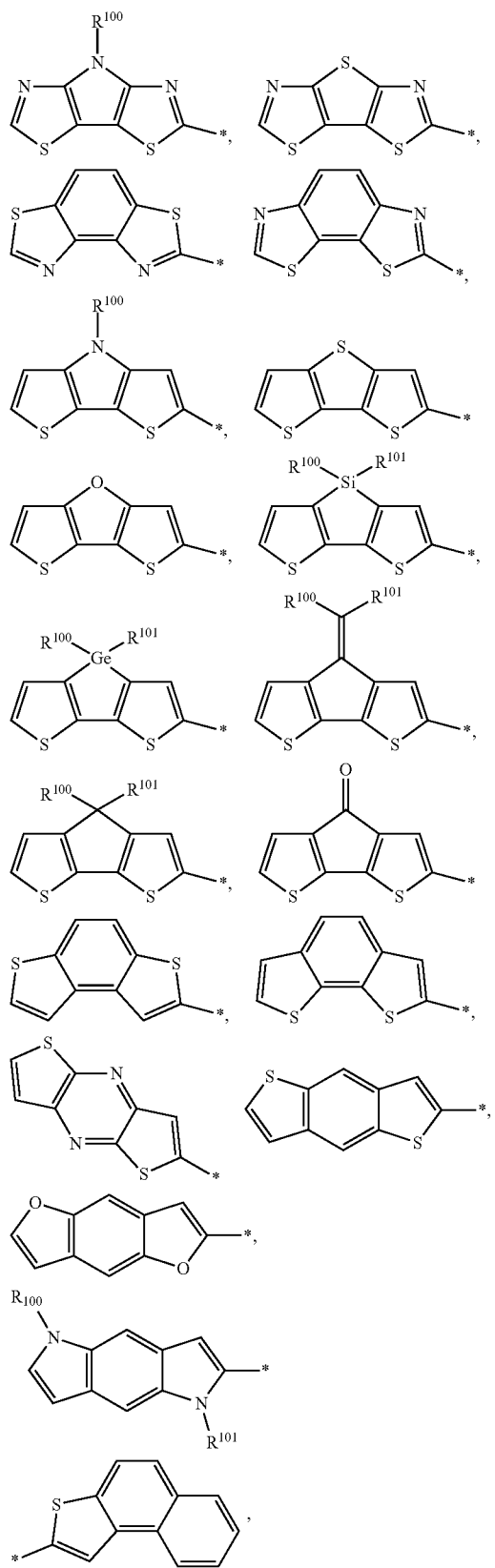
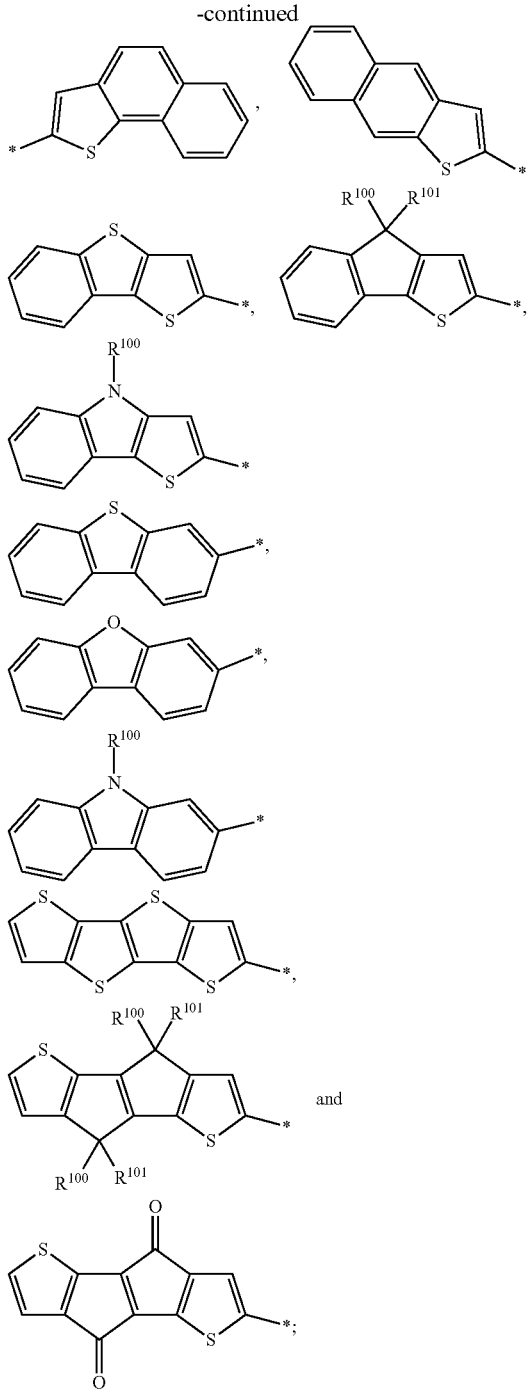
Examples of 5 to 20 membered heteroaryl are the examples given for the 5 to 14 membered heteroaryl and
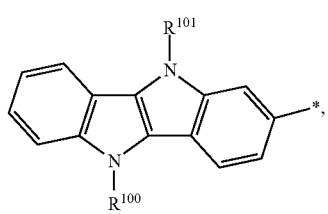

-continued

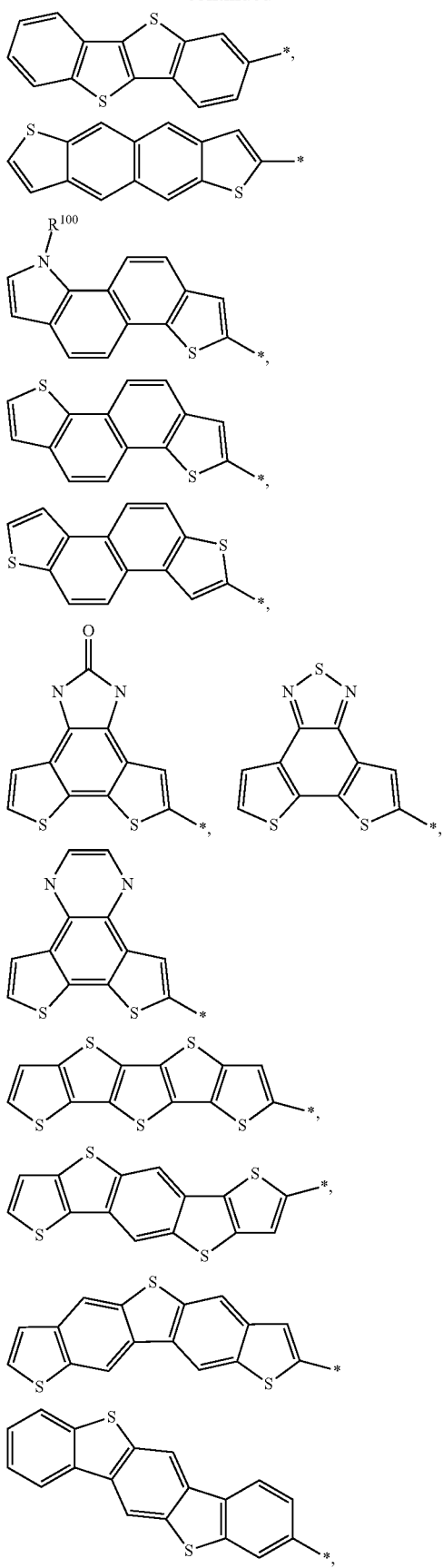

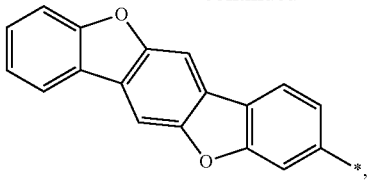

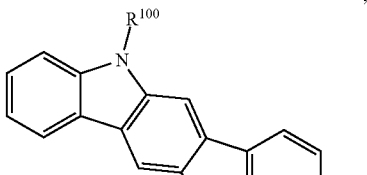

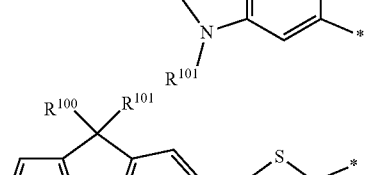

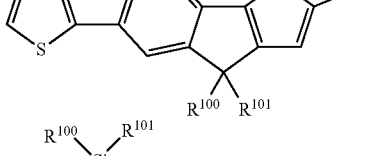

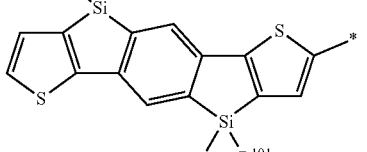

and wherein
$R^{100}$ and $R^{101}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{100}$ and $R^{101}$, if attached to the same atom, together with the atom, to which they are attached, form a 5 to 12 membered ring system, wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^g$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$,
$C(O)$—$R^q$, $NR^qR^r$, $NR^q$—$C(O)R^r$, $C(O)$—$NR^qR^r$, $N[C(O)R^q][C(O)R^r]$, $SR^q$, halogen, CN, and $NO_2$;

5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^q$, $OC(O)$—$R^q$, $C(O)$—$OR^q$, $C(O)$—$R^q$, $NR^gR^r$, $NR^q$—$C(O)R^r$, $C(O)$—$NR^qR^r$, $N[C(O)R^q][C(O)R^r]$, $SR^q$, halogen, CN, and $NO_2$;

wherein $R^q$ and $R^r$ are independently selected from the group consisting of H, $C_{1-10}$-alkyl, $C_{2-10}$-alkenyl and $C_{2-10}$-alkynyl, wherein $C_{1-10}$-alkyl, $C_{2-10}$-alkenyl and $C_{2-10}$-alkynyl can be substituted with one to five substituents selected from the group consisting of halogen, CN and $NO_2$.

$C_{6-30}$-arylene is a 6 to 30 membered monocyclic or polycyclic, such as dicyclic, tricyclic, tetracyclic, pentacyclic or hexacyclic ring system, which comprises at least one C-aromatic ring, and which may also comprise non-aromatic rings or heteroaromatic rings, which may be substituted by =O.

Examples of $C_{6-30}$-arylene are

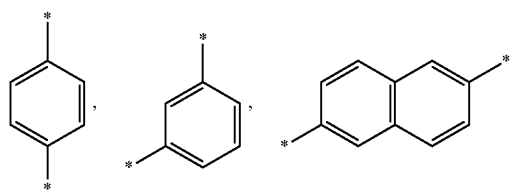

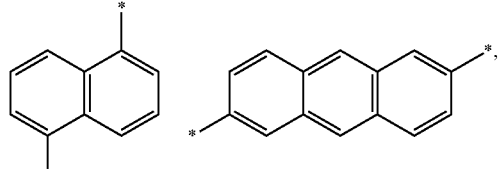

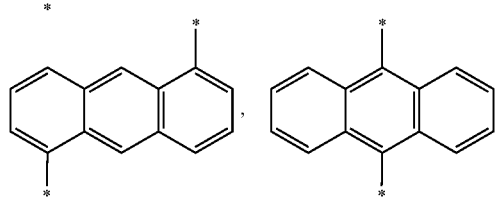

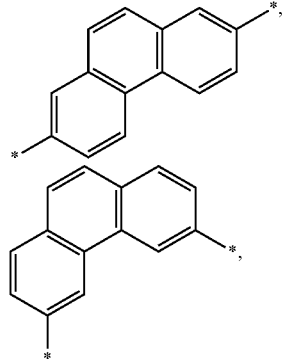

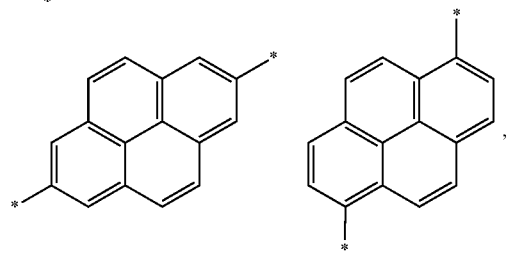

-continued

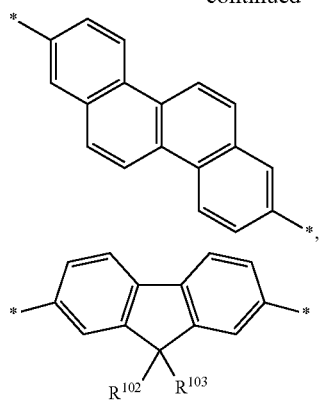

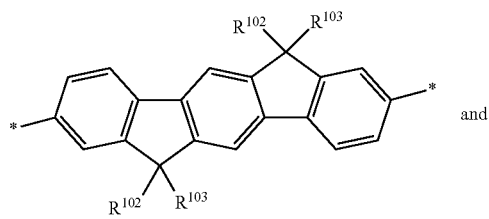

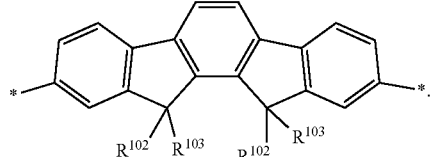

and

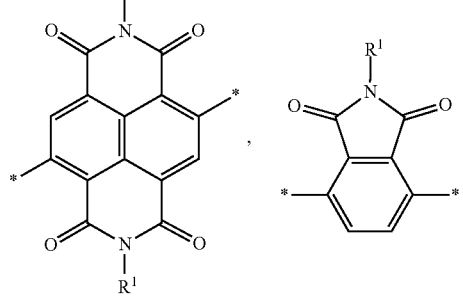

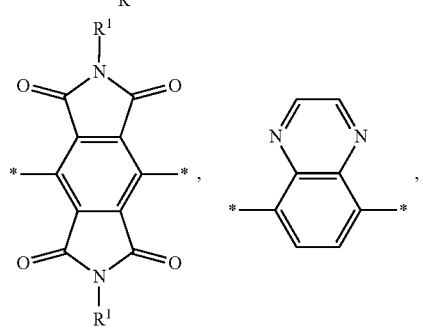

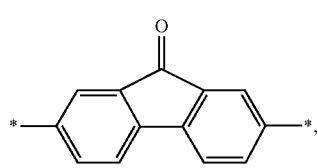

-continued

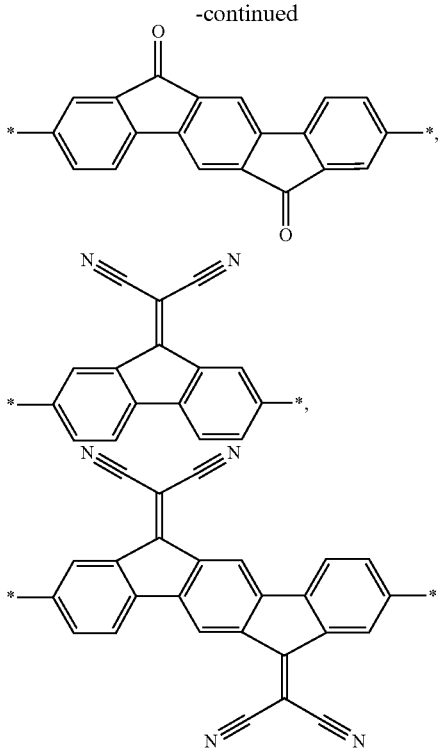

wherein

R[1] is at each occurrence selected from the group consisting of H, $C_{1-100}$-alkyl, $C_{2-100}$-alkenyl, $C_{2-100}$-alkynyl, $C_{5-12}$-cycloalkyl, $C_{6-18}$-aryl, a 5 to 20 membered heteroaryl, C(O)—$C_{1-100}$-alkyl, C(O)—$C_{5-12}$-cycloalkyl and C(O)—OC$_{1-100}$-alkyl, wherein $C_{1-100}$-alkyl, $C_{2-100}$-alkenyl and $C_{2-100}$-alkynyl can be substituted with one to forty substituents independently selected from the group consisting of $C_{5-8}$-cycloalkyl, $C_{6-14}$-aryl, 5 to 14 membered heteroaryl, OR$^a$, OC(O)—R$^a$, C(O)—OR$^a$, C(O)—R$^a$, NR$^a$R$^b$, NR$^a$—C(O)R$^b$, C(O)—NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$; and at least two CH$_2$-groups, but not adjacent CH$_2$-groups, of $C_{1-100}$-alkyl, $C_{2-100}$-alkenyl and $C_{2-100}$-alkynyl can be replaced by O or S, $C_{5-12}$-cycloalkyl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, OR$^a$, OC(O)—R$^a$, C(O)—OR$^a$, C(O)—R$^a$, NR$^a$R$^b$, NR$^a$—C(O)R$^b$, C(O)—NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$; and one or two CH$_2$-groups, but not adjacent CH$_2$-groups, of $C_{5-12}$-cycloalkyl can be replaced by O, S, OC(O), CO, NR$^a$ or NR$^a$—CO, $C_{6-18}$-aryl and 5 to 20 membered heteroaryl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, OR$^a$, OC(O)—R$^a$, C(O)—OR$^a$, C(O)—R$^a$, NR$^a$R$^b$, NR$^a$—C(O)R$^b$, C(O)—NR$^a$R$^b$, N[C(O)R$^a$][C(O)R$^b$], SR$^a$, Si(R$^{Sia}$)(R$^{Sib}$)(R$^{Sic}$), —O—Si(R$^{Sia}$)(R$^{Sib}$)(R$^{Sic}$), halogen, CN, and NO$_2$, wherein R$^a$ and R$^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, R$^{Sia}$, R$^{Sib}$ and R$^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-14}$-aryl, O-5 to 14 membered heteroaryl, —[O—SiR$^{Sid}$R$^{Sie}$]$_o$—R$^{Sif}$, NR$^5$R$^6$, halogen and O—C(O)—R$^5$, wherein o is an integer from 1 to 50, R$^{Sid}$, R$^{Sie}$, R$^{Sif}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, O—$C_{1-60}$-alkyl, O—$C_{2-60}$-alkenyl, O—$C_{2-60}$-alkynyl, O—$C_{5-8}$-cycloalkyl, O—$C_{6-14}$-aryl, O-5 to 14 membered heteroaryl, —[O—SiR$^{Sig}$R$^{Sih}$]$_p$—R$^{Sii}$, NR$^{50}$R$^{60}$, halogen and O—C(O)—R$^{50}$;

wherein p is an integer from 1 to 50,

R$^{Sig}$R$^{Sih}$, R$^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, 0-5 to 10 membered heteroaryl, O—Si(CH$_3$)$_3$, NR$^{500}$R$^{600}$, halogen and O—C(O)—R$^{500}$, R$^5$, R$^6$, R$^{50}$, R$^{60}$, R$^{500}$ and R$^{600}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, and 5 to 14 membered heteroaryl, $C_{1-60}$-alkyl, $C_{2-60}$-alkenyl and $C_{2-60}$-alkynyl can be substituted with one to twenty substituents selected from the group consisting of $C_{5-6}$-cycloalkyl, $C_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN, and NO$_2$; and at least two CH$_2$-groups, but not adjacent CH$_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN, and NO$_2$; and one or two CH$_2$-groups, but not adjacent CH$_2$-groups, of $C_{5-8}$-cycloalkyl can be replaced by O, S, OC(O), CO, NR$^c$ or NR$^c$—CO, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$R$^d$, NR$^c$—C(O)R$^d$, C(O)—NR$^c$R$^d$, N[C(O)R$^c$][C(O)R$^d$], SR$^c$, Si(R$^{Sij}$)(R$^{Sik}$)(R$^{Sil}$), —O—Si(R$^{Sij}$)(R$^{Sik}$)(R$^{Sil}$), halogen, CN and NO$_2$;

wherein
R$^c$ and R$^d$ are independently selected from the group consisting of H, C$_{1-30}$-alkyl, C$_{2-30}$-alkenyl and C$_{2-30}$-alkynyl,
R$^{Sij}$, R$^{Sik}$ and R$^{Sil}$ are independently selected from the group consisting of H, C$_{1-30}$-alkyl, C$_{2-30}$-alkenyl, C$_{2-30}$-alkynyl, C$_{5-6}$-cycloalkyl, C$_{6-10}$-aryl, 5 to 10 membered heteroaryl, O—C$_{1-30}$-alkyl, O—C$_{2-30}$-alkenyl, O—C$_{2-30}$-alkynyl, O—C$_{5-6}$-cycloalkyl, O—C$_{6-10}$-aryl, O-5 to 10 membered heteroaryl, —[O—SiR$^{Sim}$R$^{Sin}$]$_q$—R$^{Sio}$, NR$^7$R$^8$, halogen, and O—C(O)—R$^7$,
wherein
q is an integer from 1 to 50,
R$^{Sim}$, R$^{Sin}$, R$^{Sio}$ are independently selected from the group consisting of H, C$_{1-30}$-alkyl, C$_{2-30}$-alkenyl, C$_{2-30}$-alkynyl, C$_{5-6}$-cycloalkyl, C$_{6-10}$-aryl, 5 to 10 membered heteroaryl, O—C$_{1-30}$-alkyl, O—C$_{2-30}$-alkenyl, O—C$_{2-30}$-alkynyl, O—C$_{5-6}$-cycloalkyl, O—C$_{6-10}$-aryl, O-5 to 10 membered heteroaryl, —[O—SiR$^{Sip}$R$^{Siq}$]$_r$—R$^{Sir}$, NR$^{70}$R$^{80}$, halogen, and O—C(O)—R$^{70}$;
wherein
r is an integer from 1 to 50,
R$^{Sip}$, R$^{Siq}$, R$^{Sir}$ are independently selected from the group consisting of H, C$_{1-30}$-alkyl, C$_{2-30}$-alkenyl, C$_{2-30}$-alkynyl, C$_{5-6}$-cycloalkyl, C$_{6-10}$-aryl, 5 to 10 membered heteroaryl, O—C$_{1-30}$-alkyl, O—C$_{2-30}$-alkenyl, O—C$_{2-30}$-alkynyl, O—C$_{5-6}$-cycloalkyl, O—C$_{6-10}$-aryl, O-5 to 10 membered heteroaryl, O—Si(CH$_3$)$_3$, NR$^{700}$OR$^{800}$, halogen and O—C(O)—R$^{700}$,
R$^7$, R$^8$, R$^{70}$, R$^{80}$, R$^{700}$ and R$^{800}$ are independently selected from the group consisting of H, C$_{1-30}$-alkyl, C$_{2-30}$-alkenyl, C$_{2-30}$-alkynyl, C$_{5-6}$-cycloalkyl, C$_{6-10}$-aryl, and 5 to 10 membered heteroaryl,
C$_{1-30}$-alkyl, C$_{2-30}$-alkenyl and C$_{2-30}$-alkynyl can be substituted with one to ten substituents selected from the group consisting of halogen, CN and NO$_2$,
R$^{102}$ and R$^{103}$ are independently and at each occurrence selected from the group consisting of H, C$_{1-20}$-alkyl, C$_{2-20}$-alkenyl, C$_{2-20}$-alkynyl, C$_{5-8}$-cycloalkyl, C$_{6-14}$-aryl, and 5 to 14 membered heteroaryl, or R$^{102}$ and R$^{103}$, if attached to the same atom, together with the atom, to which they are attached, form a 5 to 12 membered ring system,
wherein
C$_{1-20}$-alkyl, C$_{2-20}$-alkenyl and C$_{2-20}$-alkynyl can be substituted with one to five substituents selected from the group consisting of C$_{5-6}$-cycloalkyl, C$_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;
C$_{5-8}$-cycloalkyl can be substituted with one to five substituents selected from the group consisting of C$_{1-10}$-alkyl, C$_{2-10}$-alkenyl, C$_{2-10}$-alkynyl, C$_{5-6}$-cycloalkyl, C$_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;
C$_{6-14}$-aryl and 5 to 14 membered heteroaryl can be substituted with one to five substituents independently selected from the group consisting of C$_{1-10}$-alkyl, C$_{2-10}$-alkenyl, C$_{2-10}$-alkynyl, C$_{5-6}$-cycloalkyl, C$_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;
5 to 12 membered ring system can be substituted with one to five substituents selected from the group consisting of C$_{1-10}$-alkyl, C$_{2-10}$-alkenyl, C$_{2-10}$-alkynyl, C$_{5-6}$-cycloalkyl, C$_{6-10}$-aryl, 5 to 10 membered heteroaryl, OR$^s$, OC(O)—R$^t$, C(O)—OR$^s$, C(O)—R$^s$, NR$^s$R$^t$, NR$^s$—C(O)R$^t$, C(O)—NR$^s$R$^t$, N[C(O)R$^s$][C(O)R$^t$], SR$^s$, halogen, CN, and NO$_2$;
wherein
R$^s$ and R$^t$ are independently selected from the group consisting of H, C$_{1-10}$-alkyl, C$_{2-10}$-alkenyl and C$_{2-10}$-alkynyl,
wherein
C$_{1-10}$-alkyl, C$_{2-10}$-alkenyl and C$_{2-10}$-alkynyl can be substituted with one to five substituents selected from the group consisting of halogen, CN and NO$_2$.
5 to 30 membered heteroarylene is a 5 to 30 membered monocyclic or polycyclic, such as dicyclic, tricyclic, tetracyclic, pentacyclic or hexacyclic ring system, which comprises at least one heteroaromatic ring, and which may also comprise aromatic rings or non-aromatic rings, which may be substituted by =O.

Examples of 5 to 30 membered heteroarylene are

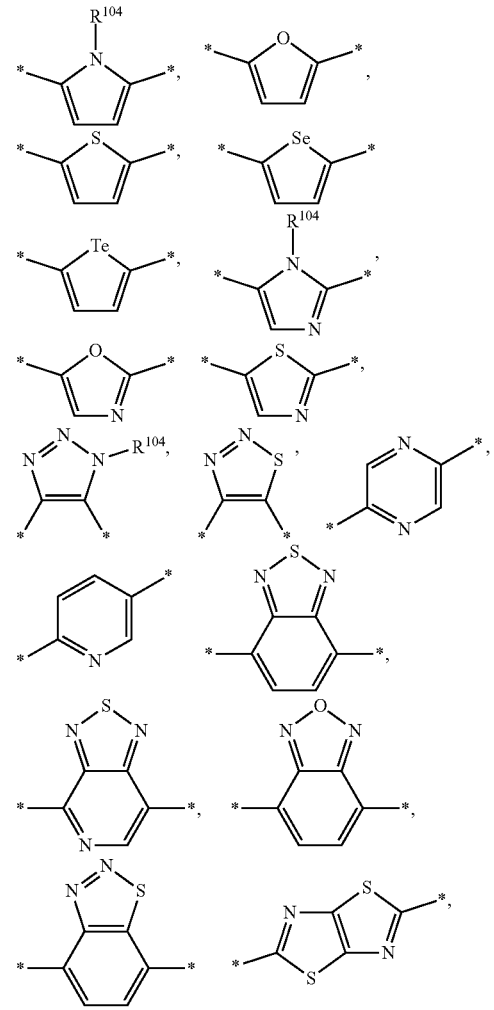

-continued
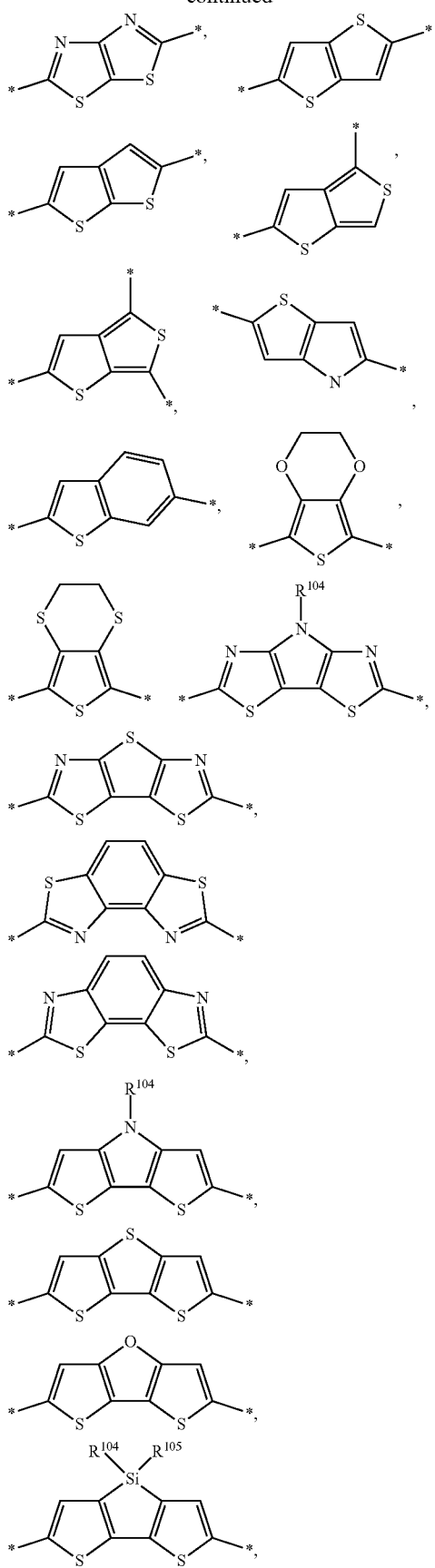
-continued
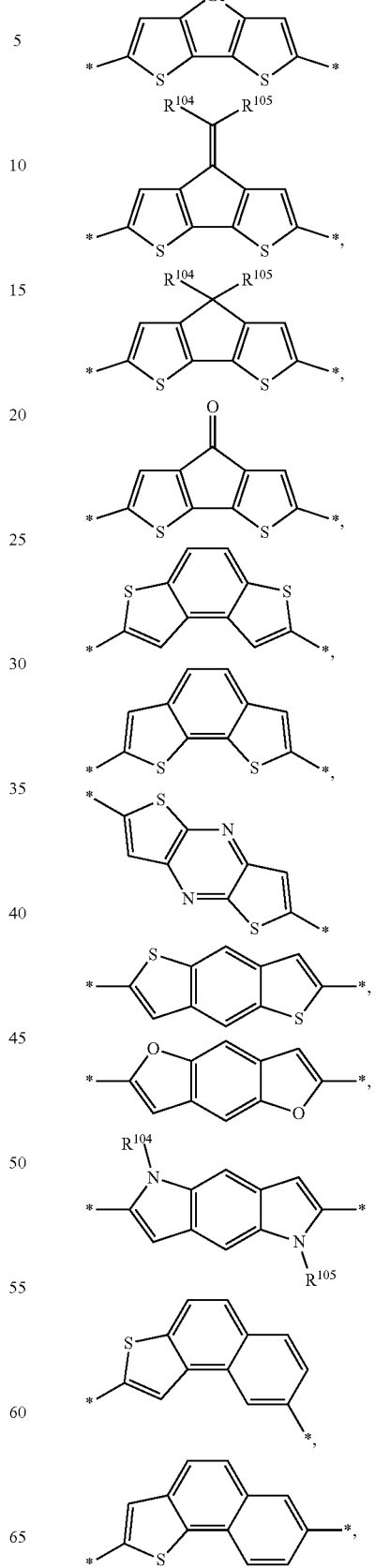

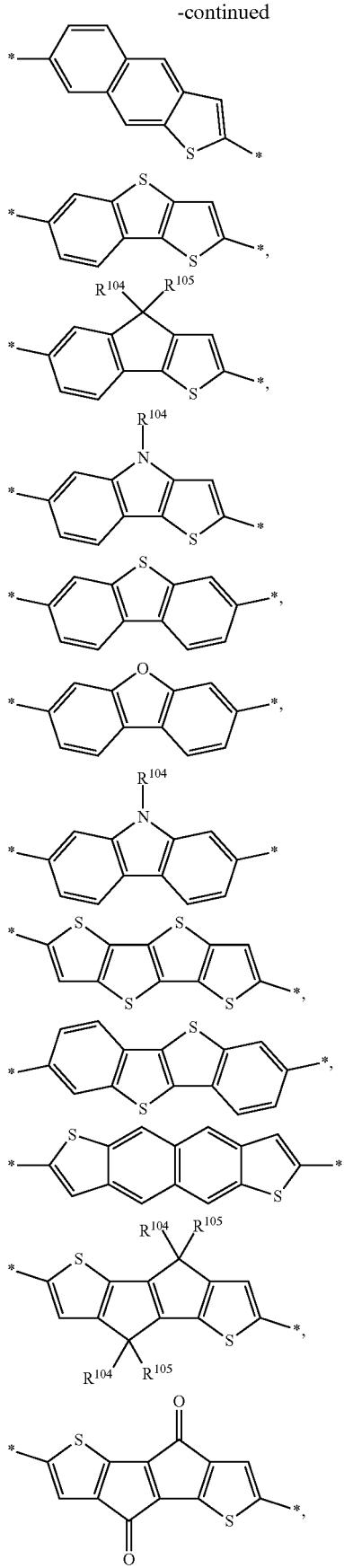
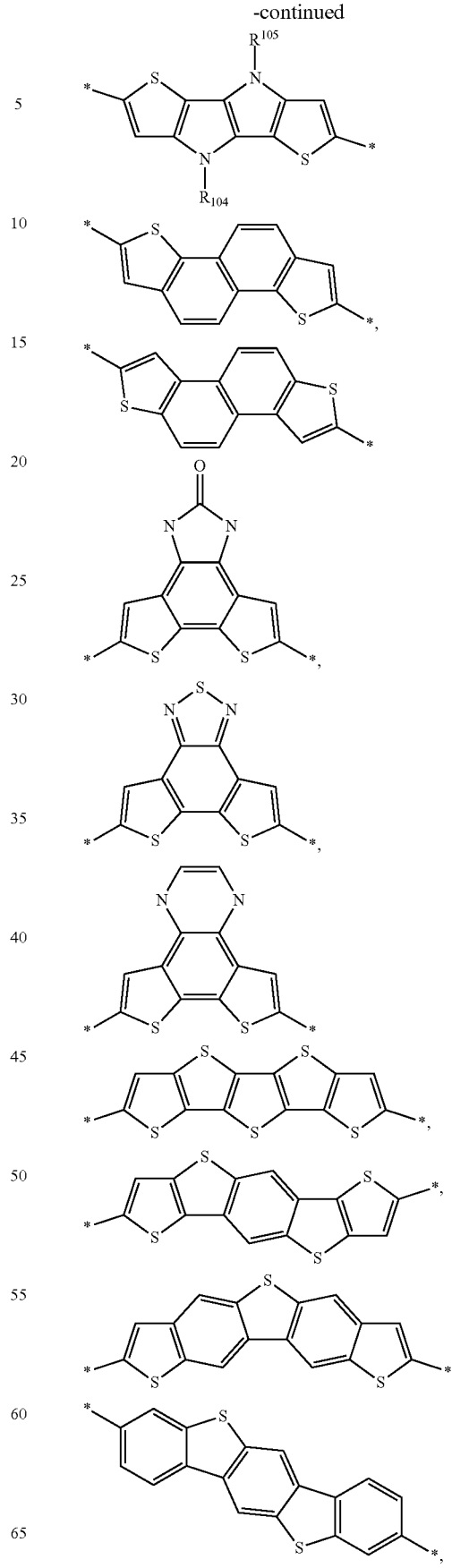

25
-continued
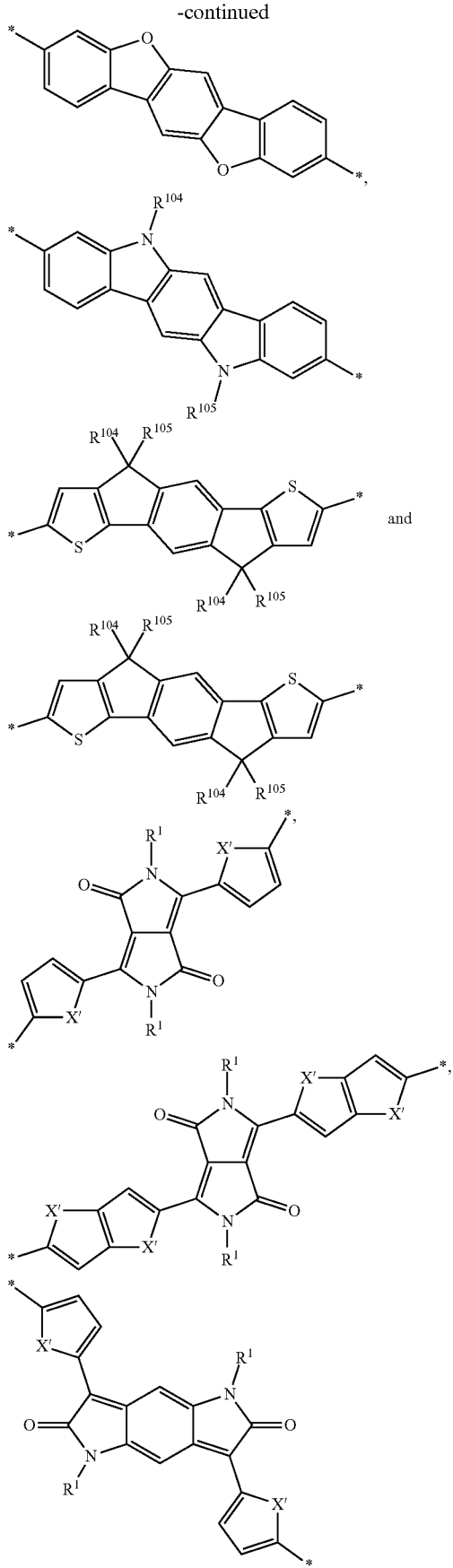
and
26
-continued
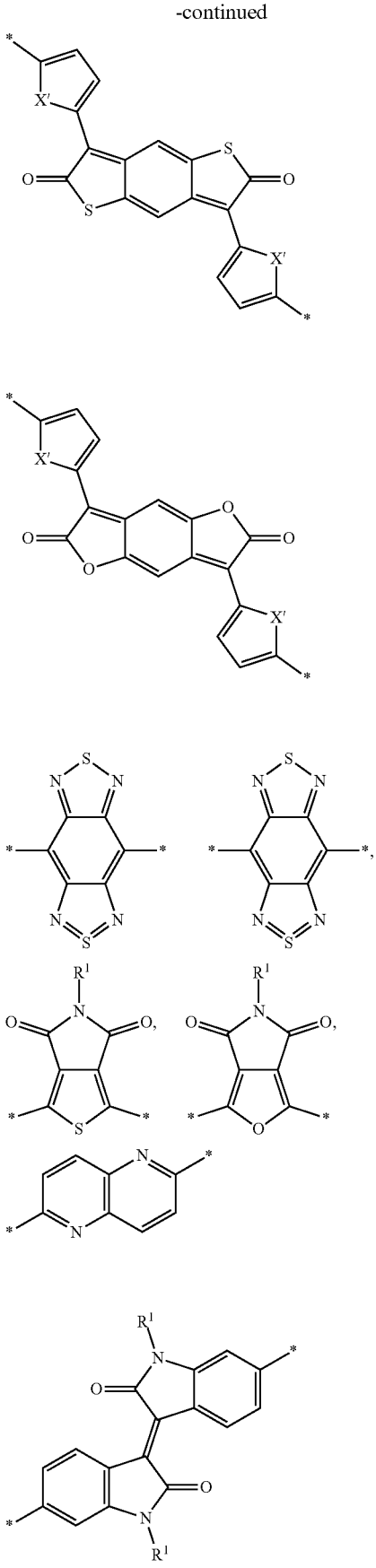

-continued

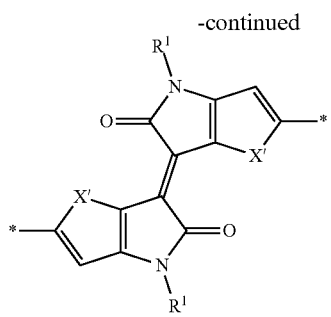

wherein
R¹ is defined as above
X' is at each occurrence selected from the group consisting of O, S, Se or Te, preferably O, S or Se, more preferably S or Se, most preferably S;
$R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system,
wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
wherein
$R^s$ and $R^t$ are independently selected from the group consisting of H, $C_{1-10}$-alkyl, $C_{2-10}$-alkenyl and $C_{2-10}$-alkynyl,
wherein
$C_{1-10}$-alkyl, $C_{2-10}$-alkenyl and $C_{2-10}$-alkynyl can be substituted with one to five substituents selected from the group consisting of halogen, CN and $NO_2$.

The 5 to 12 membered ring system can contain, in addition to the atom, to which $R^{100}$ and $R^{101}$, respectively $R^{102}$ and $R^{103}$, respectively $R^{104}$ and $R^{105}$, are attached, ring members selected from the group consisting of $CH_2$, O, S and $NR^u$, wherein $R^u$ is at each occurrence selected from the group consisting of H, $C_{1-10}$-alkyl, $C_{2-10}$-alkenyl and $C_{2-10}$-alkynyl.

Preferred are moieties of formulae 1, 1', 2 and 2', where M1 and M2 enable an electronically conjugated link between $L_1$ and $L_2$.

Preferred are polymers comprising at least one unit of formulae

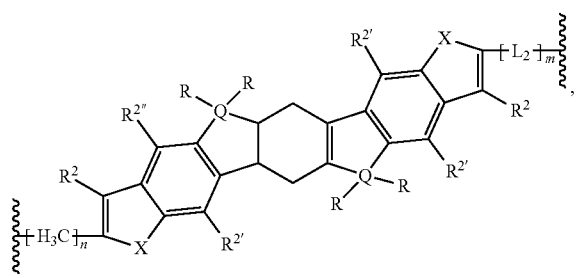

1a

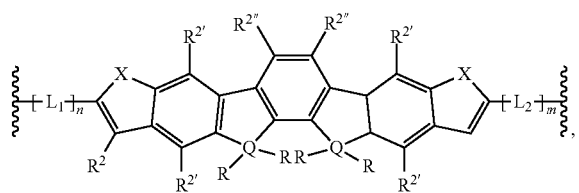

1b

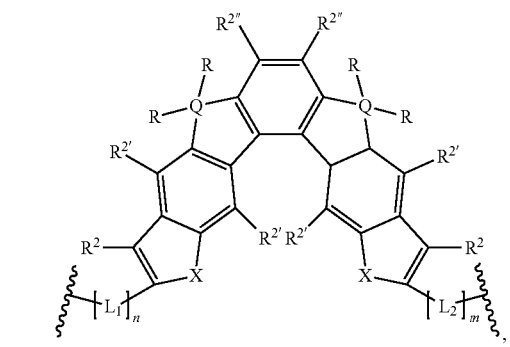

1c

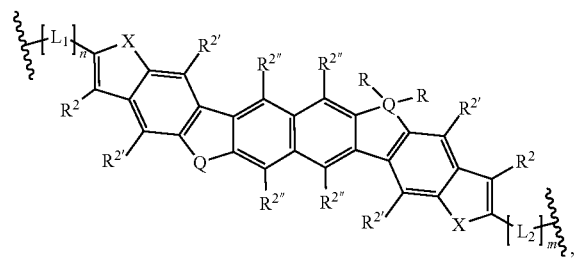

1d

-continued

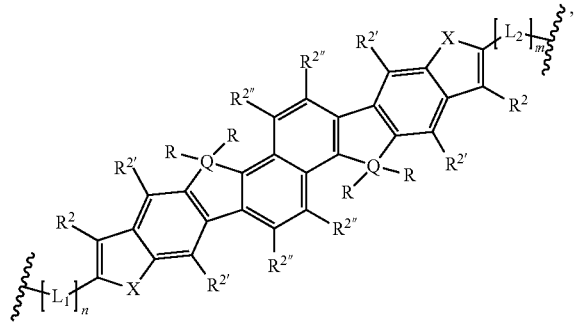

1e

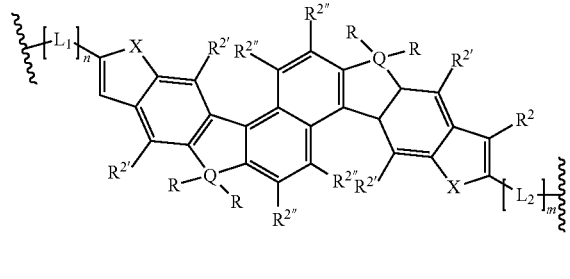

1f

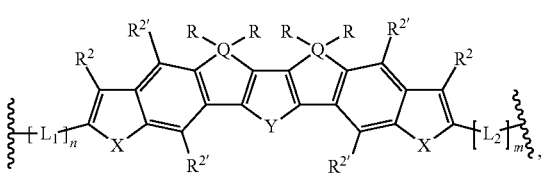

1g

1h n, m, L1, L2, X, Q, R, $R^2$, $R^{2'}$, $R^{2''}$ are defined as above;

Y is at each occurrence selected from the group consisting of O, S, Se or Te, preferably O, S or Se, more preferably S or Se, most preferably S;

More preferred are polymers comprising at least one unit of formula 1a, 1b, 1d, 1e, or 1f, where n, m, L1, L2, X, Q, R, $R^2$, $R^{2'}$, $R^{2''}$ are defined as above;

Even more preferred are polymers comprising at least one unit of formula

1a

1b

1f where n, m, L1, L2, X, Q, R, $R^2$, $R^{2'}$, $R^{2''}$ are defined as above;

Still more preferred are polymers comprising at least one unit of formula

1a

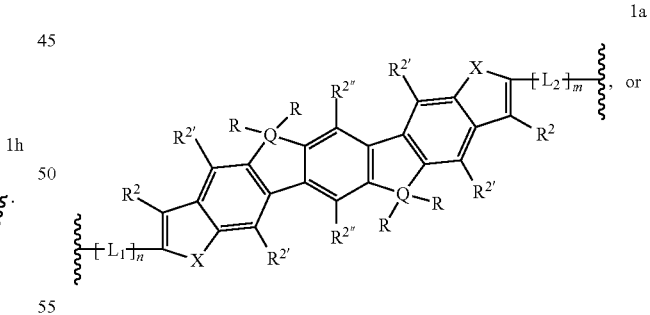

1b

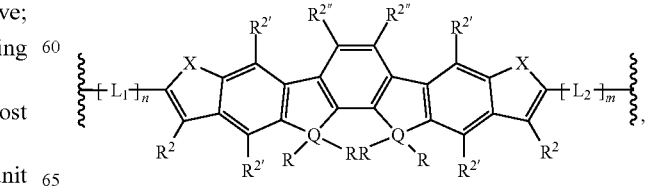

where n, m, L1, L2, X, Q, R, $R^2$, $R^{2'}$, $R^{2''}$ are defined as above;

Most preferred are polymers comprising at least one unit of formula

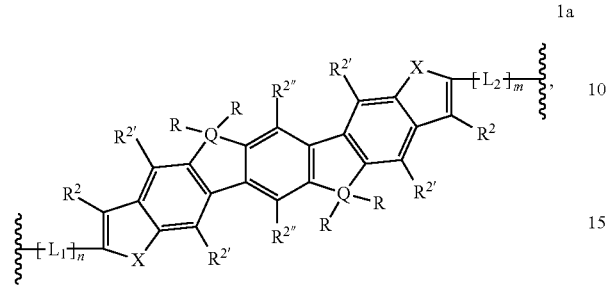

1a where n, m, L1, L2, X, Q, $R^2$, $R^2$, $R^2$ are defined as above;

Preferably, the polymers of the present invention comprise at least 60% by weight of units of formulae (1) or (1') based on the weight of the polymer.

More preferably, the polymers of the present invention comprise at least 80% by weight of units of formulae (1) or (1') based on the weight of the polymer.

Most preferably, the polymers of the present invention essentially consist of units of formulae (1) or (1').

Preferably, R and $R^1$ are at each occurrence selected from the group consisting of H, $C_{1-100}$-alkyl, $C_{2-100}$-alkenyl, $C_{2-100}$-alkynyl, $C_{5-12}$-cycloalkyl, $C_{6-18}$-aryl, and a 5 to 20 membered heteroaryl,
wherein
$C_{1-10}$-alkyl, $C_{2-100}$-alkenyl and $C_{2-100}$-alkynyl can be substituted with one to forty substituents independently selected from the group consisting of $C_{5-8}$-cycloalkyl, $C_{6-14}$-aryl, 5 to 14 membered heteroaryl, $OR^a$, $OC(O)-R^a$, $C(O)-OR^a$, $C(O)-R^a$, $NR^a-C(O)R^b$, $C(O)-NR^aR^b$, $SR^a$, $Si(R^{Sia})(R^{Sib})(R^{Sic})$, $-O-Si(R^{Sia})(R^{Sib})(R^{Sic})$, halogen and CN; and at least two $CH_2$-groups, but not adjacent $CH_2$-groups, of $C_{1-100}$-alkyl, $C_{2-100}$-alkenyl and $C_{2-100}$-alkynyl can be replaced by O or S, $C_{5-12}$-cycloalkyl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)-R^a$, $C(O)-OR^a$, $C(O)-R^a$, $NR^a-C(O)R^b$, $C(O)-NR^aR^b$, $SR^a$, $Si(R^{Sia})(R^{Sib})(R^{Sic})$, $-O-Si(R^{Sia})(R^{Sib})(R^{Sic})$, halogen, and CN; and one or two $CH_2$-groups, but not adjacent $CH_2$-groups, of $C_{5-12}$-cycloalkyl can be replaced by O, S, OC(O), CO, $NR^a$ or $NR^a-CO$, $C_{6-18}$-aryl and 5 to 20 membered heteroaryl can be substituted with one to six substituents independently selected from the group consisting of $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $OR^a$, $OC(O)-R^a$, $C(O)-OR^a$, $C(O)-R^a$, $NR^a-C(O)R^b$, $C(O)-NR^aR^b$, $SR^a$, $Si(R^{Sia})(R^{Sib})(R^{Sic})$, $-O-Si(R^{Sia})(R^{Sib})(R^{Sic})$, halogen, and CN,
wherein
$R^a$ and $R^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, 5 to 14 membered heteroaryl, $O-C_{1-60}$-alkyl, $O-C_{2-60}$-alkenyl, $O-C_{2-60}$-alkynyl, $O-C_{5-8}$-cycloalkyl, $-[O-SiR^{Sid}R^{Sie}]_o-R^{Sif}$,
wherein
o is an integer from 1 to 50,
$R^{Sid}$, $R^{Sie}$ and $R^{Sif}$ are independently selected from the group consisting of H,
$C_{1-60}$-alkyl, $C_{2-60}$-alkenyl, $C_{2-60}$-alkynyl, $C_{5-8}$-cycloalkyl, $C_{6-14}$-aryl, $-[O-SiR^{Sig}R^{Sih}]_p-R^{Sii}$,
wherein
p is an integer from 1 to 50,
$R^{Sig}R^{Sih}$ and $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, $O-Si(CH_3)_3$, $C_{1-60}$-alkyl, $C_{2-60}$-alkenyl and $C_{2-60}$-alkynyl can be substituted with one to twenty substituents selected from the group consisting of $C_{5-6}$-cycloalkyl, $C_{6-10}$-aryl, $OR^c$, $OC(O)-R^c$, $C(O)-OR^c$, $C(O)-R^c$, $NR^c-C(O)R^d$, $C(O)-NR^cR^d$, $SR^c$, $Si(R^{Sij})(R^{Sik})(R^{Sil})$, $-O-Si(R^{Sij})(R^{Sik})(R^{Sil})$, halogen, and CN; and at least two $CH_2$-groups, but not adjacent $CH_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, $OR^c$, $OC(O)-R^c$, $C(O)-OR^c$, $C(O)-R^c$, $NR^c-C(O)R^d$, $C(O)-NR^cR^d$, $SR^c$, $Si(R^{Sij})(R^{Sik})(R^{Sil})$, $-O-Si(R^{Sij})(R^{Sik})(R^{Sil})$, halogen, and CN; and one or two $CH_2$-groups, but not adjacent $CH_2$-groups, of $C_{5-8}$-cycloalkyl can be replaced by O, S, OC(O), CO, $NR^c$ or $NR^c-CO$, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, $OR^c$, $OC(O)-R^c$, $C(O)-OR^c$, $C(O)-R^c$, $NR^c-C(O)R^d$, $C(O)-NR^cR^d$, $SR^c$, $Si(R^{Sij})(R^{Sik})(R^{Sil})$, $-O-Si(R^{Sij})(R^{Sik})(R^{Sil})$, halogen and CN;
wherein
$R^c$ and $R^d$ are independently selected from the group consisting of H, $C_{1-30}$-alkyl, $C_{2-30}$-alkenyl and $C_{2-30}$-alkynyl,
$R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, $-[O-SiR^{Sim}R^{Sin}]_q-R^{Sio}$,
wherein
q is an integer from 1 to 50,
$R^{Sim}$, $R^{Sin}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, $O-C_{1-30}$-alkyl, $O-C_{2-30}$-alkenyl, $O-C_{2-30}$-alkynyl, $O-C_{5-6}$-cycloalkyl, $O-C_{6-10}$-aryl, O-5 to 10 membered heteroaryl, $-[O-SiR^{Sip}R^{Siq}]_r-R^{Sir}$, $NR^{70}R^{80}$, halogen, and $O-C(O)-R^{70}$;

wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, 5 to 10 membered heteroaryl, O—$C_{1-30}$-alkyl, O—$C_{2-30}$-alkenyl, O—$C_{2-30}$-alkynyl, O—$C_{5-6}$-cycloalkyl, O—$C_{6-10}$-aryl, O-5 to 10 membered heteroaryl, O—Si(CH$_3$)$_3$, NR$^{700}$R$^{800}$, halogen and O—C(O)—R$^{700}$, $R^{70}$, $R^{80}$, $R^{700}$ and $R^{800}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, and 5 to 10 membered heteroaryl, $C_{1-30}$-alkyl, $C_{2-30}$-alkenyl and $C_{2-30}$-alkynyl can be substituted with one to ten substituents selected from the group consisting of halogen and CN.

More preferably, R and $R^1$ are at each occurrence selected from the group consisting of $C_{1-100}$-alkyl, $C_{2-100}$-alkenyl and $C_{2-100}$-alkynyl, wherein $C_{1-100}$-alkyl, $C_{2-100}$-alkenyl and $C_{2-100}$-alkynyl can be substituted with one to forty substituents independently selected from the group consisting of $C_{5-8}$-cycloalkyl, $C_{6-14}$-aryl, 5 to 14 membered heteroaryl, OR$^a$, OC(O)—R$^a$, C(O)—OR$^a$, C(O)—R$^a$, NR$^a$—C(O)R$^b$, C(O)—NR$^a$R$^b$, SR$^a$, Si(R$^{Sia}$)(R$^{Sib}$)(R$^{Sic}$), —O—Si(R$^{Sia}$)(R$^{Sib}$)(R$^{Sic}$), halogen, and CN; and at least two CH$_2$-groups, but not adjacent CH$_2$-groups, of $C_{1-100}$-alkyl, $C_{2-100}$-alkenyl and $C_{2-100}$-alkynyl can be replaced by O or S, wherein $R^a$ and $R^b$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl and 5 to 14 membered heteroaryl, $R^{Sia}$, $R^{Sib}$ and $R^{Sic}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, —[O—SiR$^{Sid}$R$^{Sie}$]$_o$—R$^{Sif}$, wherein o is an integer from 1 to 50, $R^{Sid}$, $R^{Sie}$ and $R^{Sif}$ are independently selected from the group consisting of H, $C_{1-60}$-alkyl, $C_{2-60}$-alkenyl, $C_{2-60}$-alkynyl, $C_{5-8}$-cycloalkyl, $C_{6-14}$-aryl, —[O—SiR$^{Sig}$R$^{Sih}$]$_p$—R$^{Sii}$, wherein p is an integer from 1 to 50, $R^{Sig}$, $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—Si(CH$_3$)$_3$, $C_{1-60}$-alkyl, $C_{2-60}$-alkenyl and $C_{2-60}$-alkynyl can be substituted with one to twenty substituents selected from the group consisting of $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$), halogen, and CN; and at least two CH$_2$-groups, but not adjacent CH$_2$-groups, of $C_{1-60}$-alkyl, $C_{2-60}$-alkenyl and $C_{2-60}$-alkynyl can be replaced by O or S, $C_{5-8}$-cycloalkyl can be substituted with one to five substituents selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$), halogen, and CN; and one or two CH$_2$-groups, but not adjacent CH$_2$-groups, of $C_{5-8}$-cycloalkyl can be replaced by O, S, OC(O), CO, NR$^c$ or NR$^c$—CO, $C_{6-14}$-aryl and 5 to 14 membered heteroaryl can be substituted with one to five substituents independently selected from the group consisting of $C_{1-30}$-alkyl, $C_{2-30}$-alkenyl, $C_{2-30}$-alkynyl, $C_{5-6}$-cycloalkyl, $C_{6-10}$-aryl, OR$^c$, OC(O)—R$^c$, C(O)—OR$^c$, C(O)—R$^c$, NR$^c$—C(O)R$^d$, C(O)—NR$^c$R$^d$, SR$^c$, Si(R$^{Sij}$)(R$^{Sik}$)(R$^{Sil}$), —O—Si(R$^{Sij}$)(R$^{Sik}$)(R$^{Sil}$), halogen, and CN;

wherein $R^c$ and $R^d$ are independently selected from the group consisting of H, $C_{1-30}$-alkyl, $C_{2-30}$-alkenyl and $C_{2-30}$-alkynyl, $R^{Sij}$, $R^{Sik}$ and $R^{Sil}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—SiR$^{Sim}$R$^{Sin}$]$_q$—R$^{Sio}$, wherein q is an integer from 1 to 50, $R^{Sim}$, $R^{Sin}$, $R^{Sio}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—SiR$^{Sip}$R$^{Siq}$]$_r$—R$^{Sir}$, wherein r is an integer from 1 to 50, $R^{Sip}$, $R^{Siq}$, $R^{Sir}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—Si(CH$_3$)$_3$, $C_{1-30}$-alkyl, $C_{2-30}$-alkenyl and $C_{2-30}$-alkynyl can be substituted with one to ten substituents selected from the group consisting of halogen and CN.

Even more preferably, R and $R^1$ are at each occurrence selected from the group consisting of $C_{1-50}$-alkyl, $C_{2-50}$-alkenyl and $C_{2-50}$-alkynyl, wherein $C_{1-50}$-alkyl, $C_{2-50}$-alkenyl and $C_{2-50}$-alkynyl can be substituted with one to twenty substituents independently selected from the group consisting of $C_{5-6}$-cycloalkyl, $C_{6-10}$-aryl, 5 to 10 membered heteroaryl, OR$^a$, SR$^a$, Si(R$^{Sia}$)(R$^{Sib}$)(R$^{Sic}$), —O—Si(R$^{Sia}$)(R$^{Sib}$)(R$^{Sic}$), halogen, and CN; and at least two CH$_2$-groups, but not adjacent CH$_2$-groups, of $C_{1-50}$-alkyl, $C_{2-50}$-alkenyl and $C_{2-50}$-alkynyl can be replaced by O or S, wherein $R^a$ is independently selected from the group consisting of H, $C_{1-30}$-alkyl, $C_{2-30}$-alkenyl, $C_{2-30}$-alkynyl, $C_{5-6}$-cycloalkyl and $C_{6-10}$-aryl, $R^{Sia}$, $R^{Sib}$ and $R^{Sic}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—SiR$^{Sid}$R$^{Sie}$]$_o$—R$^{Sif}$, wherein o is an integer from 1 to 50, $R^{Sid}$, $R^{Sie}$, $R^{Sif}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, —[O—SiR$^{Sig}$R$^{Sih}$]$_p$—R$^{Sii}$, wherein p is an integer from 1 to 50, $R^{Sig}$, $R^{Sih}$, $R^{Sii}$ are independently selected from the group consisting of H, $C_{1-30}$-alkyl, $C_{2-30}$-alkenyl, $C_{2-30}$-alkynyl, $C_{5-6}$-cycloalkyl, $C_{6-10}$-aryl, O—Si(CH$_3$)$_3$, $C_{1-30}$-alkyl, $C_{2-30}$-alkenyl and $C_{2-30}$-alkynyl can be substituted with one to ten substituents selected from the group consisting of halogen and CN.

Still more preferably, R and R$^1$ are at each occurrence selected from the group consisting of $C_{1-50}$-alkyl, $C_{3-50}$-alkenyl and $C_{3-50}$-alkynyl, wherein $C_{1-50}$-alkyl, $C_{3-50}$-alkenyl and $C_{3-50}$-alkynyl can be substituted with one to twenty substituents independently selected from the group consisting of $C_{5-6}$-cycloalkyl, $C_{6-10}$-aryl, 5 to 10 membered heteroaryl, OR$^a$, SR$^a$, Si(R$^{Sia}$)(R$^{Sib}$)(R$^{Sic}$), halogen, and CN; and at least two CH$_2$-groups, but not adjacent CH$_2$-groups, of $C_{1-36}$-alkyl, $C_{2-36}$-alkenyl and $C_{2-36}$-alkynyl can be replaced by O or S, wherein R$^a$ is independently selected from the group consisting of H, $C_{1-20}$-alkyl, $C_{3-20}$-alkenyl, $C_{3-20}$-alkynyl, $C_{5-6}$-cycloalkyl and $C_{6-10}$-aryl R$^{Sia}$, R$^{Sib}$ and R$^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, —[O—SiR$^{Sid}$R$^{Sie}$]$_o$—R$^{Sif}$ wherein o is an integer from 1 to 50, R$^{Sid}$, R$^{Sie}$, R$^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, —[O—SiR$^{Sig}$R$^{Sih}$]$_p$—R$^{Sii}$, wherein p is an integer from 1 to 50, $R^{Sig}$, $R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, O—Si(CH$_3$)$_3$, $C_{1-20}$-alkyl, $C_{2-20}$-alkenyl and $C_{2-20}$-alkynyl can be substituted with one to ten substituents selected from the group consisting of halogen and CN.

Most preferably, R and R$^1$ are at each occurrence selected from the group consisting of $C_{1-50}$-alkyl, $C_{3-50}$-alkenyl and $C_{3-50}$-alkynyl, wherein $C_{1-50}$-alkyl, $C_{3-50}$-alkenyl and $C_{3-50}$-alkynyl can be substituted with one to ten substituents independently selected from the group consisting of OR$^a$, SR$^a$, Si(R$^{Sia}$)(R$^{Sib}$)(R$^{Sic}$), and halogen; and at least two CH$_2$-groups, but not adjacent CH$_2$-groups, of $C_{1-50}$-alkyl, $C_{3-50}$-alkenyl and $C_{3-50}$-alkynyl can be replaced by O or S, wherein R$^a$ is independently selected from the group consisting of H, $C_{1-20}$-alkyl, $C_{3-20}$-alkenyl, $C_{3-20}$-alkynyl, $C_{5-6}$-cycloalkyl and $C_{6-10}$-aryl R$^{Sia}$, R$^{Sib}$ and R$^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, —[O—SiR$^{Sid}$R$^{Sie}$]$_o$—R$^{Sif}$ wherein o is an integer from 1 to 50, R$^{Sid}$, R$^{Sie}$, R$^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, —[O—SiR$^{Sig}$R$^{Sih}$]$_p$—R$^{Sii}$;

wherein p is an integer from 1 to 50, $R^{Sig}$, $R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, O—Si(CH$_3$)$_3$, $C_{1-20}$-alkyl, $C_{2-20}$-alkenyl and $C_{2-20}$-alkynyl can be substituted with one to ten substituents selected from the group consisting of halogen and CN.

Especially preferably, R and R$^1$ are at each occurrence selected from the group consisting of $C_{1-50}$-alkyl, $C_{3-50}$-alkenyl and $C_{3-50}$-alkynyl, wherein $C_{1-50}$-alkyl, $C_{3-50}$-alkenyl and $C_{3-50}$-alkynyl can be substituted with one to ten fluorine groups; and at least two CH$_2$-groups, but not adjacent CH$_2$-groups, of $C_{1-50}$-alkyl, $C_{3-50}$-alkenyl and $C_{3-50}$-alkynyl can be replaced by O or S.

In particular, R and R$^1$ are at each occurrence unsubstituted $C_{1-50}$-alkyl, $C_{3-50}$-alkenyl and $C_{3-50}$-alkynyl, especially $C_{1-36}$-alkyl, more especially $C_{8-36}$-alkyl.

Preferably, R$^2$, R$^{2'}$, R$^{2''}$ and R* are at each occurrence selected from the group consisting of hydrogen, $C_{1-30}$-alkyl, and halogen, wherein $C_{1-30}$-alkyl can be substituted with one to ten substituents independently selected from the group consisting of $C_{5-8}$-cycloalkyl, $C_{6-14}$-aryl, 5 to 14 membered heteroaryl, OR$^e$, OC(O)—R$^e$, C(O)—OR$^e$, C(O)—R$^e$, NR$^e$R$^f$, NR$^e$—C(O)R$^f$, C(O)—NR$^e$R$^f$, N[C(O)R$^e$][C(O)R$^f$], SR$^e$, halogen, CN, SiR$^{Sis}$R$^{Sit}$R$^{Siu}$ and NO$_2$; and at least two CH$_2$-groups, but not adjacent CH$_2$-groups, of $C_{1-30}$-alkyl can be replaced by O or S, wherein R$^{Sis}$, R$^{Sit}$ and R$^{Siu}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—Si(CH$_3$)$_3$, R$^e$ and R$^f$ are independently selected from the group consisting of H, $C_{1-20}$-alkyl, $C_{3-20}$-alkenyl, $C_{3-20}$-alkynyl, $C_{5-8}$-cycloalkyl, $C_{6-14}$-aryl, and 5 to 14 membered heteroaryl, wherein $C_{1-20}$-alkyl, $C_{3-20}$-alkenyl and $C_{3-20}$-alkynyl can be substituted with one to five substituents selected from the group consisting of $C_{5-6}$-cycloalkyl, $C_{6-10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;

$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;

$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, OR$^g$, OC(O)—R$^g$, C(O)—OR$^g$, C(O)—R$^g$, NR$^g$R$^h$, NR$^g$—C(O)R$^h$, C(O)—NR$^g$R$^h$, N[C(O)R$^g$][C(O)R$^h$], SR$^g$, halogen, CN, and NO$_2$;

wherein

R$^g$ and R$^h$ are independently selected from the group consisting of H, C$_{1-10}$-alkyl, C$_{3-10}$-alkenyl and C$_{3-10}$-alkynyl, wherein C$_{1-10}$-alkyl, C$_{3-10}$-alkenyl and C$_{3-10}$-alkynyl can be substituted with one to five substituents selected from the group consisting of halogen, CN and NO$_2$.

More preferably, R$^2$, R$^{2'}$, R$^{2''}$ and R* are at each occurrence selected from the group consisting of hydrogen, unsubstituted C$_{1-30}$-alkyl and halogen.

In particular, R$^2$, R$^{2'}$, R$^{2''}$ and R* are in each occurrence hydrogen.

Preferably, n is 0, 1 or 2. More preferably, n is 0 or 1. Most preferably, n is 0.

Preferably, m is 0, 1 or 2.

In some embodiments, L$^1$ and L$^2$ are independently from each other and at each occurrence preferably selected from the group consisting of C$_{6-30}$-arylene, 5 to 30 membered heteroarylene, and

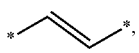

wherein

C$_{6-30}$-arylene and 5 to 30 membered heteroarylene can be substituted with one to six substituents R$^3$ at each occurrence selected from the group consisting of C$_{1-30}$-alkyl, C$_{2-30}$-alkenyl, C$_{2-30}$-alkynyl, C$_{5-12}$-cycloalkyl, C$_{6-18}$-aryl and 5 to 20 membered heteroaryl, OR$^{31}$, OC(O)—R$^{31}$, C(O)—OR$^{31}$, C(O)—R$^{31}$, NR$^{31}$R$^{32}$, NR$^{31}$—C(O)R$^{32}$, C(O)—NR$^{31}$R$^{32}$, SR$^{31}$, halogen, CN, SiR$^{Siv}$R$^{Siw}$R$^{Six}$ and OH, and wherein

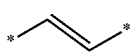

can be substituted with one or two substituents R$^4$ at each occurrence selected from the group consisting of C$_{1-30}$-alkyl, C$_{2-30}$-alkenyl, C$_{2-30}$-alkynyl, C$_{5-12}$-cycloalkyl, C$_{6-18}$-aryl and 5 to 20 membered heteroaryl, C(O)—R$^{41}$, C(O)—NR$^{41}$R$^{42}$, C(O)—OR$^{41}$ and CN, wherein R$^{31}$, R$^{32}$, R$^{41}$ und R$^{42}$ are independently from each other and at each occurrence selected from the group consisting of H, C$_{1-30}$-alkyl, C$_{2-30}$-alkenyl, C$_{2-30}$-alkynyl, C$_{5-12}$-cycloalkyl, C$_{6-18}$-aryl and 5 to 20 membered heteroaryl, and wherein C$_{1-30}$-alkyl, C$_{2-30}$-alkenyl and C$_{2-30}$-alkynyl can be substituted with one to ten substituents independently selected from the group consisting of C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, SiR$^{Siv}$R$^{Siw}$R$^{Six}$ and NO$_2$; and at least two CH$_2$-groups, but not adjacent CH$_2$-groups of C$_{1-30}$-alkyl, C$_{2-30}$-alkenyl and C$_{2-30}$-alkynyl can be replaced by O or S, C$_{5-12}$-cycloalkyl can be substituted with one to six substituents independently selected from the group consisting of C$_{1-20}$-alkyl, C$_{2-20}$-alkenyl and C$_{2-20}$-alkynyl, C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, SiR$^{Siv}$R$^{Siw}$R$^{Six}$ and NO$_2$; and one or two CH$_2$-groups, but not adjacent CH$_2$-groups, of C$_{5-12}$-cycloalkyl can be replaced by O, S, OC(O), CO, NR$^i$ or NR$^i$—CO, C$_{6-18}$-aryl and 5 to 20 membered heteroaryl can be substituted with one to six substituents independently selected from the group consisting of C$_{1-20}$-alkyl, C$_{2-20}$-alkenyl, C$_{2-20}$-alkynyl, C$_{5-8}$-cycloalkyl, C$_{6-14}$-aryl, 5 to 14 membered heteroaryl, OR$^i$, OC(O)—R$^j$, C(O)—OR$^i$, C(O)—R$^i$, NR$^i$R$^j$, NR$^i$—C(O)R$^j$, C(O)—NR$^i$R$^j$, N[C(O)R$^i$][C(O)R$^j$], SR$^i$, halogen, CN, SiR$^{Siv}$R$^{Siw}$R$^{Six}$ and NO$_2$, wherein R$^{Siv}$, R$^{Siw}$, R$^{Six}$ are independently from each other selected from the group consisting of H, C$_{1-20}$-alkyl, C$_{2-20}$-alkenyl, C$_{2-20}$-alkynyl, C$_{5-6}$-cycloalkyl, phenyl and O—Si(CH$_3$)$_3$, R$^i$ and R$^j$ are independently selected from the group consisting of H, C$_{1-20}$-alkyl, C$_{3-20}$-alkenyl, C$_{3-20}$-alkynyl, C$_{5-8}$-cycloalkyl, C$_{6-14}$-aryl, and 5 to 14 membered heteroaryl, wherein C$_{1-20}$-alkyl, C$_{3-20}$-alkenyl and C$_{3-20}$-alkynyl can be substituted with one to five substituents selected from the group consisting of C$_{5-6}$-cycloalkyl, C$_{6-10}$-aryl, 5 to 10 membered heteroaryl, OR$^k$, OC(O)—R$^l$, C(O)—OR$^k$, C(O)—R$^k$, NR$^k$R$^l$, NR$^k$—C(O)R$^l$, C(O)—NR$^k$R$^l$, N[C(O)R$^k$][C(O)R$^l$], SR$^k$, halogen, CN, and NO$_2$;

C$_{5-8}$-cycloalkyl can be substituted with one to five substituents selected from the group consisting of C$_{1-10}$-alkyl, C$_{2-10}$-alkenyl, C$_{2-10}$-alkynyl, C$_{5-6}$-cycloalkyl, C$_{6-10}$-aryl, 5 to 10 membered heteroaryl, OR$^k$, OC(O)—R$^l$, C(O)—OR$^k$, C(O)—R$^k$, NR$^k$R$^l$, NR$^k$—C(O)R$^l$, C(O)—NR$^k$R$^l$, N[C(O)R$^k$][C(O)R$^l$], SR$^k$, halogen, CN, and NO$_2$;

C$_{6-14}$-aryl and 5 to 14 membered heteroaryl can be substituted with one to five substituents independently selected from the group consisting of C$_{1-10}$-alkyl, C$_{2-10}$-alkenyl, C$_{2-10}$-alkynyl, C$_{5-6}$-cycloalkyl, C$_{6-10}$-aryl, 5 to 10 membered heteroaryl, OR$^k$, OC(O)—R$^l$, C(O)—OR$^k$, C(O)—R$^k$, NR$^k$R$^l$, NR$^k$—C(O)R$^l$, C(O)—NR$^k$R$^l$, N[C(O)R$^k$][C(O)R$^l$], SR$^k$, halogen, CN, and NO$_2$;

wherein

R$^k$ and R$^l$ are independently selected from the group consisting of H,

C$_{1-10}$-alkyl, C$_{3-10}$-alkenyl and C$_{3-10}$-alkynyl, wherein

C$_{1-10}$-alkyl, C$_{3-10}$-alkenyl and C$_{3-10}$-alkynyl can be substituted with one to five substituents selected from the group consisting of halogen, CN and NO$_2$, In some other embodiments, L$^1$ and L$^2$ are independently from each other and at each occurrence selected from the group consisting of C$_6$-C$_{30}$-arylene and 5 to 30 membered heteroarylene, and

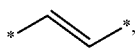

wherein $C_6$-$C_{30}$-arylene and 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)$—$R^{31}$, $C(O)$—$OR^{31}$, $C(O)$—$R^{31}$, $NR^{31}R^{32}$, $NR^{31}$—$C(O)R^{32}$, $C(O)$—$NR^{31}R^{32}$, $SR^{31}$, halogen, CN, $SiR^{Siv}R^{Siw}R^{Six}$ and OH, and wherein

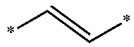 [SMILES: */C=C/*]

can be substituted with one or two substituents $R^4$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)$—$R^{41}$, $C(O)$—$NR^{41}R^{42}$, $C(O)$—$OR^{41}$ and CN, wherein $R^{31}$, $R^{32}$, $R^{41}$ und $R^{42}$ are independently from each other and at each occurrence selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, and wherein $C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$; and at least two $CH_2$-groups, but not adjacent $CH_2$-groups of $C_{1-30}$-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl can be replaced by O, S, OC(O), CO, $NR^i$ or $NR^i$—CO.

Preferably, $L^1$ and $L^2$ are independently from each other and at each occurrence selected from the group consisting of $C_{6-30}$-arylene and 5 to 30 membered heteroarylene, and

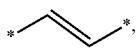

wherein $C_{6-30}$-arylene and 5 to 30 membered heteroarylene is selected from the group consisting of

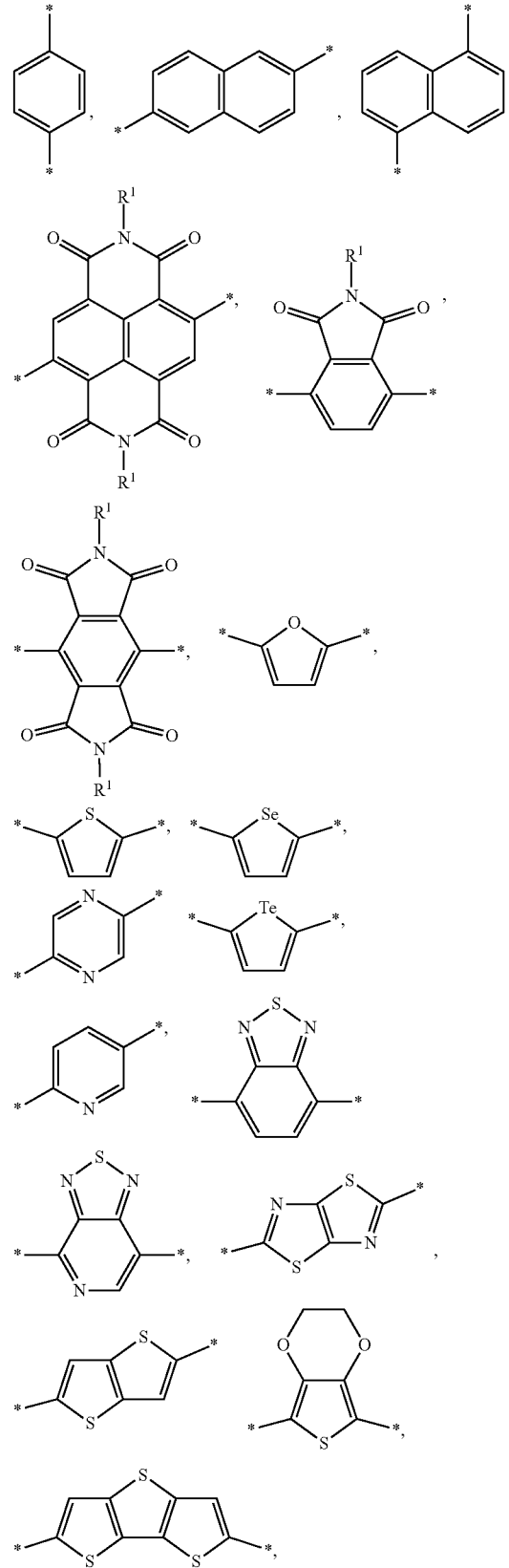

41

-continued

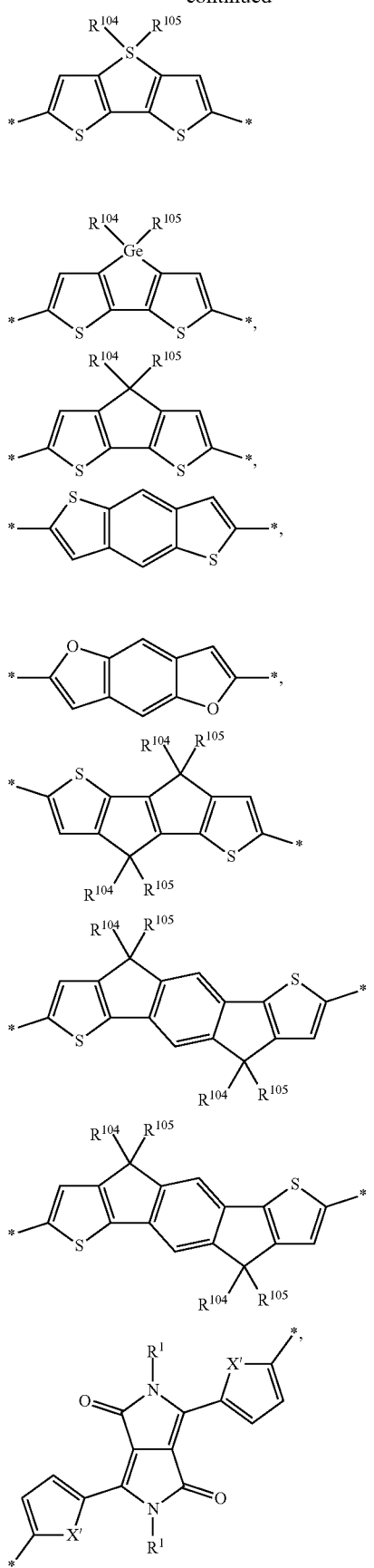

and

42

-continued

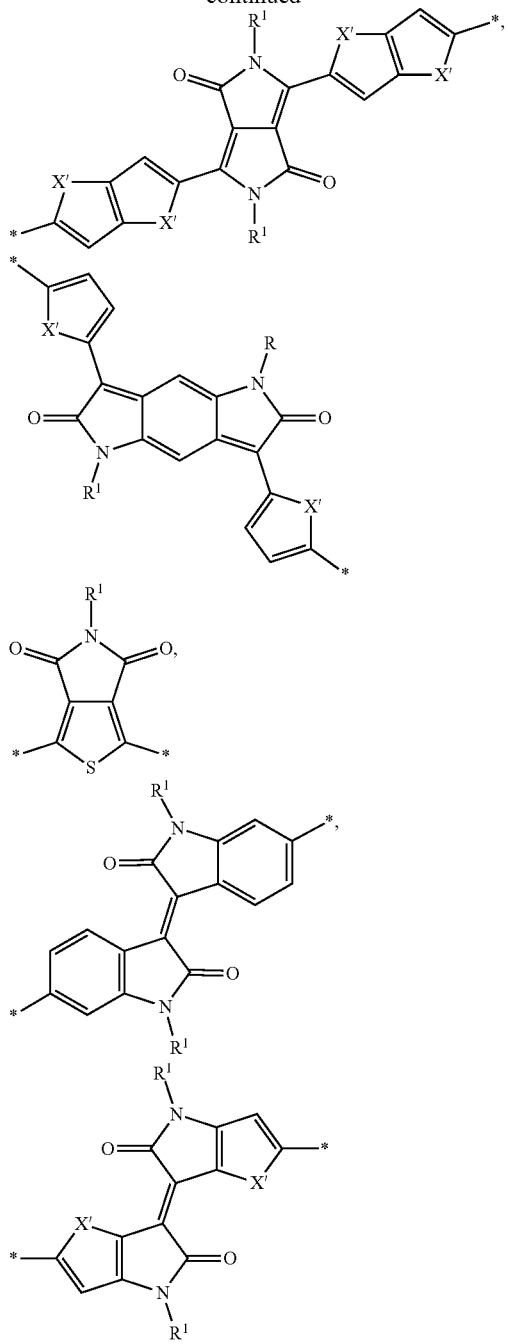

wherein
$R^{104}$ and $R^{105}$ are independently and at each occurrence selected from the group consisting of H, or $C_{1-20}$-alkyl and $C_{6-14}$-aryl,
wherein
$C_{1-20}$-alkyl can be substituted with one to five substituents selected from the group consisting of $OR^s$ and halogen;
$C_{6-14}$-aryl can be substituted with one to five substituents independently selected from the group consisting of $C_{1-10}$-alkyl, $OR^s$ and halogen;
wherein
$R^s$ is independently selected from the group consisting of H and $C_{1-10}$-alkyl, $R^1$ is at each occurrence selected from the group consisting of $C_{1-36}$-alkyl, $C_{3-36}$-alkenyl and $C_{3-36}$-alkynyl, wherein $C_{1-36}$-alkyl, $C_{3-36}$-alkenyl and $C_{3-36}$-alkynyl can be substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{Sia})(R^{Sib})(R^{Sic})$, —O—$Si(R^{Sia})(R^{Sib})(R^{Sic})$, halogen, and CN; and at least two $CH_2$-groups, but not adjacent $CH_2$-groups, of $C_{1-36}$-alkyl, $C_{2-36}$-alkenyl and $C_{2-36}$-alkynyl can be replaced by O or S, wherein $R^a$ is independently selected from the group consisting of H, $C_{1-20}$-alkyl, $C_{3-20}$-alkenyl, $C_{3-20}$-alkynyl, $C_{5-6}$-cycloalkyl and $C_{6-10}$-aryl $R^{Sia}$, $R^{Sib}$ and $R^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, —[O—$SiR^{Sid}R^{Sie}]_o$—$R^{Sif}$ wherein o is an integer from 1 to 50, $R^{Sid}$, $R^{Sie}$, $R^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, —[O—$SiR^{Sig}R^{Sih}]_p$—$R^{Sii}$, wherein p is an integer from 1 to 50, $R^{Sig}$, $R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, O—Si$(CH_3)_3$, $C_{1-20}$-alkyl, $C_{2-20}$-alkenyl and $C_{2-20}$-alkynyl can be substituted with one to ten substituents selected from the group consisting of halogen and CN.

wherein $C_{6-30}$-arylene and 5 to 30 membered heteroarylene can be substituted with one to six substituents $R^3$ at each occurrence selected from the group consisting of $C_{1-30}$-alkyl, $C_{1-30}$-alkoxy, CN and halogen, and wherein

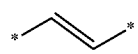

can be substituted with one or two substituents $R^4$ at each occurrence selected from the group consisting of $C_{1-30}$-alkyl, $C(O)$—$R^{41}$, $C(O)$—$OR^{41}$ and CN, wherein $R^{41}$ is at each occurrence $C_{1-30}$-alkyl.

More preferably, $L^1$ and $L^z$ are independently from each other and at each occurrence $C_{6-30}$-arylene and 5 to 30 membered heteroarylene and

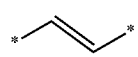

wherein $C_{6-30}$-arylene and 5 to 30 membered heteroarylene is selected from the group consisting of

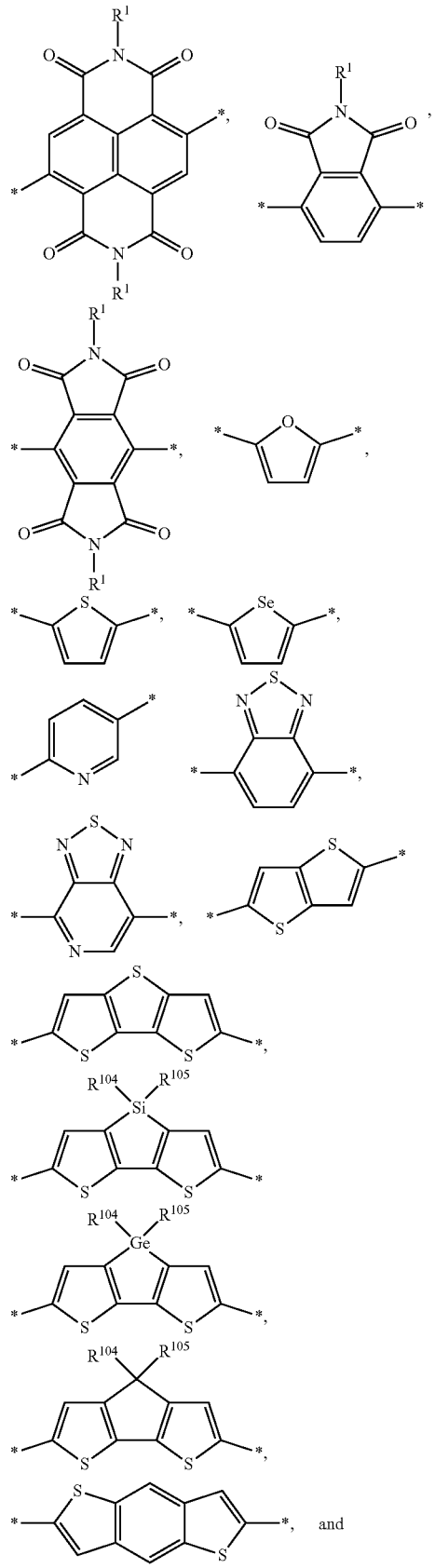

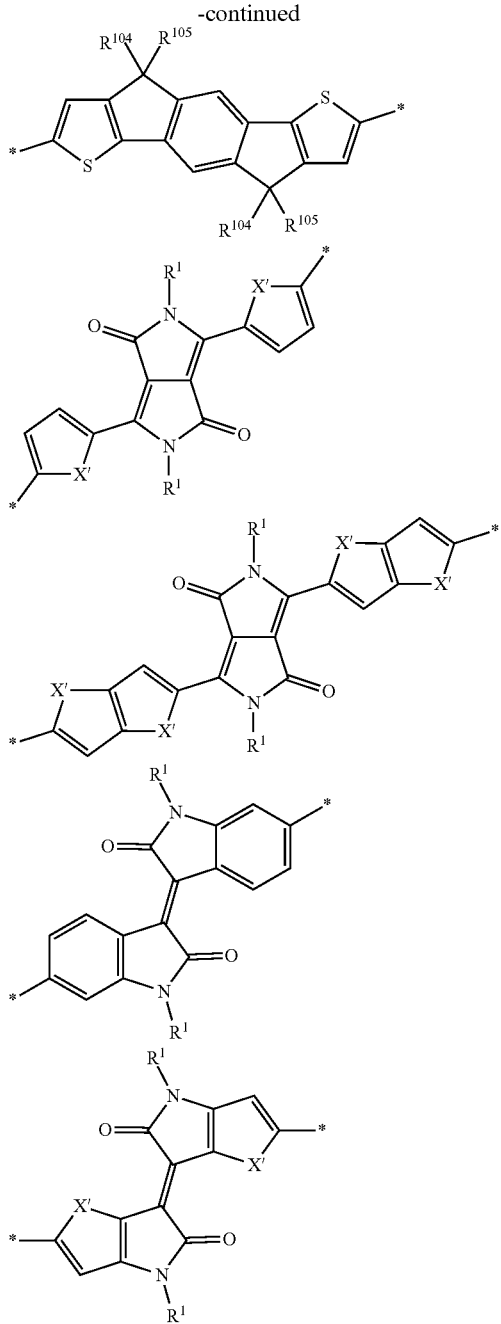

wherein

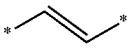 [SMILES: */C=C/*]

is unsubstituted.

In particular, $L^1$ and $L^2$ are independently from each other and at each occurrence $C_{6-30}$-arylene and 5 to 30 membered heteroarylene and

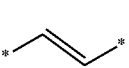

wherein $C_{6-30}$-arylene and 5 to 30 membered heteroarylene is selected from the group consisting of

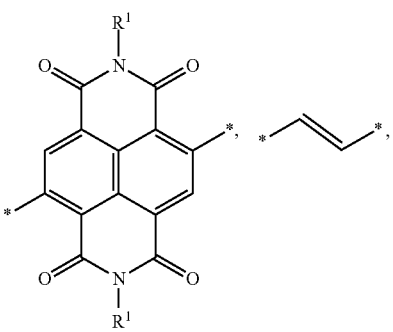

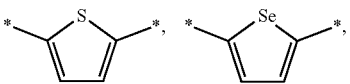

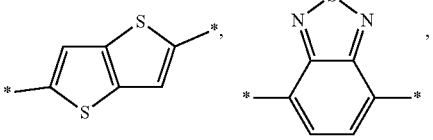

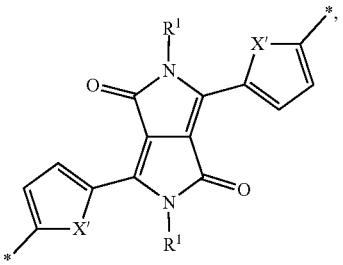

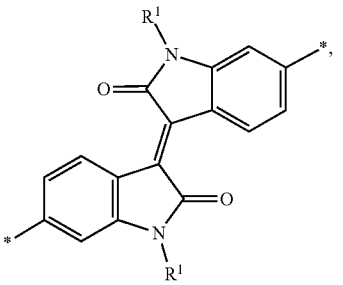

wherein
- $R^{104}$ and $R^{105}$ are independently and at each occurrence selected from the group consisting of H and $C_{1-20}$-alkyl,
- X' is O, S, or Se, preferably S or Se, particularly preferably S.
- $R^1$ are independently and at each occurrence a $C_{1-36}$-alkyl group, wherein
5 to 30 membered heteroarylene can be substituted with one to six substituents $R^3$ at each occurrence selected from the group consisting of $C_{1-30}$-alkyl, $C_{1-30}$-alkoxy, CN and halogen.

-continued

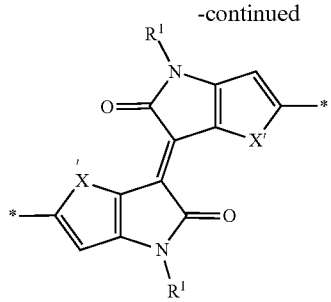

wherein
5 to 30 membered heteroarylene is unsubstituted,
X' is O, S, or Se, preferably S or Se, particularly preferably S.
$R^1$ are independently and at each occurrence a group $C_{1-36}$-alkyl.
In even more preferred polymers comprising at least one unit of formulae (1) or (1')
$R^1$ is at each occurrence selected from the group consisting of $C_{1-36}$-alkyl, $C_{2-36}$-alkenyl and $C_{2-36}$-alkynyl,
wherein
$C_{1-36}$-alkyl, $C_{2-36}$-alkenyl and $C_{2-36}$-alkynyl can be substituted with one to twenty substituents independently selected from the group consisting of $C_{5-6}$-cycloalkyl, $C_{6-10}$-aryl, 5 to 10 membered heteroaryl, $OR^a$, $SR^a$, $Si(R^{Sia})(R^{Sib})(R^{Sic})$, $-O-Si(R^{Sia})(R^{Sib})(R^{Sic})$, halogen, and CN; and at least two $CH_2$-groups, but not adjacent $CH_2$-groups, of $C_{1-36}$-alkyl, $C_{2-36}$-alkenyl and $C_{2-36}$-alkynyl can be replaced by O or S,
wherein
$R^a$ and $R^b$ are independently selected from the group consisting of H, $C_{1-20}$-alkyl, $C_{2-20}$-alkenyl, $C_{2-20}$-alkynyl, $C_{5-6}$-cycloalkyl and $C_{6-10}$-aryl
$R^{Sia}$, $R^{Sib}$ and $R^{Sic}$ are independently selected from the group consisting of H, $C_{1-20}$-alkyl, $C_{2-20}$-alkenyl, $C_{2-20}$-alkynyl, $C_{5-6}$-cycloalkyl, $C_{6-10}$-aryl, $-[O-SiR^{Sid}R^{Sie}]_o-R^{Sif}$
wherein
o is an integer from 1 to 50,
$R^{Sid}$, $R^{Sie}$, $R^{Sif}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, $-[O-SiR^{Sig}R^{Sih}]_p-R^{Sii}$,
wherein
p is an integer from 1 to 50,
$R^{Sig}R^{Sih}$, $R^{Sii}$ are independently selected from the group consisting of H, $C_{1-30}$-alkyl, $C_{2-20}$-alkenyl, $C_{2-20}$-alkynyl, $C_{5-6}$-cycloalkyl, $C_{6-10}$-aryl, $O-Si(CH_3)_3$,
$C_{1-20}$-alkyl, $C_{2-20}$-alkenyl and $C_{2-20}$-alkynyl can be substituted with one to ten substituents selected from the group consisting of halogen and CN,
$R^2$ is at each occurrence selected from the group consisting of unsubstituted hydrogen, $C_{1-30}$-alkyl and halogen,
n is 0 or 1,
m is 0, 1 or 2, and
$L^1$ and $L^2$ are independently from each other and at each occurrence selected from the group consisting of 5 to 30 membered heteroarylene,
and

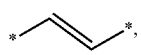

wherein 5 to 30 membered heteroarylene is selected from the group consisting of

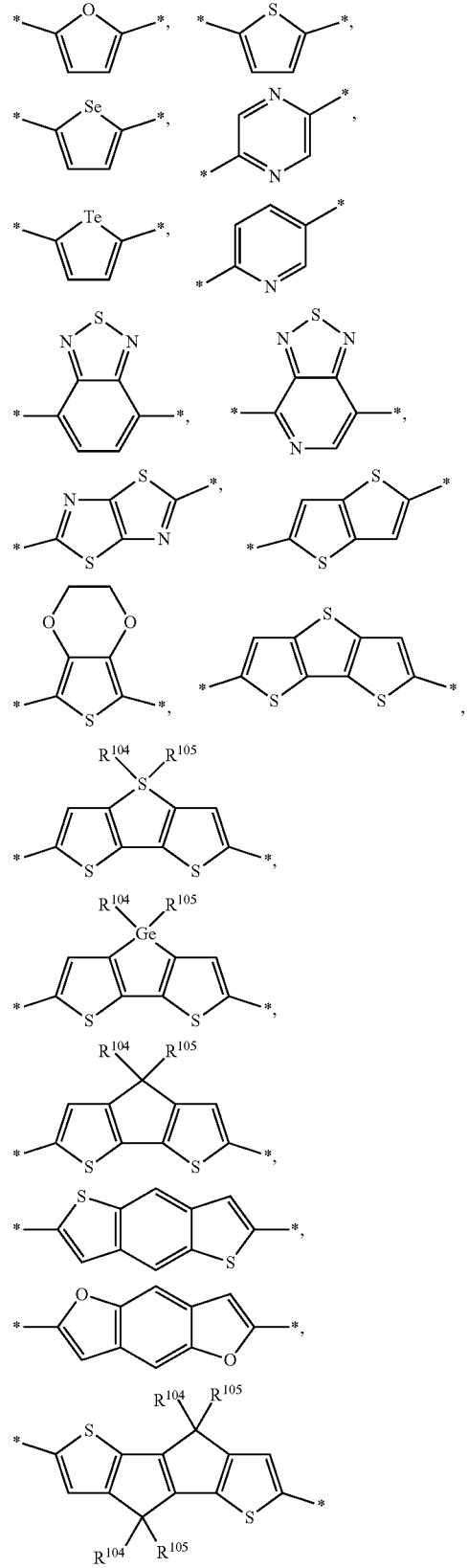

-continued

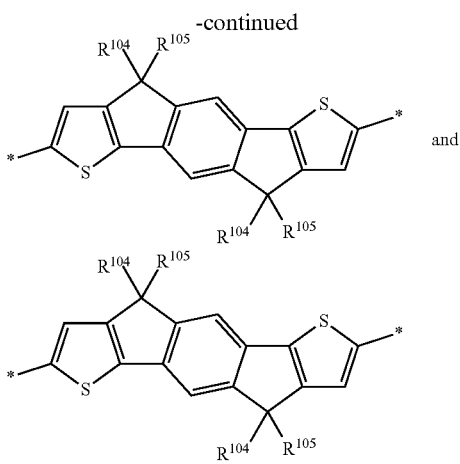

and 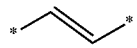

wherein
$R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system,
wherein
$C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
$C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
$C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$;
wherein
$R^s$ and $R^t$ are independently selected from the group consisting of H, $C_{1-10}$-alkyl, $C_{2-10}$-alkenyl and $C_{2-10}$-alkynyl,
wherein
$C_{1-10}$-alkyl, $C_{2-10}$-alkenyl and $C_{2-10}$-alkynyl can be substituted with one to five substituents selected from the group consisting of halogen, CN and $NO_2$, wherein
5 to 30 membered heteroarylene can be substituted with one to six substituents $R^3$ at each occurrence selected from the group consisting of $C_{1-30}$-alkyl and halogen, and
wherein

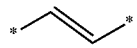 [SMILES: */C=C/*]

can be substituted with one or two substituents $R^4$ at each occurrence selected from the group consisting of $C_{1-30}$-alkyl, $C(O)$—$R^{41}$, $C(O)$—$OR^{41}$ and CN,
wherein
$R^{41}$ is at each occurrence $C_{1-30}$-alkyl.

In most preferred polymers comprising at least one unit of formulae (1) or (1')
$R^1$ is at each occurrence unsubstituted $C_{1-36}$-alkyl,
$R^2$ is hydrogen,
n is 0,
m is 0, 1 or 2, and
$L^1$ and $L^2$ are independently from each other and at each occurrence 5 to 30 membered heteroarylene,
wherein 5 to 30 membered heteroarylene is selected from the group consisting of

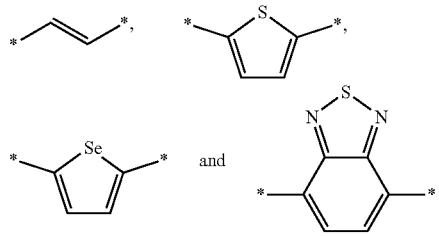

wherein
5 to 30 membered heteroarylene can be substituted with $R^3$, in particular with fluorine.

In other preferred embodiments, $L_1$ and $L_2$ are selected from

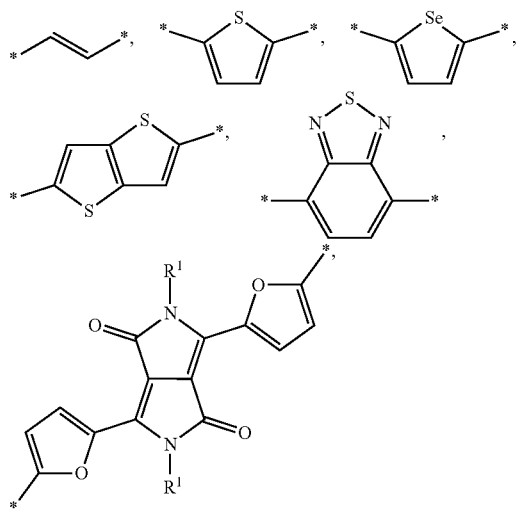

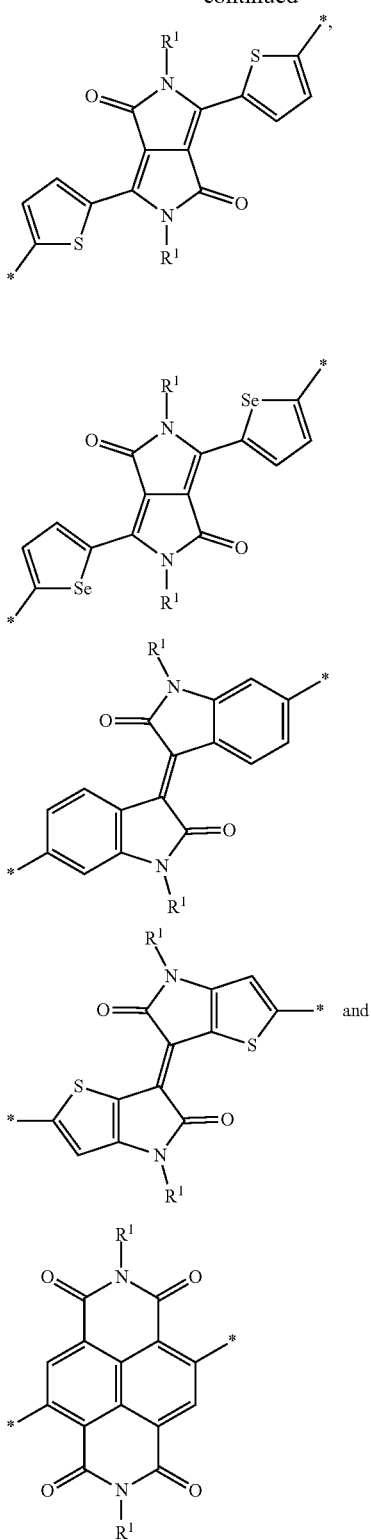
wherein
R¹ is at each occurrence unsubstituted $C_{1-36}$-alkyl,
R³ and R⁴ is hydrogen,
n is 0, 1 or 2
m is 0, 1 or 2
Particular preferred polymers of the present invention comprise at least one unit of formula
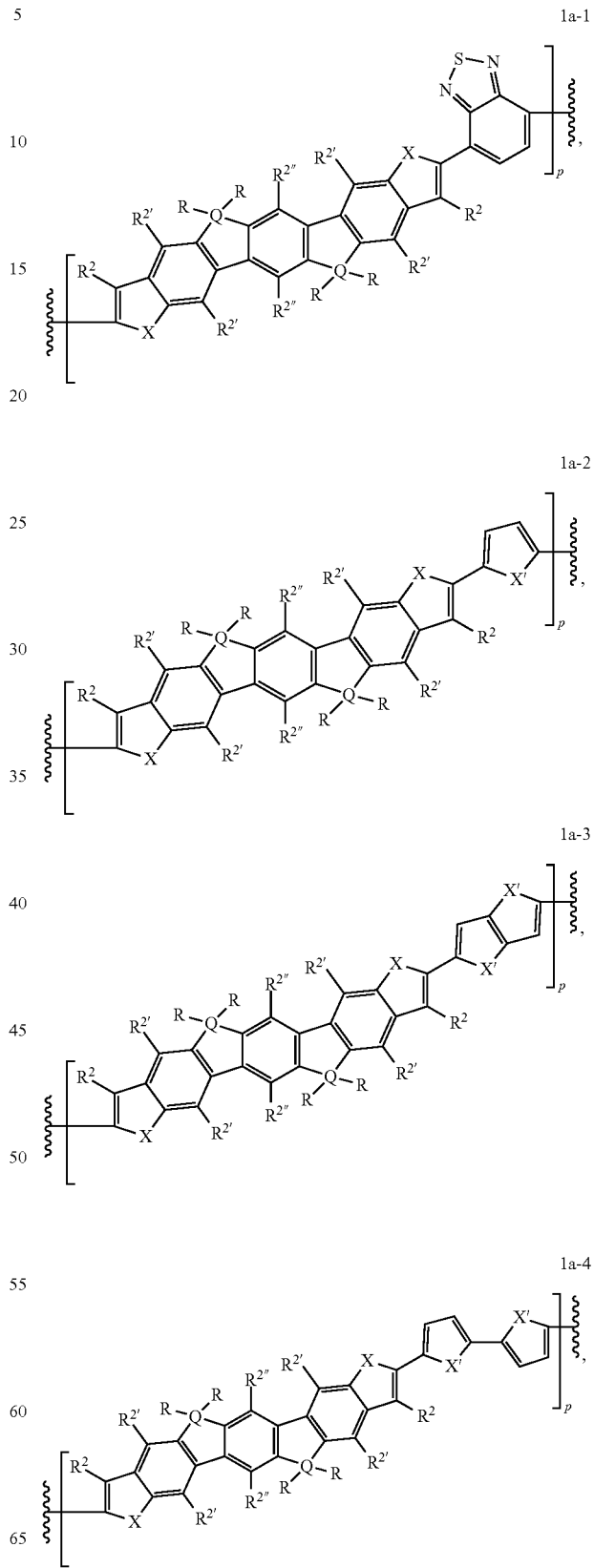

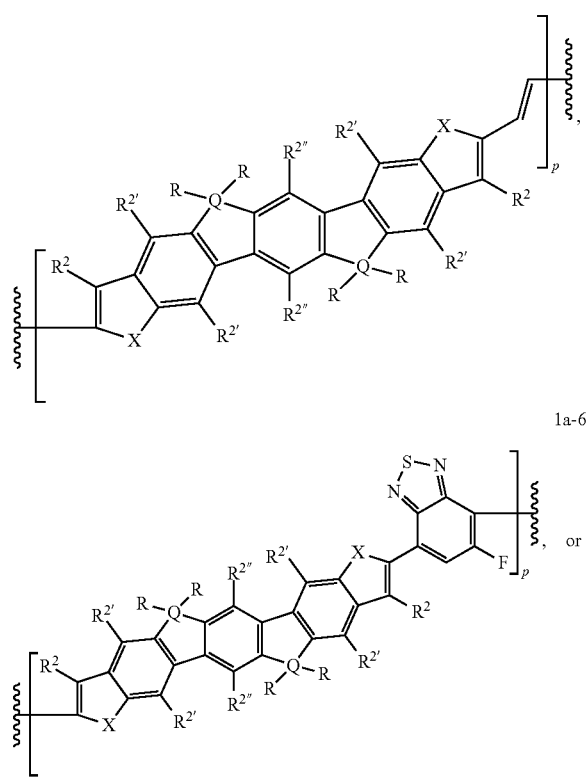

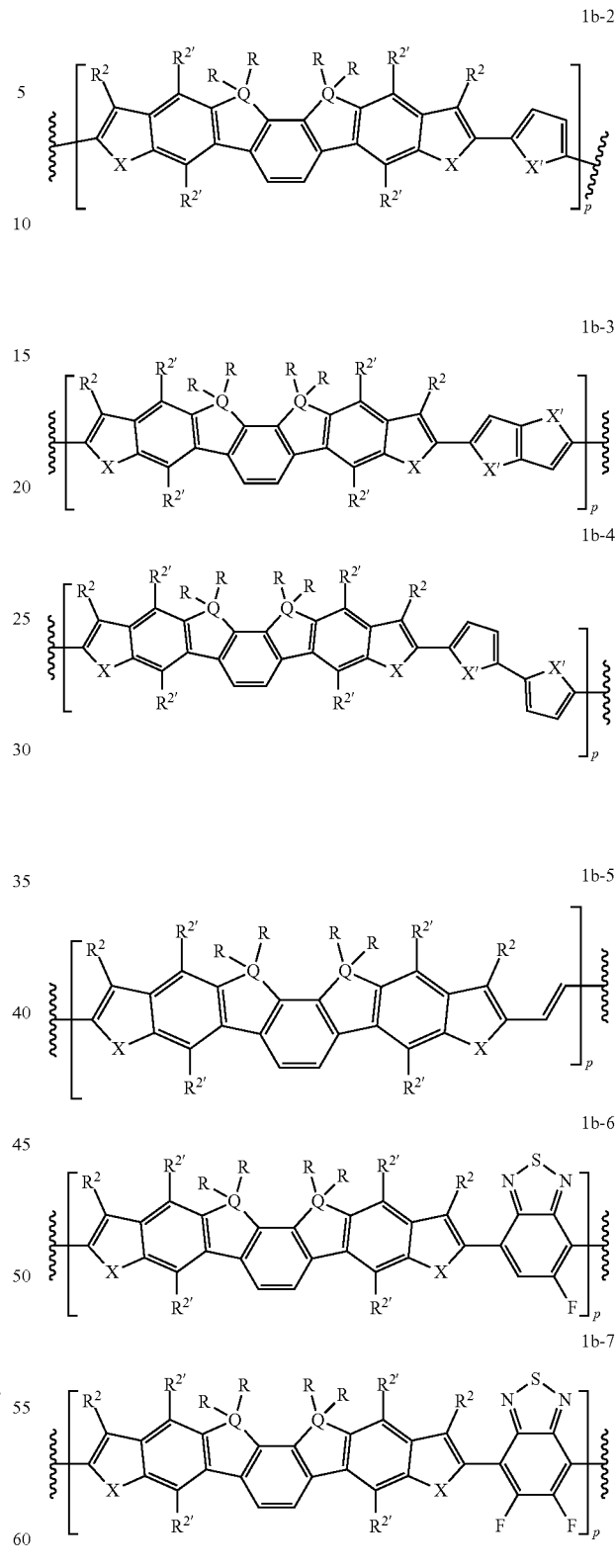

where polymers comprising at least a group of formula 1a-1 are especially preferred, and wherein p is an integer from 2 to 1000

X, X' Q, R, $R^2$, $R^{2'}$, $R^{2''}$ are defined as above;

In another embodiment of the present invention particularly preferred polymers comprise at least one unit of formula

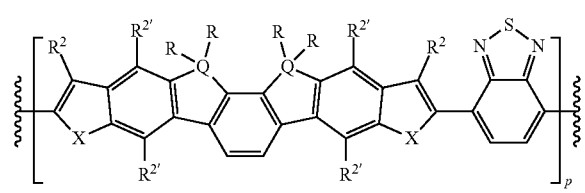

where polymers comprising at least a group of formula 1b-1 are especially preferred, and in still another embodiment of the present invention particularly preferred polymers comprise at least one unit of formula

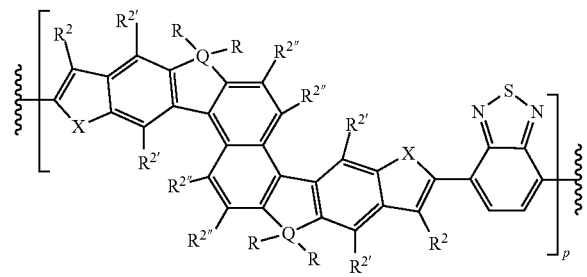

1f-1

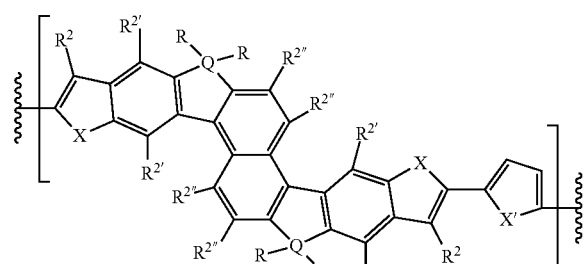

1f-2

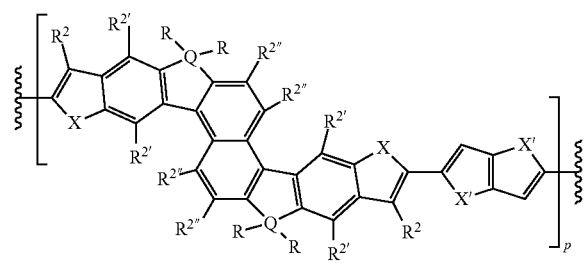

1f-3

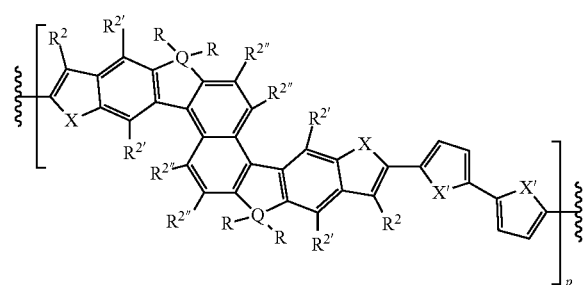

1f-4

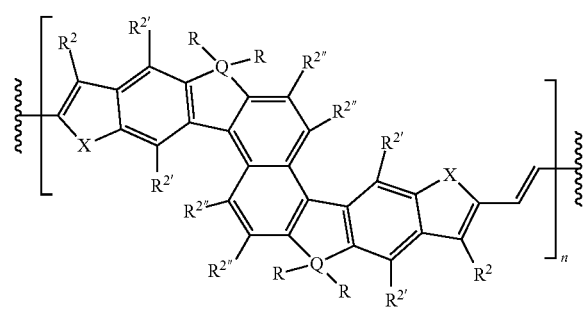

1f-5

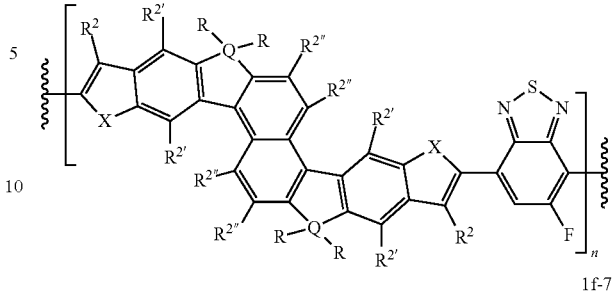

1f-6

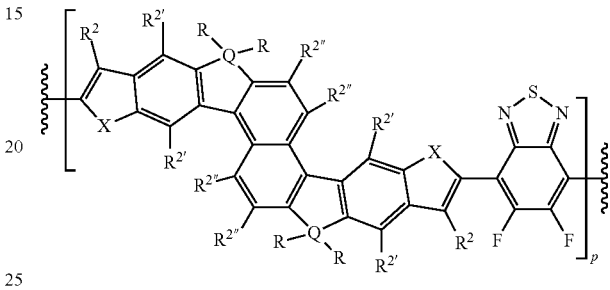

1f-7 where polymers comprising at least a group of formula 1f-1 are especially preferred, and
wherein p is an integer from 2 to 1000
X, X' Q, R, $R^2$, $R^{2'}$, $R^{2''}$ are defined as above;
p is preferably 3 to 200, more preferably 4 to 100 and most preferably 5 to 50,
R is preferably at each occurrence $C_{1-36}$-alkyl,
$R^2$, $R^{2'}$ and $R^{2''}$ are at each occurrence preferably hydrogen,
Q is preferably at each occurrence carbon,
X is preferably at each occurrence S, or Se, especially S,
X' is preferably at each occurrence S or Se, especially S,
The polymers of the present invention have preferably a weight average molecular weight ($M_w$) of 1 to 10000 kDa and a number average molecular weight ($M_n$) of 1 to 10000 kDa. The polymers of the present invention have more preferably a weight average molecular weight ($M_w$) of 1 to 1000 kDa and a number average molecular weight ($M_n$) of 1 to 100 kDa. The polymers of the present invention have even more preferably a weight average molecular weight ($M_w$) of 5 to 1000 kDa and a number average molecular weight ($M_n$) of 5 to 100 kDa. The polymers of the present invention have still more preferably a weight average molecular weight ($M_w$) of 10 to 1000 kDa and a number average molecular weight ($M_n$) of 10 to 100 kDa. The polymers of the present invention have most preferably a weight average molecular weight ($M_w$) of 10 to 100 kDa and a number average molecular weight ($M_n$) of 5 to 60 kDa. The weight average molecular weight ($M_w$) and the number average molecular weight ($M_n$) can be determined by gel permeation chromatography (GPC) e.g. at 80° C. using chlorobenzene or preferably at 150° C. using trichlorobenzene as eluent and a polystyrene as standard.

The polymers of the present invention can be prepared by methods known in the art, e.g. by Suzuki-, Stille, Yamamoto- or direct heteroaryl-polymerization.

The polymers of the present invention are preferably fully conjugated along the whole polymer backbone.

For examples, polymers of the present invention comprising at least one unit of formulae (1) or (1'), wherein n is 0 and which are of formulae (1-I) or (1-I')

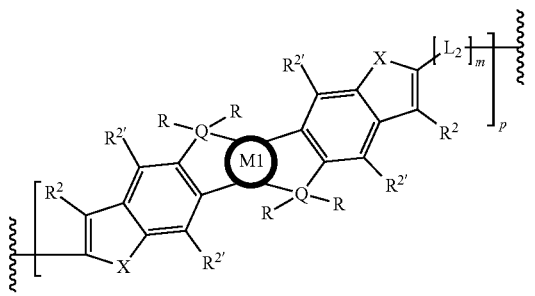
(1-I)

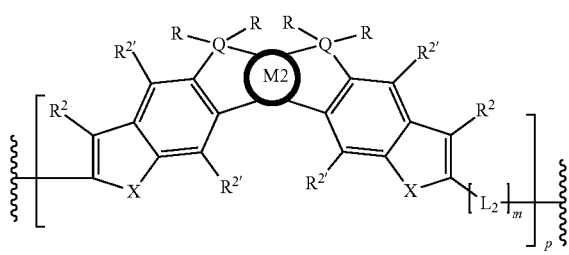
(1-I')

wherein
p, M1, M2, Q, X, R, $R^2$, $R^{2'}$, and $L^2$ are as defined above,
m is 0, 1, 2, 3 or 4,
can be prepared by reacting a compound of formulae (3) or (3')

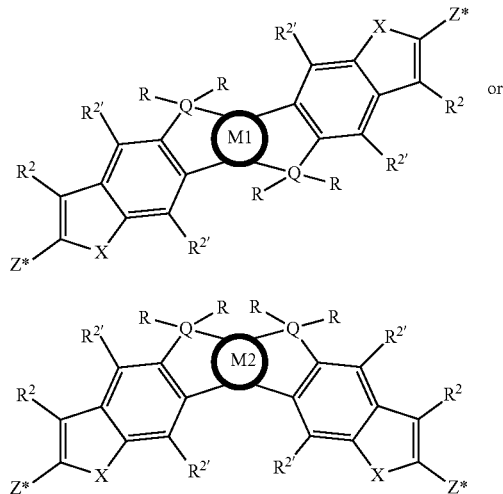
(3)
(3')

wherein Z* is at each occurrence I, Br, Cl or O—S(O)$_2$CF$_3$, and p, M1, M2, Q, X, R, $R^2$ and $R^{2'}$ are as defined above, with one mol equivalents of a compound of formula (10)

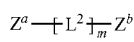
(10)

wherein
$L^2$ is as defined for the compound of formula (1-I), and $Z^a$ and $Z^b$ are independently selected from the group consisting of B(OZ$^1$)(OZ$^2$), SnZ$^1$Z$^2$Z$^3$,

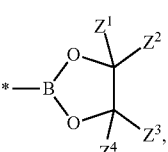
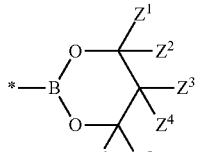 and

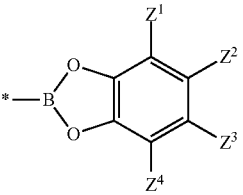

wherein $Z^1$, $Z^2$, $Z^3$, $Z^4$, $Z^5$ and $Z^6$ are independently from each other and at each occurrence H or $C_{1-4}$-alkyl.

Z* is preferably at each occurrence I or Br, especially Br.
$Z^a$ and $Z^b$ are preferably independently selected from the group SnZ$^1$Z$^2$Z$^3$ or

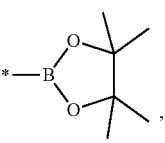, especially SnZ$^1$Z$^2$Z$^3$.

The polymer comprising a compound of formulae (1-I) or (1-I') can also be obtained in analogy from compounds (4) or (4') and (11), where the meaning of R, $R^2$, $R^{2'}$, Q, X, $L^2$, Z*, $Z^a$ and $Z^b$ is defined above:

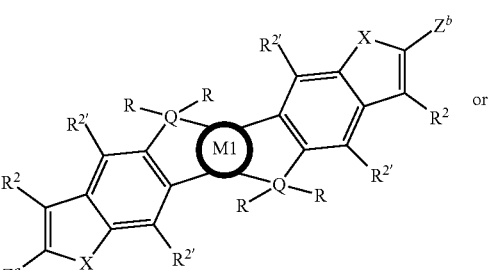
(4)
or (4')

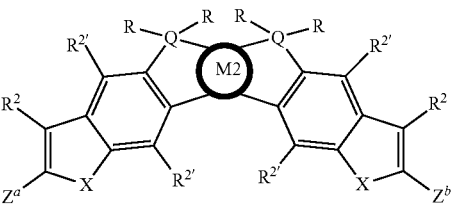
(11)

For example, polymers of the present invention comprising at least one unit of formulae (1) or (1'), wherein n and m are 0 and which are of formulae (1-II) or (1-II')

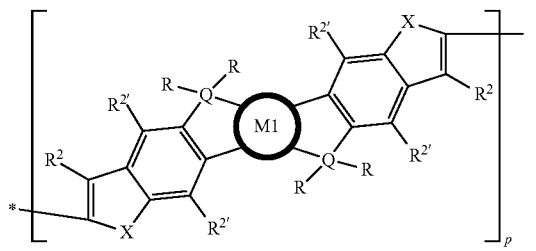

1-II

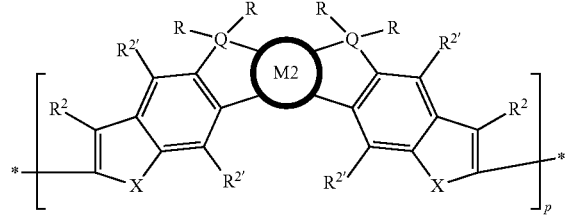

1-II' wherein
p, M1, M2, Q, X, R, $R^2$, $R^{2'}$ are as defined above,
can e.g. be prepared by reacting a compound of formulae (3) or (3')

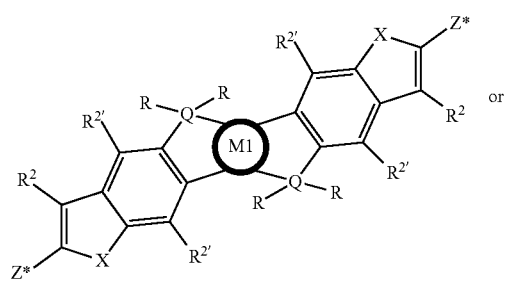

(3)

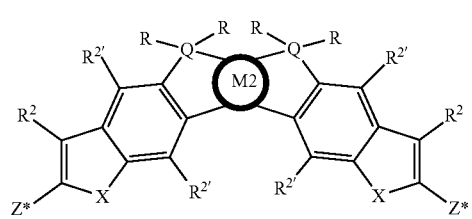

(3')

wherein Z* is at each occurrence I, Br, Cl or O—S(O)$_2$CF$_3$, and R, $R^2$ and $R^{2'}$ are as defined above,
with a compound of formulae (4) or (4')

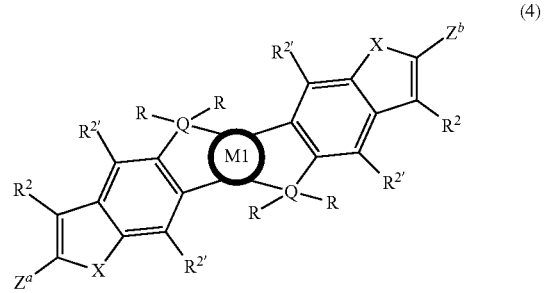

(4)

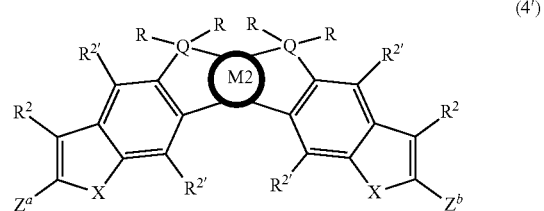

(4')

wherein
R, $R^2$ and $R^{2'}$ are as defined for the compound of formula (1-II), and
$Z^a$ and $Z^b$ are independently selected from the group consisting of $B(OZ^1)(OZ^2)$, $SnZ^1Z^2Z^3$,

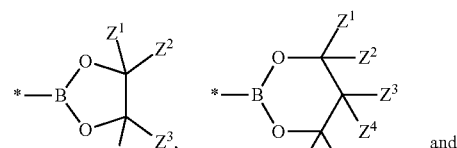

and

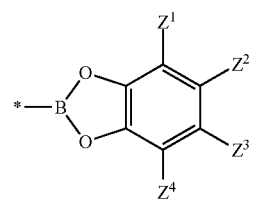

wherein $Z^1$, $Z^2$, $Z^3$, $Z^4$, $Z^5$ and $Z^6$ are independently from each other and at each occurrence H or $C_{1-4}$-alkyl.

Z* is preferably at each occurrence I or Br, especially Br.

$Z^a$ and $Z^b$ are preferably independently selected from the group $SnZ^1Z^2Z^3$ or

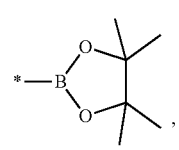

especially $SnZ^1Z^2Z^3$.

When $Z^a$ and $Z^b$ are independently selected from the group consisting of $B(OZ^1)(OZ^2)$,

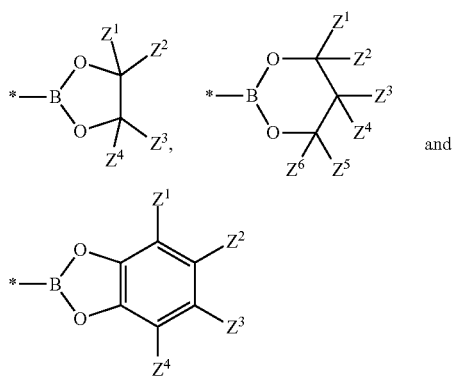

wherein $Z^1$, $Z^2$, $Z^3$, $Z^4$, $Z^5$ and $Z^6$ are independently from each other and at each occurrence H or $C_{1-4}$-alkyl, the reaction is usually performed in the presence of a catalyst, preferably a Pd catalyst such as $Pd(P(Ph)_3)_4$, $Pd(OAc)_2$ and $Pd_2(dba)_3$, and a base such as $K_3PO_4$, $Na_2CO_3$, $K_2CO_3$, LiOH and NaOMe. Depending on the Pd catalyst, the reaction may also require the presence of a phosphine ligand such as $P(Ph)_3$, $P(o\text{-tolyl})_3$ and $P(tert\text{-Bu})_3$. The reaction is also usually performed at elevated temperatures, such as at temperatures in the range of 40 to 250° C., preferably 60 to 200° C. The reaction can be performed in the presence of a suitable solvent such as tetrahydrofuran, toluene or chlorobenzene. The reaction is usually performed under inert gas.

When $Z^a$ and $Z^b$ are independently $SnZ^1Z^2Z^3$, wherein $Z^1$, $Z^2$ and $Z^3$ are independently from each other $C_{1-4}$-alkyl, the reaction is usually performed in the presence of a catalyst, preferably a Pd catalyst such as $Pd(P(Ph)_3)_4$ and $Pd_2(dba)_3$. Depending on the Pd catalyst, the reaction may also require the presence of a phosphine ligand such as $P(Ph)_3$, $P(o\text{-tolyl})_3$ and $P(tert\text{-Bu})_3$. The reaction is also usually performed at elevated temperatures, such as at temperatures in the range of 40 to 250° C., preferably 60 to 200° C. The reaction can be performed in the presence of a suitable solvent such as toluene or chlorobenzene. The reaction is usually performed under inert gas.

The compound of formulae (3) or (3') can be prepared by methods known in the art from a compound of formulae (5) or (5').

For examples, compounds of formulae (3) or (3'), wherein

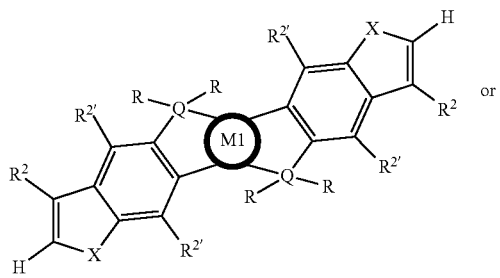
(3)

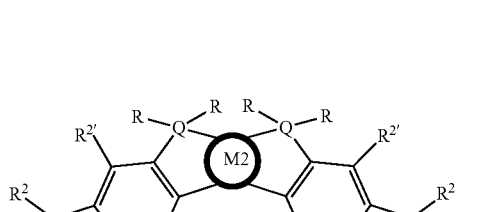
(3')

wherein $Z^*$ is I, Br, Cl or O-triflate, and R is at each occurrence $C_{1-30}$-alkyl, $R^2$ and $R^{2'}$ are hydrogen can be prepared by treating a compound of formulae (5) or (5')

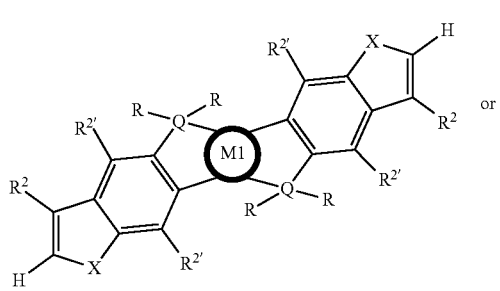
(5)

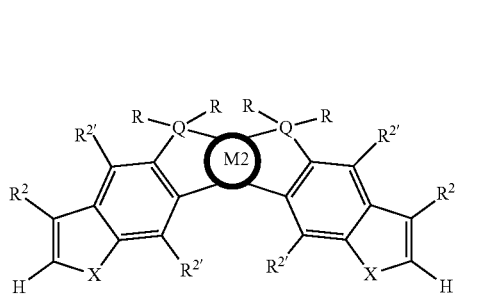
(5')

wherein R is at each occurrence $C_{1-3}$-alkyl. $R^2$ and $R^{2'}$ are hydrogen with a $Z^*$-donor.

$Z^*$ is preferably I or Br, especially Br.

For example, when $Z^*$ is Br, the $Z^*$-donor can be N-bromosuccinimide. When using N-bromosuccinimide as $Z^*$-donor, the reaction can be performed at 0° C. in the presence of $CHCl_3$/acetic acid as solvent.

A compound of formula (5) where Q is a carbon atom and M1 is a phenyl ring, can e.g. be prepared by the synthetic pathway, depicted in Scheme 1. $R^2$, $R^{2'}$, X and R have the meaning defined above Scheme 1

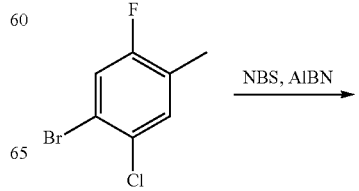

-continued
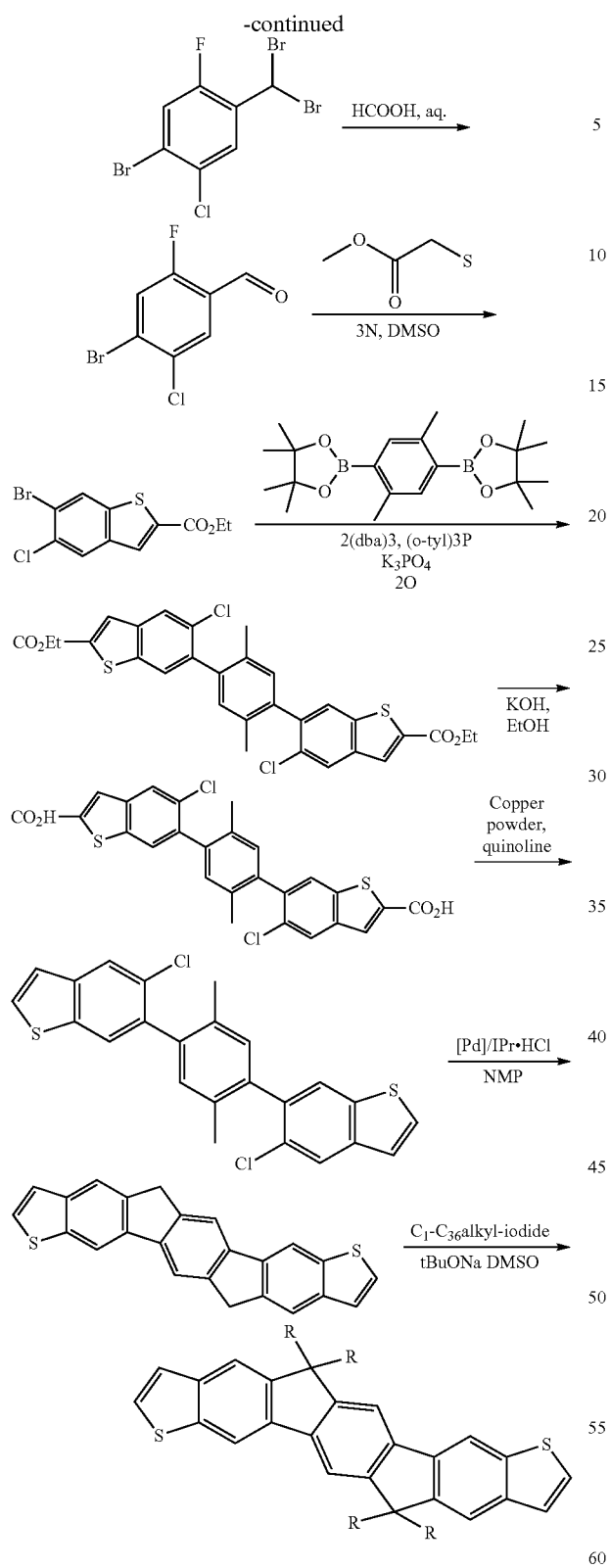
R² is preferably hydrogen,
R²' is preferably hydrogen,
X is preferably O, S or Se, more preferably S or Se, especially S,
R is preferably $C_{1-36}$-alkyl.
Also part of the invention are intermediates of formulae (3), (3'), (4), (4'), (5) and (5'):
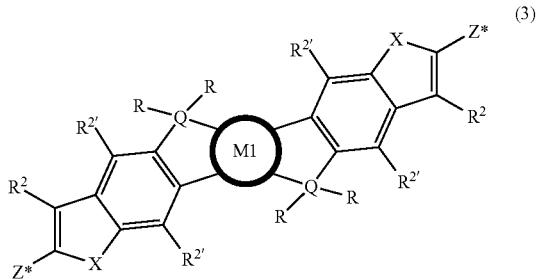
(3)
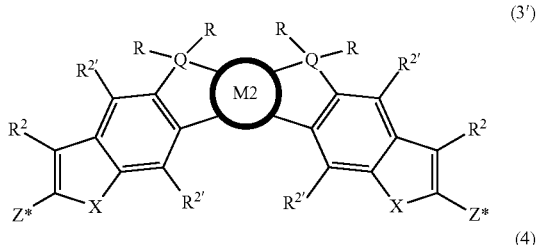
(3')
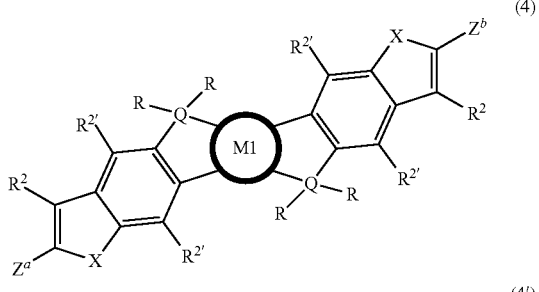
(4)
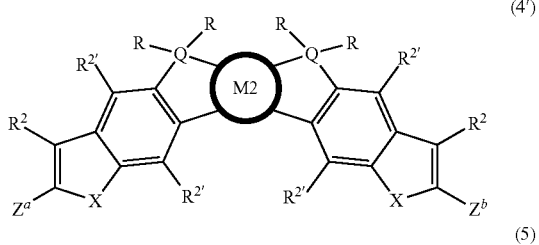
(4')
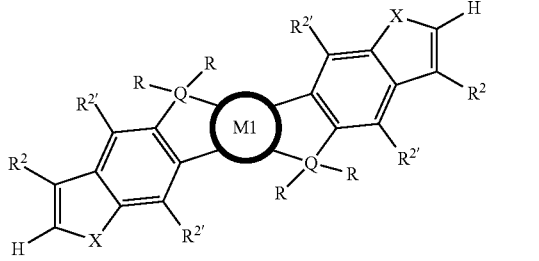
(5)
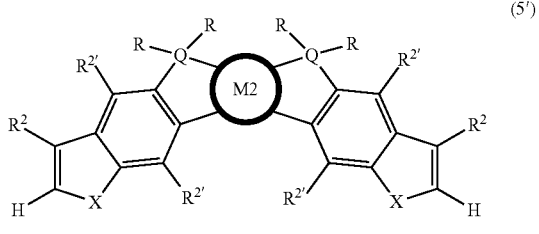
(5')
wherein
R², R²', R²'', X, Q, M1, M2, $Z^a$, $Z^b$ and R have the meaning defined above.
Z* is at each occurrence I, Br, Cl or O—S(O)₂CF₃.

In preferred intermediates of formulae (3), (3'), (4), (4'), (5), (5') at each occurrence $R^2$ and $R^{2'}$ are hydrogen, unsubstituted $C_{1-30}$-alkyl or halogen;

X is O, S or Se;

Q is a carbon atom;

R is hydrogen, $C_{1-36}$-alkyl, $C_{2-36}$-alkenyl, $C_{2-36}$-alkynyl, $C_{5-12}$-cycloalkyl, or phenyl, preferably $C_{1-36}$-alkyl;

Z* is at each occurrence I or Br;

$Z^a$, $Z^b$ are

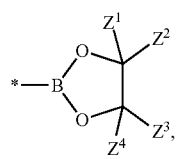

where $Z^1$-$Z^4$ are methyl.

In more preferred intermediates of formulae (3), (3'), (4), (4'), (5), (5') at each occurrence $R^2$ and $R^{2'}$ are hydrogen or halogen;

X is S or Se;

Q is a carbon atom;

R is $C_{1-36}$-alkyl,

Z* is I or Br;

In most preferred intermediates of formulae (3), (3'), (4), (4'), (5), (5') at each occurrence $R^2$ and $R^{2'}$ are hydrogen, X is S, Q is a carbon atom;

R is $C_{1-36}$-alkyl,

Z* is I or Br;

Preferred intermediates of formula (3) are

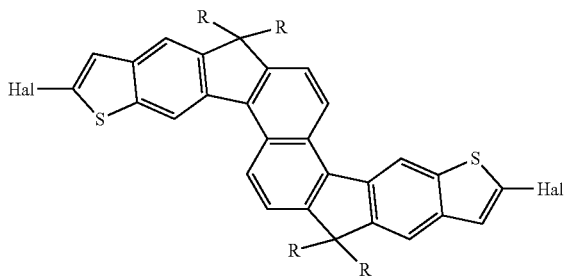

(3-I)

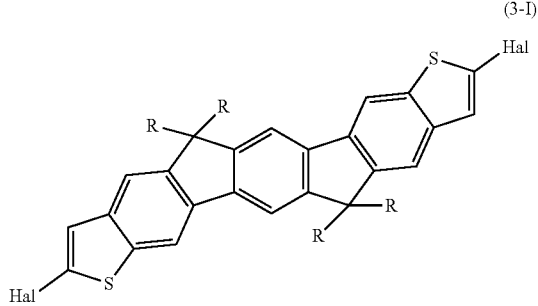

(3-II)

-continued (3-III)

wherein

R is at each occurrence $C_{1-36}$-alkyl,

Hal is independently at each occurrence Br or I.

Particular preferred intermediates of formula (3) are

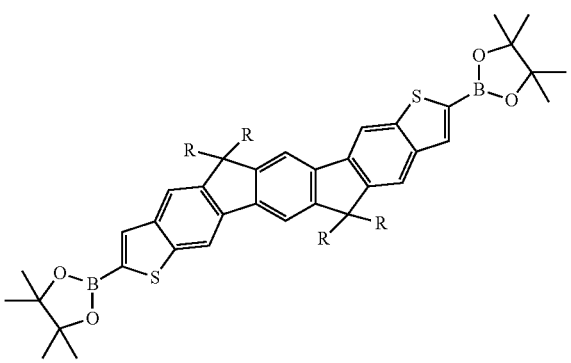

(3-I)

wherein, R is at each occurrence $C_{1-36}$-alkyl and $R^2$ is hydrogen.

Preferred intermediates of formula (4) are

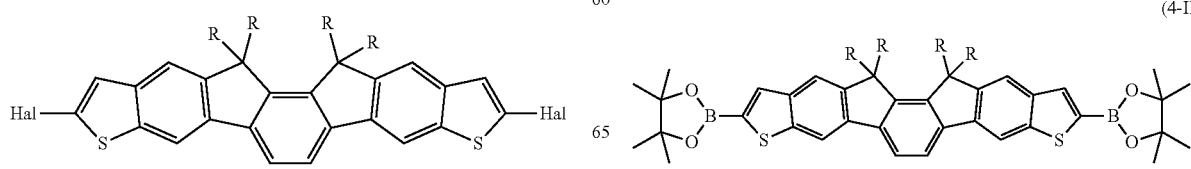

(4-I)

(4-II)

(4-III)

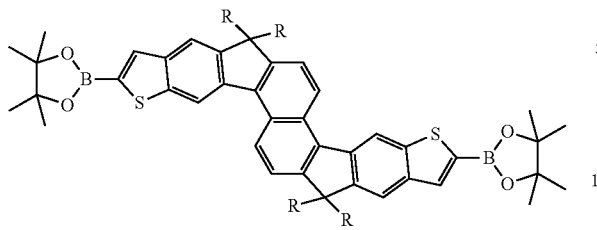

wherein

R is at each occurrence $C_{1-36}$-alkyl.

Particular preferred intermediates of formula (4) are (4-I)

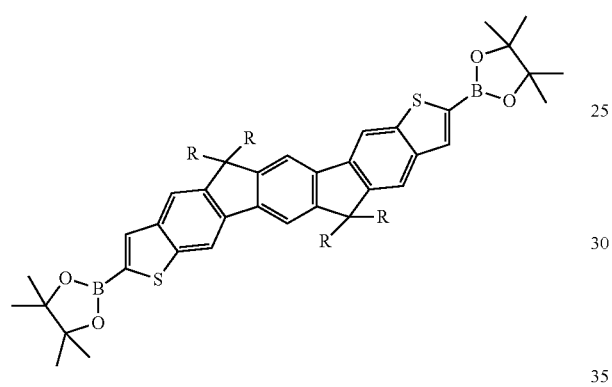

wherein, R is at each occurrence $C_{1-36}$-alkyl and $R^2$ is hydrogen.

Preferred intermediates of formula (5) are (5-I)

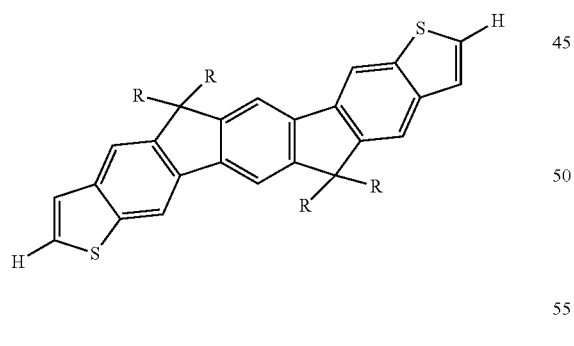

(5-II)

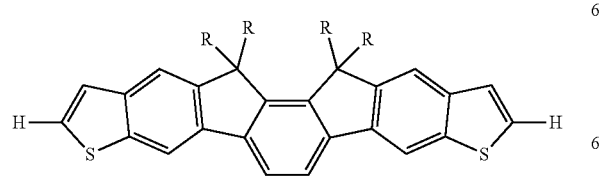

(5-III)

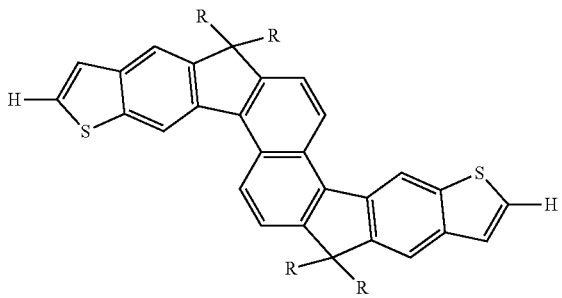

wherein

R is at each occurrence $C_{1-36}$-alkyl.

Particular preferred intermediates of formula (5) are (5-I)

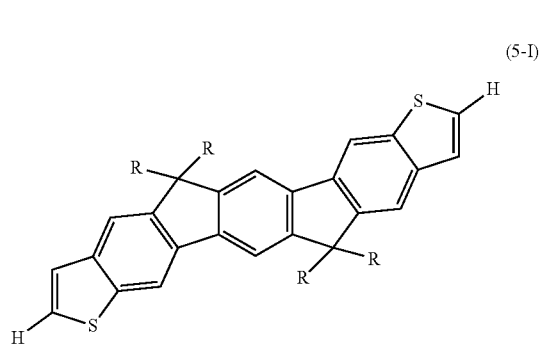

wherein, R is at each occurrence $C_{1-36}$-alkyl and $R^2$ is hydrogen.

In another embodiment of the present invention intermediates of formula (6) are preferred (6-I)

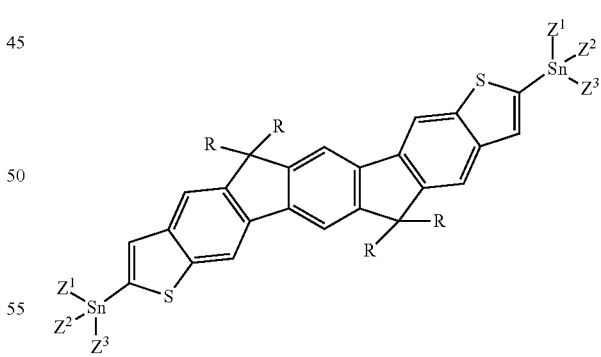

(6-II)

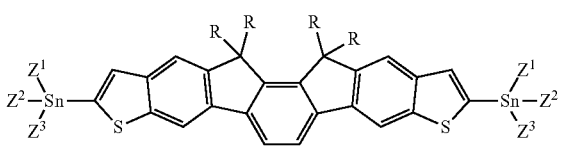

-continued (6-III)

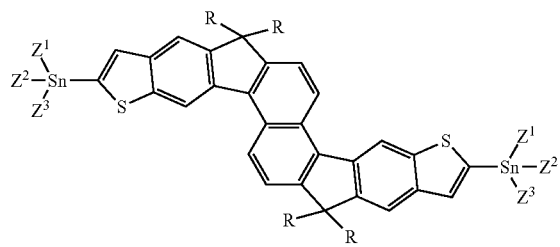

wherein
R is at each occurrence $C_{1-36}$-alkyl
$Z^1$, $Z^2$ and $Z^3$ are independently from each other $C_{1-4}$-alkyl.
Particular preferred intermediates of formula (6) are (6-I)

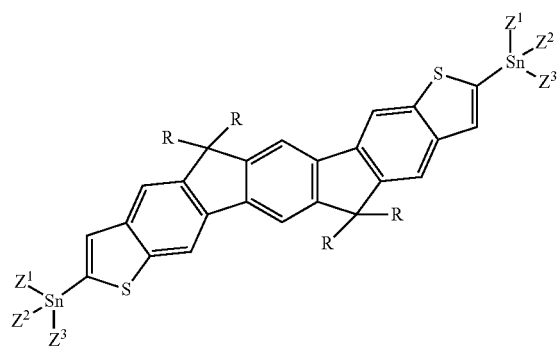

Also part of the invention is an electronic device comprising the polymer of the present invention.

The electronic device can be an organic photovoltaic device (OPVs), an organic field-effect transistor (OFETs), an organic light emitting diode (OLEDs) or an organic photodiode (OPDs).

Preferably, the electronic device is an organic photovoltaic device (OPVs), an organic field-effect transistor (OFETs) or an organic photodiode (OPDs).

More preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the polymer of the present invention.

The semiconducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled monolayer of organic silane derivates or organic phosphoric acid derivatives. An example of an organic silane derivative is octyltrichlorosilane. An examples of an organic phosphoric acid derivative is octyldecylphosphoric acid. The self-assembled monolayer comprised in the dielectric layer is usually in contact with the semiconducting layer.

The source/drain electrodes can be made from any suitable organic or inorganic source/drain material. Examples of inorganic source/drain materials are gold (Au), silver (Ag) or copper (Cu), as well as alloys comprising at least one of these metals. The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide or gold (Au), or alloys comprising at least one of these metals. The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a bottom-gate top-contact organic field effect transistor can be prepared as follows: The dielectric material, for example $Al_2O_3$ or silicon dioxide, can be applied as a layer on a gate electrode such as highly doped silicon wafer, which also functions as substrate, by a suitable deposition method such as atom layer deposition or thermal evaporation. A self-assembled monolayer of an organic phosphoric acid derivative or an organic silane derivative can be applied to the layer of the dielectric material. For example, the organic phosphoric acid derivative or the organic silane derivative can be applied from solution using solution-deposition techniques. The semiconducting layer can be formed by either solution deposition or thermal evaporation in vacuo of the polymer of the present invention on the self-assembled monolayer of the organic phosphoric acid derivative or the organic silane derivative. Source/drain electrodes can be formed by deposition of a suitable source/drain material, for example tantalum (Ta) and/or gold (Au), on the semiconducting layer through a shadow masks. The channel width (W) is typically 10 to 1000 μm and the channel length (L) is typically 5 to 500 μm.

For example, a top-gate bottom-contact organic field effect transistor can be prepared as follows: Sorce/drain electrodes can be formed by evaporating a suitable source/drain material, for example gold (Au), on photo-lithographically defined electrodes on a suitable substrate, for example a glass substrate. The semiconducting layer can be formed by depositing a solution of the polymers of the present invention, for example by spin-coating, on the source/drain electrodes, followed by annealing the layer at elevated temperatures such as at a temperature in the range of 80 to 360° C. After quenching the semiconducting layer, a dielectric layer can be formed by applying, for example, by spin-coating, a solution of a suitable dielectric material such as poly(methylmethacryate), on the semiconducting layer. The gate electrode of a suitable gate material, for example gold (Au), can be evaporated through a shadow mask on the dielectric layer.

Also part of the invention is the use of the polymer of the present invention as semiconducting material.

The polymers of the present invention show high charge carrier mobilities. In addition, the polymers of the present invention show a high stability, in particular a high thermal stability. Furthermore the polymers of the present invention are compatible with liquid processing techniques.

Also part of the invention is the use of the polymer of the present invention as luminescent material.

Also part of the invention is the use of the compound of the present invention as luminescent material.

EXAMPLES

General Experimental Details for Synthetic Part

Methods and materials: All reagents from commercial sources were used without further purification. Solvents were dried and purified using standard techniques. Most of the compounds were characterized by NMR, usually at room temperature. High-resolution mass spectrometry (HRMS) data was recorded using a Thermo Scientific-LTQ Velos Orbitrap MS in positive atmospheric pressure photoionization (+APPI) mode. UV-Vis spectra were recorded in a Varian Cary 100 spectrophotometer. Thermogravimetric analysis (TGA) was performed under $N_2$ using Bruker TGA-IR TG209F1 with a ramp of 10° C./min. Differential Scanning Calorimetry (DSC) was run on DSC-204F1-phoenix. Number average (Mn) and weight-average (Mw) molecular weight were determined by Agilent Technologies 1200 series GPC running in chlorobenzene at 80° C., using two PL mixed B columns in series and/or in trichlorobenzene at 150° C. and calibrated against narrow polydispersity polystyrene standards. Flash chromatography (FC) was performed on silica gel. Microwave experiments were performed in a Biotage initiator V 2.3.

Synthetic Details and Characterization

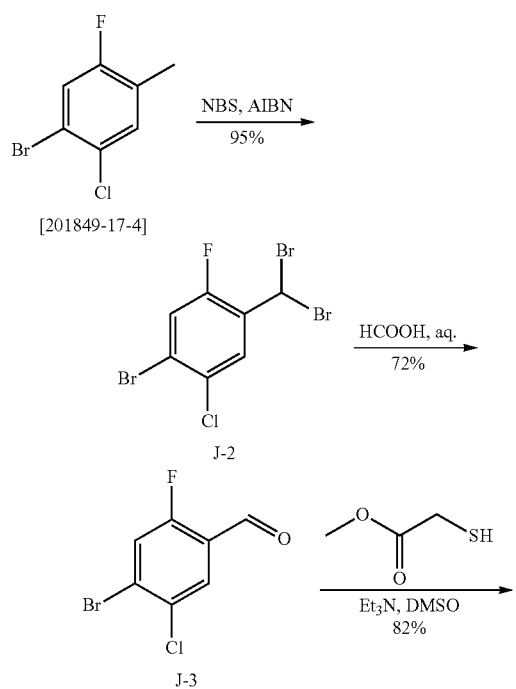

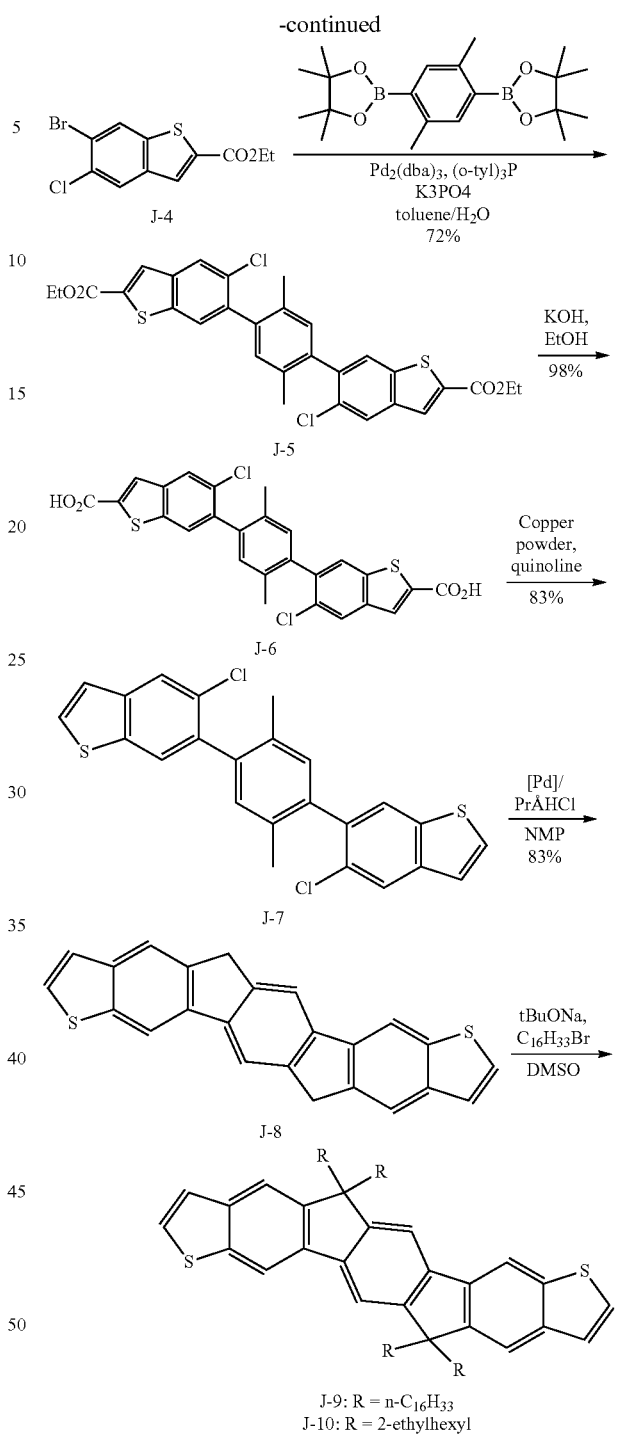

J-9: R = n-$C_{16}H_{33}$
J-10: R = 2-ethylhexyl

Example 1

Synthesis of 1-bromo-2-chloro-4-(dibromomethyl)-5-fluorobenzene (J-2)

1-bromo-2-chloro-5-fluoro-4-methylbenzene (20.0 g, 90 mmol), NBS (48.06 g, 270 mmol) and BPO (2.18 g, 9 mmol) dissolved in 1,2-dichloroethane (250 ml). Stirred at reflux until the starting material was consumed monitored by GC-MS and quenched with water and extracted with ethyl acetate. Organic phases collected and dried over magnesium sulfate, filtered and concentrated under vacuum. Purified via column chromatography on silica gel with 1:1 ethyl acetate:hexane
as eluent to afford a brown oil. Yield: 32.50 g (95%)
$^1$H NMR (700 MHz, CDCl$_3$) δ 7.91 (d, J=7.1 Hz, 1H), 7.36 (d, J=9.1 Hz, 1H), 6.80 (s, 1H).

Example 2

Synthesis of 4-bromo-5-chloro-2-fluorobenzaldehyde (J-3)

1-bromo-2-chloro-4-(dibromomethyl)-5-fluorobenzene (34.0 g, 89.2 mmol), dissolved in formic acid (500 ml) and stirred at reflux overnight. Allowed to cool to room temperature and poured into water. The resulting solid was collected, washed with water until the washings were no longer acidic and dried to afford a white solid. Yield: 15.32 g (72%)
$^1$H NMR (700 MHz, CDCl$_3$) δ 10.25 (s, 1H), 7.92 (d, J=6.5 Hz, 1H), 7.53 (d, J=9.2 Hz, 1H).

Example 3

Synthesis of Ethyl 6-bromo-5-chlorobenzo[b]thiophene-2-carboxylate (J-4)

4-bromo-5-chloro-2-fluorobenzaldehyde (22.40 g, 94.4 mmol) was dissolved in DMSO (200 ml). Triethylamine (39.5 ml, 283.2 mmol) and ethyl thioglycolate (12.4 ml, 113.2 mmol) were added and the mixture stirred at 80° C. The reaction was quenched with water when the starting material was totally disappeared monitored by GC-MS and extracted with ethyl acetate. The organic phases were collected, dried over magnesium sulfate, filtered and concentrated under vacuum. The product was purified by column chromatography on silica gel with 5:1 hexane:dichloromethane as eluent. Resulting in a yellowish solid. Yield: 24.74 g (82%)
$^1$H NMR (400 MHz, CDCl$_3$) δ 8.14 (s, 1H), 7.96 (s, 1H), 7.94 (s, 1H), 4.43 (q, 2H), 1.44 (t, 3H).

Example 4

Synthesis of Diethyl 6,6'-(2,5-dimethyl-1,4-phenylene)bis(5-chlorobenzo[b]thiophene-2-carboxylate) (J-5)

Ethyl 6-bromo-5-chlorobenzo[b]thiophene-2-carboxylate (2 g, 6.29 mmol), 2,2'-(2,5-dimethyl-1,4-phenylene)bis(4,4,5,5-tetramethyl-1,3,2-dioxaborolane) (0.90 g, 2.52 mmol) was dissolved in toluene/H$_2$O (15 mL/3 mL) in a 50 mL flask and digassed with argon, then Pd$_2$(dba)$_3$ (0.09 g, 0.25 mmol), (o-tol)$_3$P (0.09 g, 0.76 mmol), K$_3$PO$_4$ (8.01 g, 37.74 mmol) and 2 drops of aliquat were added into the mixture and digassed with argon again. The mixture was subjected to reflux for 24 h. After cooling to room temperature, the reaction mixture was extracted with chloroform, and the organic phase was collected and then passed through a short silicon gel column quickly and then recrystalized from chloroform/methanol, resulting in a white solid. Yield: 1.06 g (72%)
$^1$H NMR (500 MHz, CDCl$_3$) δ 8.05 (s, 2H), 8.01 (d, J=1.9 Hz, 2H), 7.86 and 7.77 (2 s (rotamers), 2H), 7.12 (s, 2H), 4.45 (q, 4H), 2.15 (s, 6H), 1.45 (t, J=7.2 Hz, 6H).

Example 5

Synthesis of 6,6'-(2,5-dimethyl-1,4-phenylene)bis(5-chlorobenzo[b]thiophene-2-carboxylic acid) (3-6)

Diethyl 6,6'-(2,5-dimethyl-1,4-phenylene)bis(5-chlorobenzo[b]thiophene-2-carboxylate) (10 g, 17.14 mmol) was dissolved in hot ethanol (300 mL) and potassium hydroxide (9.62 g, 171.4 mmol) in water (80 mL) added. The suspension was heated at reflux overnight. After cooling slightly, 6 N HCl (60 mL) was added portionwise. The residual solid was filtered, washed with water and dried to give an off-white solid. Yield: 9.04 g (98%)
$^1$H NMR (700 MHz, DMSO) δ 13.68 (s, 2H), 8.25 (d, J=1.9 Hz, 2H), 8.13 (d, J=2.1 Hz, 2H), 8.11 and 8.07 (2 s (rotamers), 2H), 2.06 (s, 6H).

Example 6

Synthesis of 6,6'-(2,5-dimethyl-1,4-phenylene)bis(5-chlorobenzo[b]thiophene) (3-7)

6,6'-(2,5-dimethyl-1,4-phenylene)bis(5-chlorobenzo[b]thiophene-2-carboxylic acid) (8 g, 15.21 mmol) and copper powder (2.24 g, 35 mmol) were suspended in quinoline (120 mL) and heated at 185° C. overnight. After cooling down to rt, the mixture was filtered and the solid was washed with chloroform and the combined organic solutions was washed with 2 N HCl twice. The residue was purified by chromatography on silica with chloroform/hexane to afford a white solid. Yield: 5.53 g (83%)
$^1$H NMR (700 MHz, DMSO, 80° C.) δ 8.10 (s, 2H), 8.02 and 7.98 (2 s (rotamers), 2H), 7.85 (d, J=5.3 Hz, 2H), 7.48 (d, J=5.3 Hz, 2H), 7.13 (s, 2H), 2.07 (s, 6H).

Example 7

Synthesis of (J-8)

A mixture of 6,6'-(2,5-dimethyl-1,4-phenylene)bis(5-chlorobenzo[b]thiophene) (1 g, 2.28 mmol), Pd(OAc)$_2$ (0.15 g, 0.228 mmol), IPr.HCl (0.19 g, 0.456 mmol), K$_2$CO$_3$ (1.26 g, 9.12 mmol) and NMP (25 mL) in a 50 mL flask was purged with nitrogen for 5 min. The mixture was then kept in an oil bath at 170° C. overnight. After cooling to room temperature, the solution was extracted with chloroform and washed with water. The solvents of the organic phase were removed under reduced pressure. The residue was subjected to chromatography on silica gel, eluting with hexane/chloroform to afford a white solid. Yield: 0.69 g (83%)
$^1$H NMR (700 MHz, DMSO) δ 8.51 (s, 2H), 8.15 (s, 2H), 8.05 (s, 2H), 7.70 (d, J=5.3 Hz, 2H), 7.46 (d, J=5.3 Hz, 2H), 4.10 (s, 4H).

Example 8

Synthesis of Compound (J-9)

To a suspension of compound 8 (1 g, 2.73 mmol) in anhydrous DMSO (50 ml) was added sodium tert-butoxide (2.63 g, 27.3 mmol) in parts. The reaction mixture was heated at 80° C. for 1 h, followed by the addition of 1-bromohexadecane (5 g, 16.38 mmol) dropwise. After complete addition, the resultant mixture was heated at 85° C. for 12 h. After cooling to room temperature, water was added to quench the reaction, then the solution was extracted with dichloromethane and washed with water. The solvents of the organic phase were removed under reduced pressure. The residue was subjected to chromatography on silica gel, eluting with hexane to afford a light-yellow solid. Yield: 3.45 g (81%)

$^1$H NMR (700 MHz, CD$_2$Cl$_2$) δ 8.24 (s, 2H), 7.79 (s, 2H), 7.75 (s, 2H), 7.46 (d, J=5.3 Hz, 2H), 7.39 (d, J=5.3 Hz, 2H), 2.13-2.11 (m, 8H), 0.96-1.36 (m, 104H), 0.90-0.86 (m, 12H), 0.83-0.69 (m, 8H).

Example 9

Synthesis of Compound (J-10)

To a suspension of compound 8 (1 g, 2.73 mmol) in anhydrous DMSO (50 ml) was added sodium tert-butoxide (2.63 g, 27.3 mmol) in parts. The reaction mixture was heated at 80° C. for 1 h, followed by the addition of 2-Ethylhexyl bromide (3.16 g, 16.38 mmol) dropwise. After complete addition, the resultant mixture was heated at 85° C. for 12 h. After cooling to room temperature, water was added to quench the reaction, then the solution was extracted with dichloromethane and washed with water. The solvents of the organic phase were removed under reduced pressure. The residue was subjected to chromatography on silica gel, eluting with hexane to afford a light-yellow solid. Yield: 2.23 g (71%)

$^1$H NMR (700 MHz, CD$_2$Cl$_2$) δ 8.20 (s, 2H), 7.78-7.75 (m, 2H), 7.74 (d, J=3.1 Hz, 2H), 7.41 (d, J=5.3 Hz, 2H), 7.36-7.33 (d, 2H), 2.18-1.95 (m, 8H), 1.02-0.41 (m, 60H).

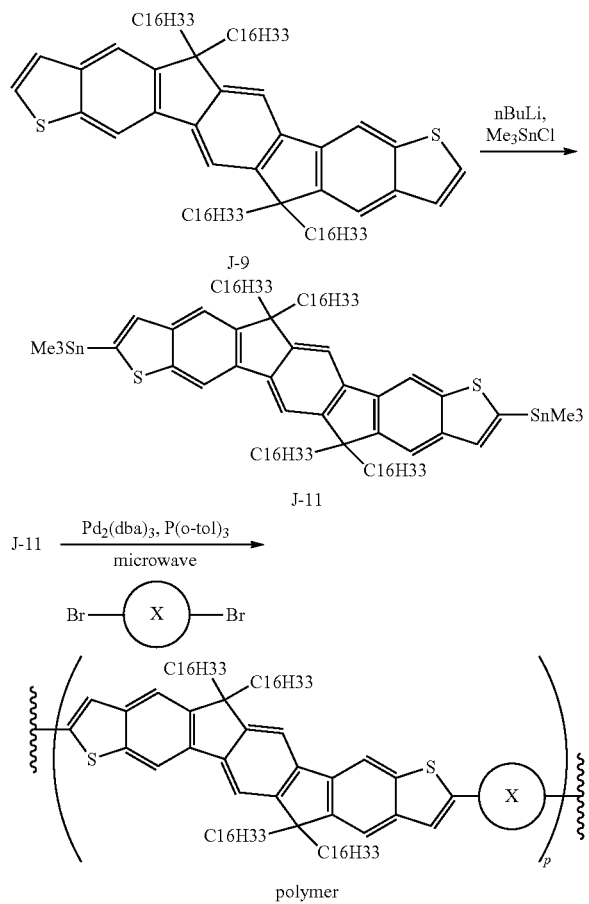

Scheme S2: Synthesis of polymers P-1 to P-4, starting from intermediate J-9

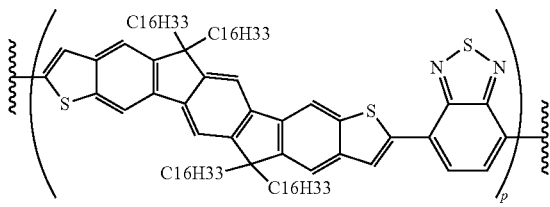

P-1

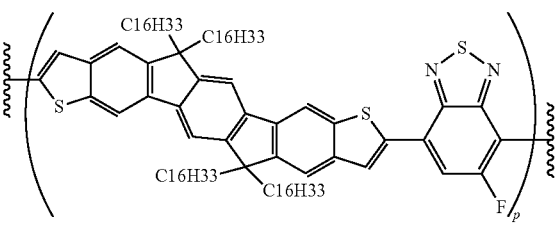

P-2

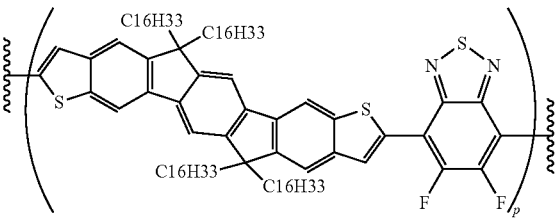

P-3

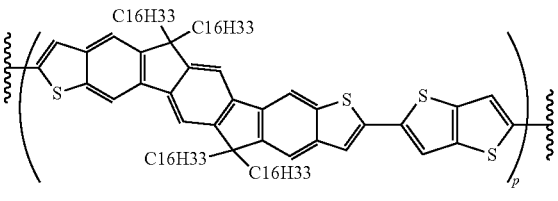

P-4

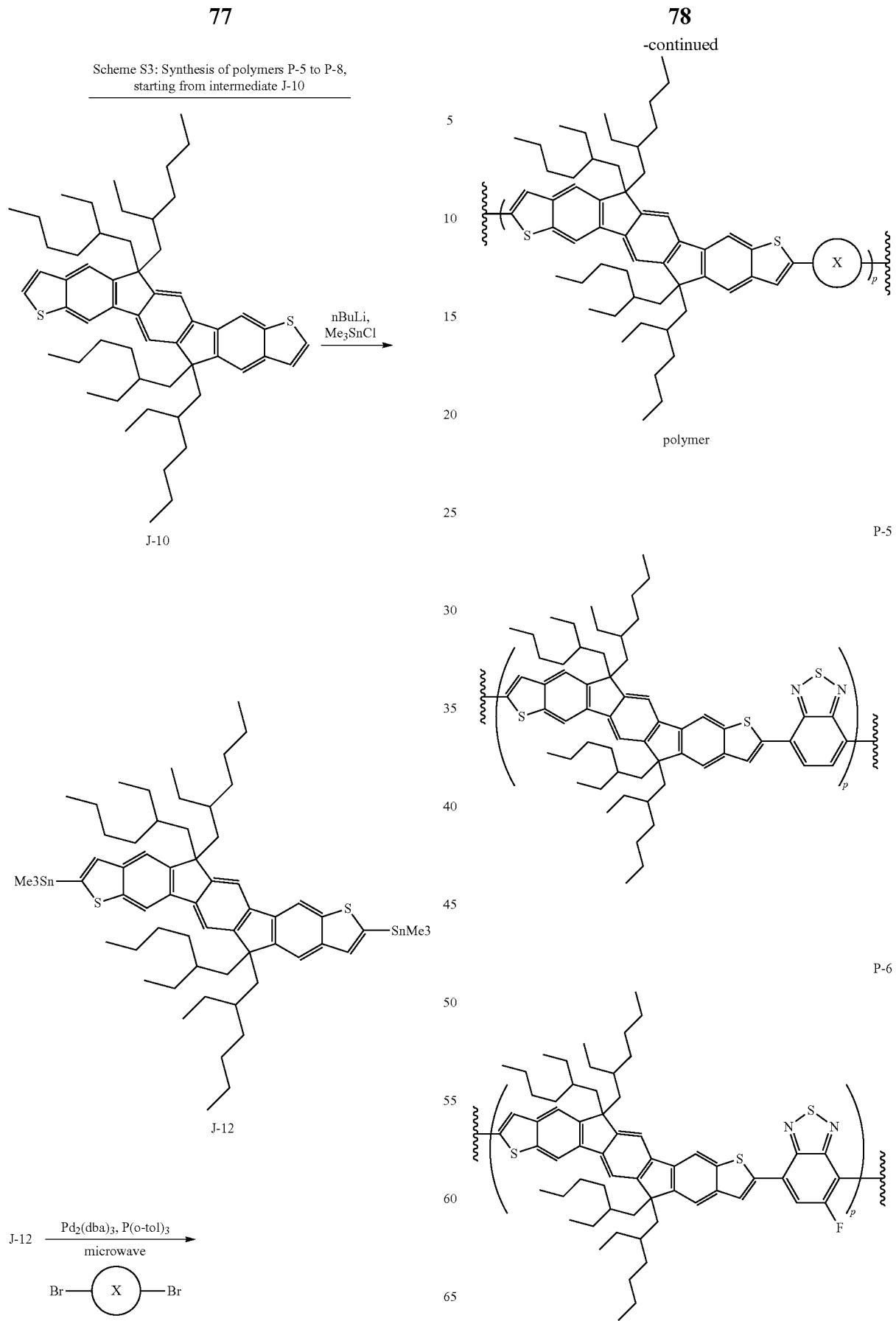

P-7

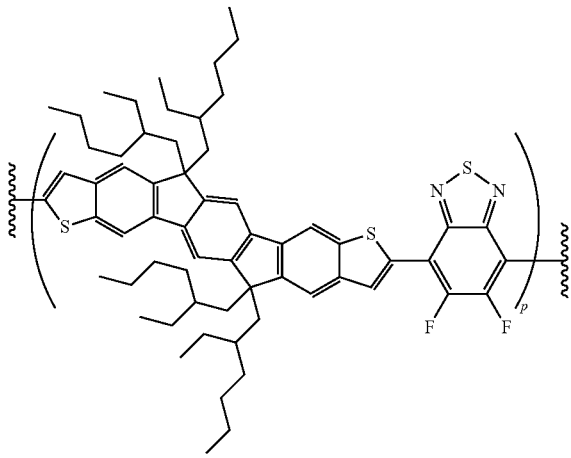

The used di-bromo-co-monomers are commercially available:

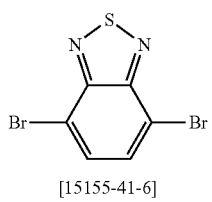
[15155-41-6]

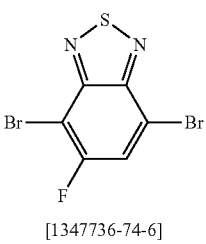
[1347736-74-6]

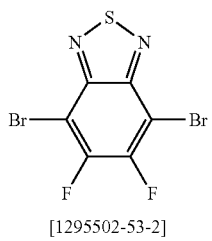
[1295502-53-2]

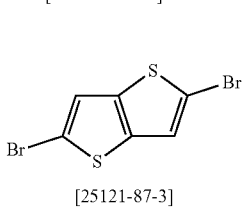
[25121-87-3]

Example 10

Synthesis of Intermediate (J-11)

To a suspension of compound J-9 (1 g, 0.79 mmol) in anhydrous THF (30 ml) and cooled to −78° C., then nBuLi (2.73 mmol) was added dropwisely. The reaction mixture was stirred at −78° C. for 1 h, then the temperature was rised to room temperature and cooled again to −10° C. followed by the addition of Me$_3$SnCl (2.73 mmol) dropwise. After complete addition, the resultant mixture was slowly warmed up to rt and stirred overnight. Water was added to quench the reaction, then the solution was extracted with ethyl acetate and concentrated. The mixture was subjected to chromatography on Al$_2$O$_3$, eluting with hexane to afford J-11 as a light-yellow oil. Yield: 1.09 g (87%) $^1$H NMR (500 MHz, CD$_2$Cl$_2$) δ 8.23 (s, 2H), 7.76 (s, 2H), 7.73 (s, 2H), 7.45 (s, 2H), 2.13-2.11 (m, 8H), 0.96-1.36 (m, 104H), 0.90-0.86 (m, 12H), 0.83-0.69 (m, 8H), 0.44 (t, 18H).

Example 11

Synthesis of Intermediate (J-12)

To a suspension of compound J-10 (0.64 g, 0.79 mmol) in anhydrous THF (30 ml) and cooled to −78° C., then nBuLi (2.73 mmol) was added dropwisely. The reaction mixture was stirred at −78° C. for 1 h, then the temperature was rised to room temperature and cooled again to −10° C. followed by the addition of Me$_3$SnCl (2.73 mmol) dropwise. After complete addition, the resultant mixture was slowly warmed up to rt and stirred overnight. Water was added to quench the reaction, then the solution was extracted with ethyl acetate and concentrated. The mixture was subjected to chromatography on Al$_2$O$_3$, eluting with hexane to afford a light-yellow solid. Yield: 0.77 g (85%)

$^1$H NMR (500 MHz, CD$_2$Cl$_2$) δ 8.24 (s, 2H), 7.77 (s, 2H), 7.75 (s, 2H), 7.48 (s, 2H), 2.13-1.36 (m, 8H), 0.90-0.69 (m, 60H), 0.44 (t, 18H).

Examples 12-19

Synthesis of Polymers P-1 to P-8

A 2.5 mL microwave vial was charged with bis(trimethylstannyl) monomer J-10 or J-12 (0.233 mmol), 1 eq. of dibrominated monomer (corresponding (fluorinated)benzothiadiazole or thienothiophene), 2 mol % of tris(dibenzylideneacetone)dipalladium(0) and 8 mol % of tri(o-tolyl) phosphine. The vial was sealed and chlorobenzene (1 mL) was added. The obtained solution was degassed with argon during 30 minutes. The vial was subjected to the following reaction conditions in the microwave reactor: 2 minutes at 100° C., 2 minutes at 120° C., 5 minutes at 140° C., 5 minutes at 160° C. and 40 minutes at 180° C. The polymer was end-capped by addition of 0.1 eq. of 2-bromothiophene before the reaction mixture was resubmitted to the microwave reactor, 1 minute at 100° C., 1 minute at 120° C., 2 minutes at 140° C. and 5 minutes at 160° C. The polymeric solution was cooled down and 0.1 eq. of 2-(trimethylstannyl)thiophene was added by syringe. The reaction vial was subjected to the previously mentioned temperature scheme to finalize the end-capping reaction. After reaction, the crude polymer was precipitated in methanol and then further purified by Soxhlet extractions with acetone, hexane and chloroform during 24 hours each. Remaining palladium residues were removed by treating a polymeric chloroform solution with an aqueous sodium diethyldithiocarbamate solution for 2 hours at 50° C. under vigorous stirring. Afterwards the organic phase was separated from the aqueous phase and washed several times with water. The polymeric solution was concentrated under reduced pressure and precipitated into cold methanol. The polymer was filtered off and dried under high vacuum for at least 24 hours.

Polymer P-1: $^1$H NMR (500 MHz, CDCl$_3$) δ 8.73 (br, 2H), 8.27 (br, 2H), 8.03 (br, 2H), 7.88 (br, 2H), 7.76 (br, 2H), 2.13-2.11 (br, 8H), 0.96-1.36 (br, 104H), 0.90-0.86 (br, 12H), 0.83-0.69 (br, 8H);

Polymer P-2: $^1$H NMR (500 MHz, CDCl$_3$) δ 8.77 (br, 2H), 8.71 (br, 2H), 8.28 (br, 3H), 7.90 (br, 2H), 7.77 (br, 2H), 2.13-2.11 (br, 8H), 0.96-1.36 (br, 104H), 0.90-0.86 (br, 12H), 0.83-0.69 (br, 8H);

Polymer P-3: $^1$H NMR (500 MHz, CDCl$_3$) δ 8.75 (br, 2H), 8.32 (br, 2H), 7.93 (br, 2H), 7.79 (br, 2H), 2.13-2.11 (br, 8H), 0.96-1.36 (br, 104H), 0.90-0.86 (br, 12H), 0.83-0.69 (br, 8H);

Polymer P-4: $^1$H NMR (500 MHz, CDCl$_3$) δ 8.14 (br, 2H), 7.69 (br, 4H), 7.49 (br, 2H), 7.46 (br, 2H), 2.13-2.11 (br, 8H), 0.96-1.36 (br, 104H), 0.90-0.86 (br, 12H), 0.83-0.69 (br, 8H);

Polymer P-5: $^1$H NMR (500 MHz, CDCl$_3$) δ 8.74 (br, 2H), 8.27 (br, 2H), 8.02 (br, 2H), 7.86 (br, 2H), 7.74 (br, 2H), 2.13-2.11 (br, 8H), 0.96-1.36 (br, 104H), 0.90-0.86 (br, 12H), 0.83-0.69 (br, 8H), 0.44-0.48 (br, 18H);

Polymer P-6: $^1$H NMR (500 MHz, CDCl$_3$) δ 8.76 (br, 2H), 8.73 (br, 2H), 8.25 (br, 3H), 7.93 (br, 2H), 7.77 (br, 2H), 2.13-2.11 (br, 8H), 0.96-1.36 (br, 104H), 0.90-0.86 (br, 12H), 0.83-0.69 (br, 8H), 0.44-0.48 (br, 18H);

Polymer P-7: $^1$H NMR (500 MHz, CDCl$_3$) δ 8.75 (br, 2H), 8.34 (br, 2H), 7.92 (br, 2H), 7.79 (br, 2H), 2.13-2.11 (br, 8H), 0.96-1.36 (br, 104H), 0.90-0.86 (br, 12H), 0.83-0.69 (br, 8H), 0.44-0.48 (br, 18H);

Polymer P-8: $^1$H NMR (500 MHz, CDCl$_3$) δ 7.95 (br, 2H), 7.83 (br, 2H), 7.71 (br, 2H), 7.40 (br, 2H), 7.23 (br, 2H), 2.13-2.11 (br, 8H), 0.96-1.36 (br, 104H), 0.90-0.86 (br, 12H), 0.83-0.69 (br, 8H), 0.44-0.48 (br, 18H).

GPC Data:

| Polymer | Mn KDa | Mw KDa | PDI |
|---|---|---|---|
| P-1 | 41.6 | 56.6 | 1.36 |
| P-2 | 55.2 | 82.7 | 1.50 |
| P-3 | 49.0 | 74.2 | 1.51 |
| P-4 | 29.8 | 60.9 | 2.04 |
| P-5 | 169.5 | 327.0 | 1.93 |
| P-6 | 60.0 | 129.1 | 2.15 |
| P-7 | 59.3 | 140.9 | 2.37 |
| P-8 | 69.5 | 181.6 | 2.61 |

Scheme S4: Synthesis of intermediate corresponding to formula J-18

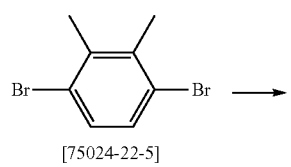

[75024-22-5]

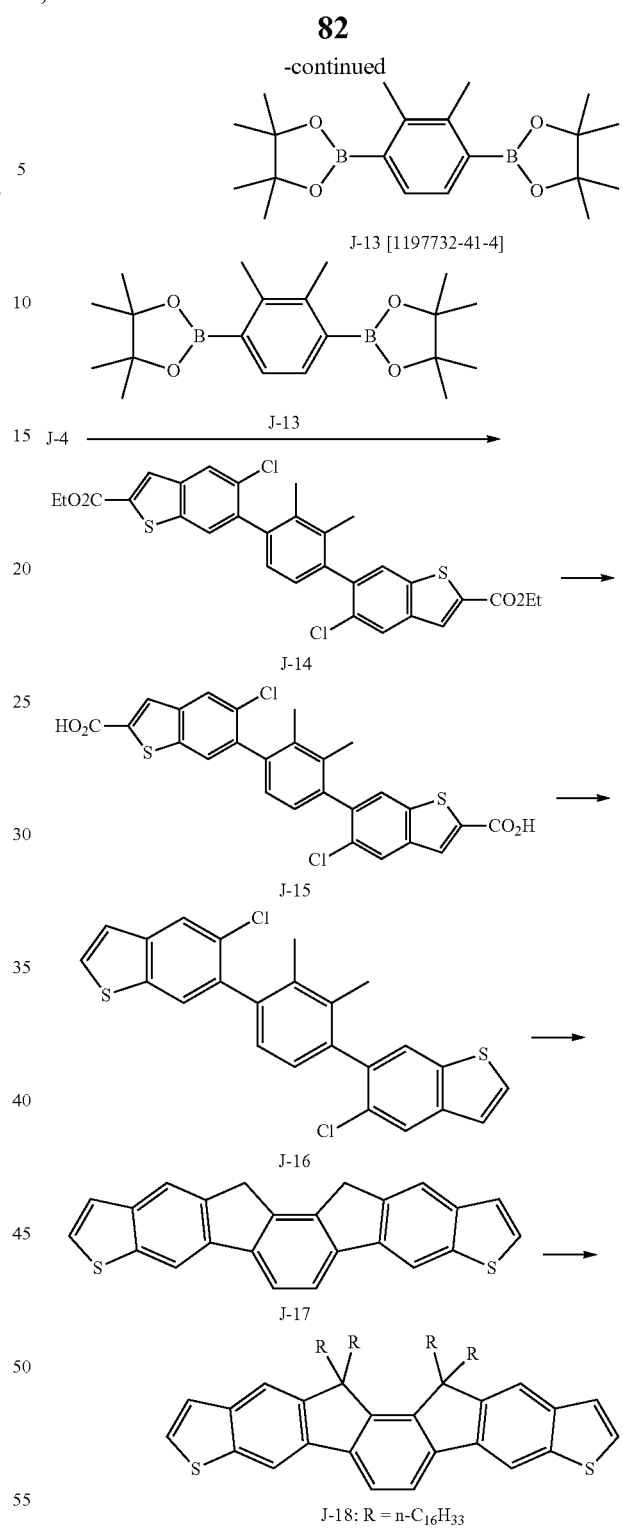

Example 20

Synthesis of Intermediate (J-13)

Intermediate J-13 can be obtained commercially [1197732-41-4] or by literature described methods from 1,4-dibromo-2,3-dimethyl-benzene [75024-22-5].

Example 21

Synthesis of Intermediate (J-14)

56.3 mmol (18.0 g) of compound J-4, 28.15 mmol (9.604 g) of compound J-13, 0.67 mmol (0.633 g) tris-(dibenzylideneacetone)-dipalladium(0) [51364-51-3] and 1.61 mmol (0.481 g) tri-tertbutyl-phosphonium-tetrafluoroborate [131274-22-1] were added to a 250 ml 3-necked-flask equipped with a thermometer, reflux condenser with argon inlet and a septum. The system was evacuated and refilled with argon two times. Then 150 ml of dry and degassed tetrahydrofuran was added to the reaction flask. After dissolution of the starting material at 50° C., a degassed solution of 83 mmol (18 g) potassium phosphate in 3.8 ml of water was added and the reaction mixture was heated to reflux and stirred for 4 hours. The reaction mixture was allowed to cool to rt over night, where the product precipitated. The reaction mixture was filtered, washed with THF and then with water and then dried to give the crude J-14 which was used directly in the next step.

$^1$H NMR (400 MHz, CDCl$_3$) δ 8.06 (s, 2H), 8.02 (s, 2H), 7.86 and 7.79 (2 s (rotamers), 2H), 7.13 (s, 2H), 4.45 (q, 4H), 2.13 (s, 6H), 1.46 (t, 6H).

Example 22

Synthesis of Intermediate (J-15)

20 mmol (11.5 g) of compound J-14 was suspended in 300 ml of ethanol, and then a solution of 5.5 g of KOH in 20 ml of water was added to the suspension. The suspension was then refluxed over night. The suspension was cooled to rt and then poured into 4 M HCl. The precipitate was filtered and washed well with water and then dried to give crude J-15 which was used directly in the next step.

$^1$H NMR (400 MHz, DMSO-D$_6$) δ 8.28 (s, 2H), 8.15 (s, 2H), 8.10 and 8.06 (2 s (rotamers), 2H), 7.13 (s, 2H), 2.06 (s, 6H).

Example 23

Synthesis of Intermediate (J-16)

11.82 mmol (6.400 g) of compound J-15 was suspended in 25 ml of quinoline. Then 1.728 g of copper powder was added and the reaction mixture was heated for 8 hours at 185° C. The copper was allowed to settle to the bottom of the flask, and the solution was decanted and the product precipitated with ethanol to give crude J-16 which was used directly in the next step.

$^1$H NMR (400 MHz, DMSO-D$_6$) δ 8.14 (s, 2H), 8.05 and 8.01 (2 s (rotamers), 2H), 7.90 (d, 2H), 7.51 (d, 2H), 7.11 (s, 2H), 2.06 (s, 6H).

Example 24

Synthesis of Intermediate (J-17)

7.282 mmol (3.20 g) of compound J-16, 29.129 mmol (4.066 g) potassium carbonate, 0.728 mmol (0.163 g) palladium(II)acetate and 1.456 mmol (0.619 g) 1,3-Bis(2,6-diisopropylphenyl)imidazoliumchloride [250285-32-6] have been loaded to a 50 ml 3-necked-flask equipped with a thermometer, reflux condenser with argon inlet and a septum. Then 20 ml of anhydrous N-methylpyrrolidone were added under nitrogen and the reaction mixture was stirred for 7 hours at 170° C. Then the mixture was cooled to rt and water was added. The precipitate was filtered and washed with water and then dried to give crude J-17, which was used directly in the next step. The product was too insoluble to measure an NMR.

Example 25

Synthesis of Intermediate (J-18)

3.82 mmol (1.46 g) of compound J-17 were suspended in 20 ml of dry dimethylsulfoxide. Then 38 mmol (3.67 g) of sodium tert-butoxide were added under nitrogen. The reaction mixture was heated to 85° C. for 1 hour. Then a solution of 23 mmol (8.075 g) 1-iodohexadecane in 5 ml of dimethylsulfoxide was added over a period of 2 hours. The reaction mixture was stirred over night at 85° C. The mixture was cooled to rt and water was added. The mixture was then extracted with heptane. The heptane solution was washed with water and dried over MgSO$_4$ and then the solvent was evaporated. The product was purified by column chromatography on silica gel. Then the product was recrystallized from ethyl acetate to get compound J-18. $^1$H NMR (400 MHz, CDCl$_3$) δ 8.18 (s, 2H), 7.85 (s, 2H), 7.69 (s, 2H), 7.44 (d, 2H), 7.39 (d, 2H), 2.46 (br t, 4H), 2.10 (br t, 4H), 1.35-1.02 (m, 104H), 0.90 (t, 12H), 0.62-0.58 (br, 8H).

Scheme S5: Synthesis of polymer P-9 starting from intermediate J-18

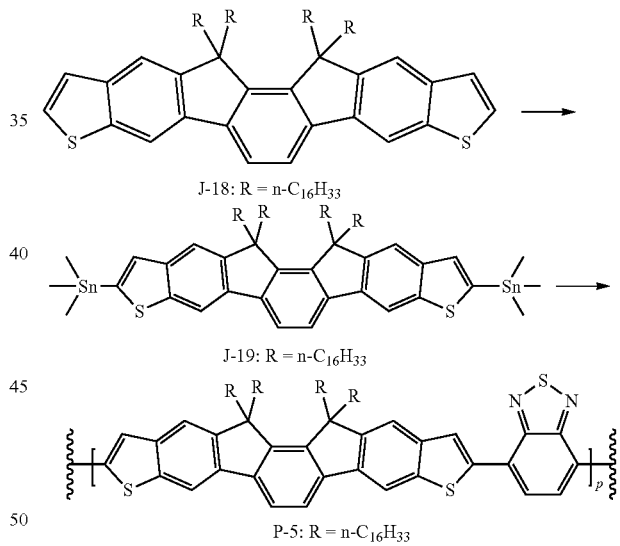

J-18: R = n-C$_{16}$H$_{33}$

J-19: R = n-C$_{16}$H$_{33}$

P-5: R = n-C$_{16}$H$_{33}$

Example 26

Synthesis of Intermediate (J-19)

0.791 mmol (1.0 g) of compound J-18 were added to a 100 ml 3-necked-flask equipped with a thermometer, reflux condenser with argon inlet and a septum. The system was evacuated and refilled with argon two times. Then 50 ml of dry and degassed tetrahydrofuran was added to the reaction flask. After dissolution of the starting material, the temperature was lowered to −78° C. Then 2.689 mmol (0.996 ml) of 2.7M n-butyllithium solution in heptane were added slowly via a syringe. After stirring for 15 minutes, the reaction mixture was allowed to come to room temperature for 1 hour. Then the temperature was reduced to −20° C. and 2.689 mmol (2.689 ml) of 1M trimethyltinchloride solution in (in hexanes) were added via a syringe. The reaction mixture was stirred then overnight at room temperature. The reaction was quenched by the addition of water and the product was extracted with ethylacetate. The organic phase was dried over $MgSO_4$ and evaporated. The residue was recrystallized from ethyl acetate and then from heptane to yield 400 mg of compound J-19.

$^1$H NMR (400 MHz, $CD_2Cl_2$) δ 8.21 (s, 2H), 7.88 (s, 2H), 7.73 (s, 2H), 7.50 (s, 2H), 2.50 (br t, 4H), 2.13 (br t, 4H), 1.35-1.04 (m, 104H), 0.90 (t, 12H), 0.64-0.55 (br, 8H), 0.49 (t, 18H).

Example 27

Synthesis of Polymer (P-9)

0.019 mmol (30.2 mg) of compound J-19 and 0.019 mmol (5.6 mg) of 4,7-dibromo-benzo[c]-1,2,5-thiadiazole [15155-41-6], 0.001 mmol (0.9 mg) of tris-(dibenzylideneacetone)-dipalladium(0) [51364-51-3] and 0.004 mmol (1.2 mg) of tri-(o-tolyl)-phosphine [6163-58-2] were charged to a 10 ml 3-necked-flask equipped with a thermometer, reflux condenser with argon inlet and a septum. The system was evacuated and refilled with argon for five times. Via a syringe 2 ml of degassed chlorobenzene was added. The reaction mixture was then brought to reflux for 22 hours. The reaction mixture turned to intense red color. The reaction mixture was added to 20 ml of acetone, where the polymer precipitated. The polymer was filtered and the residue washed with acetone. The polymer was taken up into toluene and refluxed for 3 hours with an aqeuous solution of sodium-diethyl-dithiocarbamate to remove Pd residues. The solution was cooled to rt, separated the phases and the organic phase was washed twice with deionized water. The toluene phase was added to aceton to precipitate the polymer once again. After filtration, the polymer was added to a soxhlet thimble and extracted first with acetone, then hexanes, and finally with toluene. The aceton fraction contained no polymer. The hexanes and toluene fractions were added to aceton, where the polymer precipitated. The hexane fraction yielded 22 mg of the polymer P-9 (GPC data (trichlorobenzene, 150° C.): Mw 32'665 PDI 2.21), and the toluene fraction yielded 7 mg of the polymer P-9.

Scheme S6: Synthesis of intermediate corresponding to formula J-25

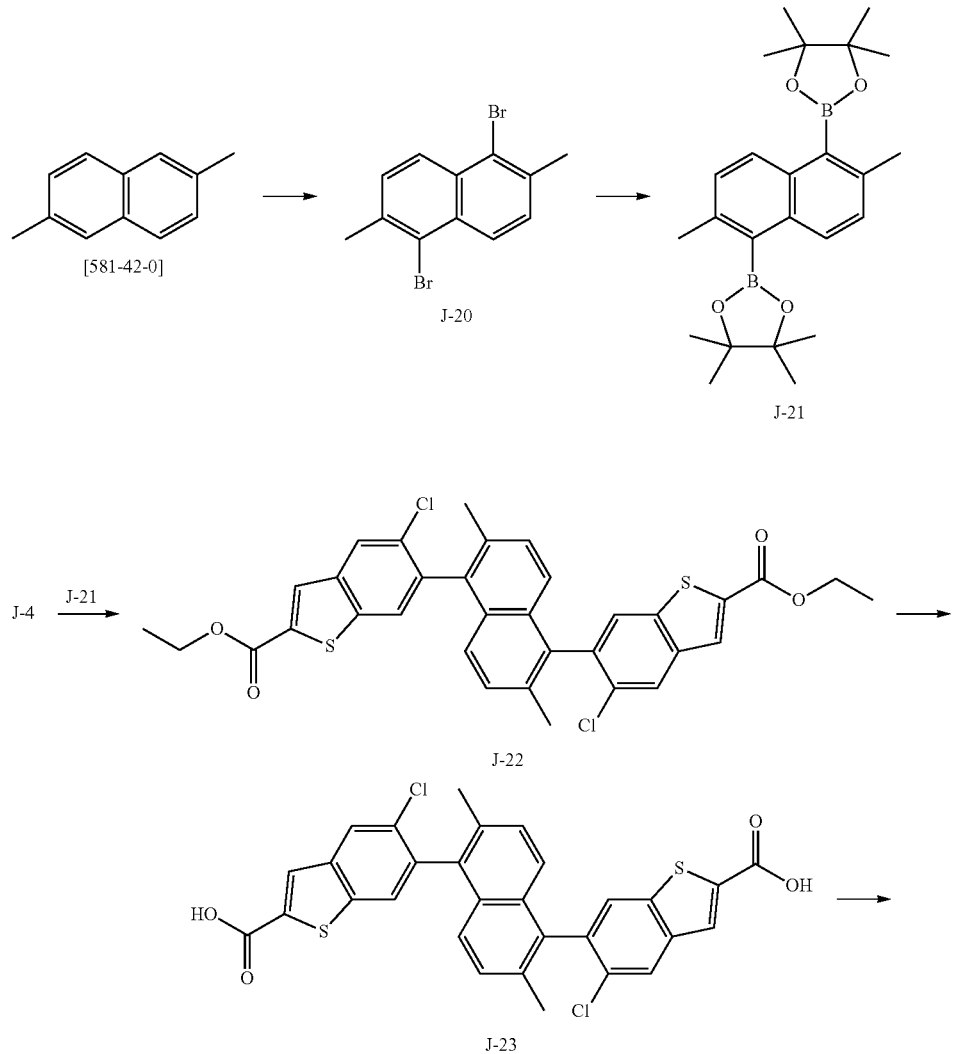

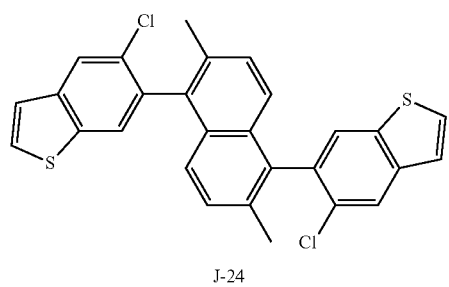

J-24

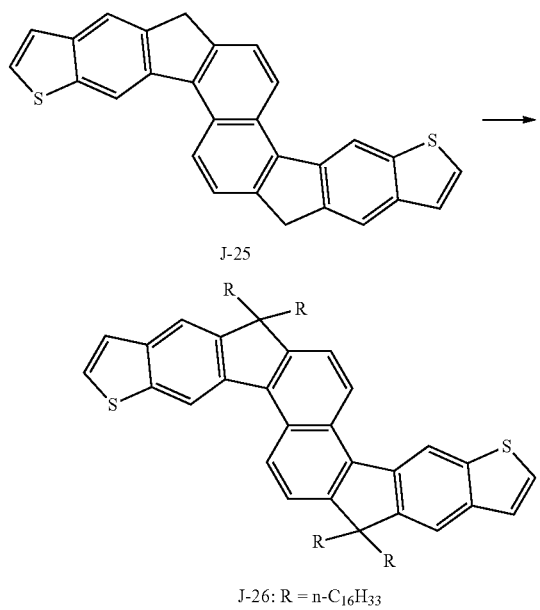

J-25

J-26: R = n-C$_{16}$H$_{33}$

Example 28

Synthesis of Intermediate (3-20)

64 mmol (10.0 g) of 2,6-dimethylnaphthalene were dissolved in 100 ml dichloromethane and 20 mg of iodine were added. 139 mmol (22.21 g) bromine were added dropwise over 7 hours at 21° C. The mixture was then stirred over night at rt. The organic phase was washed with aqeuous sodiumthiosulphate and water, dried and evaporated. The crude product was recrystallized from ethanol to give compound J-20.
$^1$H NMR (400 MHz, CDCl$_3$) δ 8.22 (d, 2H), 7.44 (d, 2H), 2.65 (s, 6H).

Example 29

Synthesis of Intermediate (J-21)

33.4 mmol (10.50 g) of compound J-20, 94.5 mmol (24.00 g) bis(pinacolato)diborone [73183-34-3], 268 mmol (26.52 g) potassium acetate and 2.006 mmol (1.47 g) Pd(dppf)Cl$_2$ [72287-26-4] were placed in a 250 ml 3-necked-flask equipped with a thermometer, reflux condenser with argon inlet and a septum. The system was evacuated and refilled with argon for five times. Via a syringe 80 ml of degassed dimethylformamide was added. The reaction mixture was then heated and stirred at 110° C. for 48 hours. The mixture was cooled to rt, and water was added and the product was extracted with heptane. The organic phase was dried and evaporated. The product was recrystallized from isopropanol to get compound J-21.
$^1$H NMR (400 MHz, CDCl$_3$) δ 8.03 (d, 2H), 7.27 (d, 2H), 2.60 (s, 6H), 1.49 (s, 24H).

Example 30

Synthesis of Intermediate (J-22)

Intermediate J-22 was synthesized from compound J-4 and J-21 according to compound J-14 described in example 21.
$^1$H NMR (300 MHz, DMSO-D$_6$) δ 8.41 (s, 2H), 8.29 (s, 2H), 8.18 and 8.09 (2 s (rotamers), 2H), 7.40 (d, 2H), 7.12 (d, 2H), 4.40 (q, 4H), 2.10 (s, 6H), 1.37 (t, 6H).

Example 31

Synthesis of Intermediate (J-23)

Intermediate J-23 was synthesized from compound J-22 according to compound J-15 described in example 22.
$^1$H NMR (300 MHz, DMSO-D$_6$) δ 8.40 (s, 2H), 8.21 (s, 2H), 8.08 (s, 2H), 7.39 (d, 2H), 7.13 (d, 2H), 2.12 (s, 6H).

Example 32

Synthesis of Intermediate (J-24)

Intermediate J-24 was synthesized from compound J-23 according to compound J-16 described in example 23.
$^1$H NMR (300 MHz, DMSO-D$_6$) δ 8.25 (s, 2H), 8.09 and 8.00 (2 s (rotamers), 2H), 7.94 (d, 2H), 7.57 (d, 2H), 7.37 (d, 2H), 7.13 (d, 2H), 2.12 (s, 6H).

Example 33

Synthesis of Intermediate (J-25)

Intermediate J-25 was synthesized from compound J-24 according to compound J-17 described in example 24.
$^1$H NMR (400 MHz, DMSO-D$_6$) δ 9.23 (s, 2H), 9.02 (d, 2H), 8.16 (s, 2H), 7.99 (d, 2H), 7.81 (d, 2H), 7.52 (d, 2H), 4.24 (s, 4H).

Example 34

Synthesis of Intermediate (J-26)

Intermediate J-26 was synthesized from compound J-25 according to compound J-18 described in example 25.

$^1$H NMR (300 MHz, CDCl$_3$) δ 8.89 (d, 2H), 8.87 (s, 2H), 7.86 (s, 2H), 7.73 (d, 2H), 7.50 (d, 2H), 7.42 (d, 2H), 2.19-2.11 (br, 8H), 1.35-0.95 (m, 104H), 0.89 (t, 12H), 0.75-0.60 (br, 8H).

Scheme S7: Synthesis of polymer P-10 starting from intermediate J-26

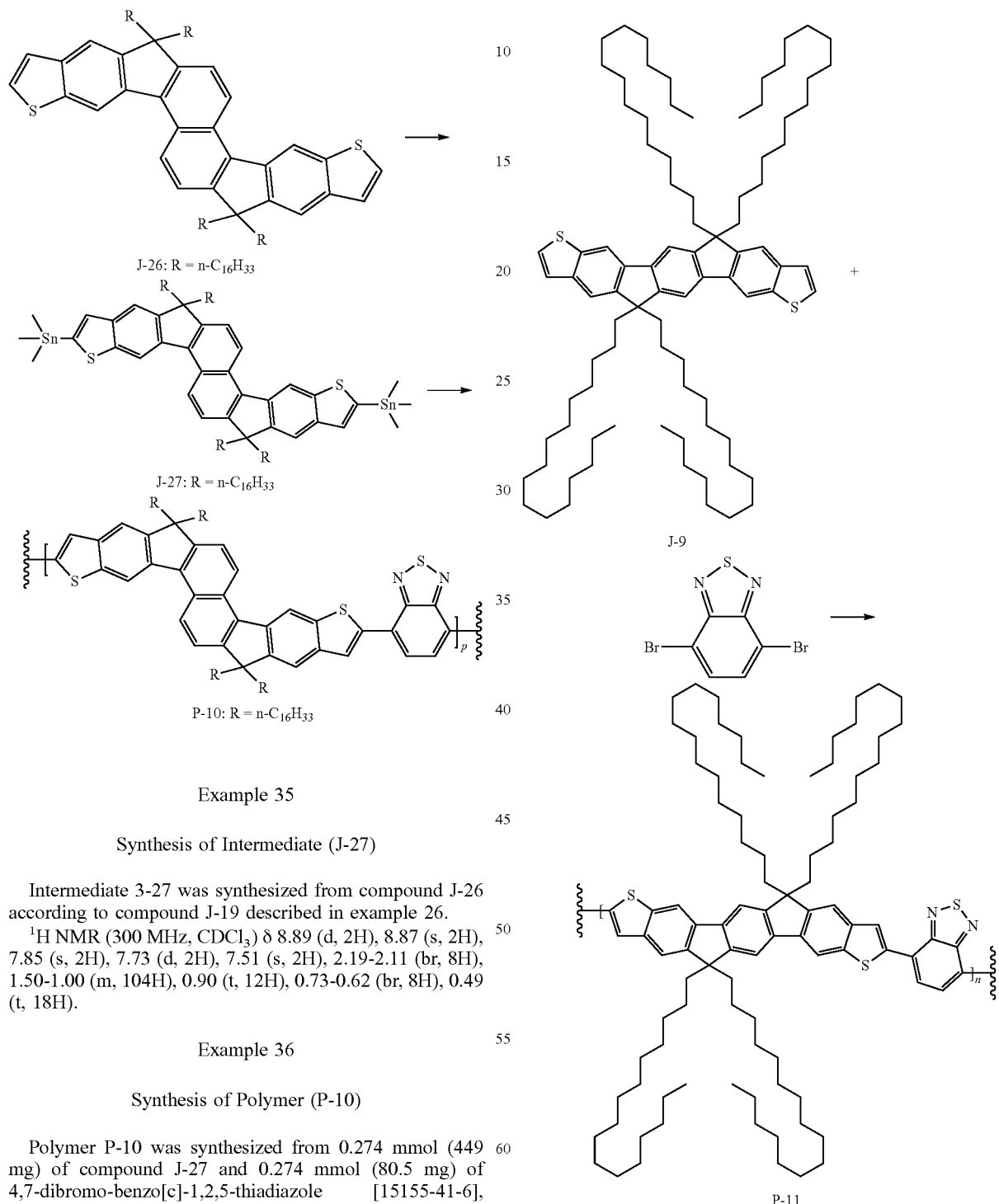

J-26: R = n-C$_{16}$H$_{33}$

J-27: R = n-C$_{16}$H$_{33}$

P-10: R = n-C$_{16}$H$_{33}$

Example 35

Synthesis of Intermediate (J-27)

Intermediate 3-27 was synthesized from compound J-26 according to compound J-19 described in example 26.

$^1$H NMR (300 MHz, CDCl$_3$) δ 8.89 (d, 2H), 8.87 (s, 2H), 7.85 (s, 2H), 7.73 (d, 2H), 7.51 (s, 2H), 2.19-2.11 (br, 8H), 1.50-1.00 (m, 104H), 0.90 (t, 12H), 0.73-0.62 (br, 8H), 0.49 (t, 18H).

Example 36

Synthesis of Polymer (P-10)

Polymer P-10 was synthesized from 0.274 mmol (449 mg) of compound J-27 and 0.274 mmol (80.5 mg) of 4,7-dibromo-benzo[c]-1,2,5-thiadiazole [15155-41-6], according to polymer P-9 described in example 27. Soxhlet extraction gave 79 mg polymer P-10 from hexane fraction (GPC data (trichlorobenzene, 150° C.): Mw 27'139, PDI 2.23) and 257 mg polymer P-10 from toluene fraction (GPC data (trichlorobenzene, 150° C.): Mw 78'162, PDI 2.28).

Example 37

Synthesis of Polymer P-11 (Same Structure as Polymer P-1 Above) Via Direct Heteroarylation Polymerization

J-9

P-11

0.032 mmol (40 mg) of compound J-9 and 0.032 mmol (12 mg) of 4,7-dibromo-benzo[c]-1,2,5-thiadiazole [15155-41-6] were placed together with 10% Pd(Herrmann) catalyst and 15% tri(ortho-methoxy-phenyl)phosphine, 2 equivalents of pivalic acid, 3 equivalents of potassiumcarbonate and 2 ml dimethylacetamide in a vial and degassed with argon. Then the reaction mixture was heated and stirred vigorously for 48 hours at 140° C. The polymer P-11 was precipitated with water, filtered and washed with water. Then the polymer was purified and fractionated in analogy to experiments 12-19 described above. The chloroform fraction gave a polymer P-11 with the following GPC data (chlorobenzene at 80° C.): Mw 52'300, PDI 1.41.

Application Examples A-1 to A-4

Fabrication and electrical characterization of organic field-effect transistors (OFET) based on the polymers P-1, P-2, P-3, and P-4

The polymers are dissolved at a concentration of 0.75 wt % in dichlorobenzene. Back-contact, Top-gate FETs are fabricated from each formulation according to the following procedure:

A PEN-substrate with lithographically pre-patterned gold contacts, serving as source and drain contact of the FET are used as substrates. 100 µl of the formulation is coated by a standard blade coater yielding a homogenous layer of the semiconductor over the entire substrate. After the coating is completed, the substrate is immediately transferred onto a preheated hotplate and heated for 30 s at 90° C. Next the gate dielectric layer consisting of Polystyrene 4 wt % dissolved in PGMEA is spin-coated on top of the organic semiconductor (2500 rpm, 30 s). After spin-coating of the dielectric, the substrate is again transferred to the hotplate and annealed for another 5 Min at 90° C. The thickness of the dielectric layer is 420 nm measured by profilometer. Finally 50 nm thick, shadow-mask patterned gold gate electrodes are deposited by vacuum evaporation to complete FETs in the BCTG-configuration.

The mobility µ is calculated from the root representation of the transfer characteristic curve (solid grey curve) in the saturation region. The slope m is determined from the dashed black line in the respective transfer characteristics. The dashed black line is fitted to a region of the square root representation of the drain current ID such that a good correlation to the linear slope of the root representation is obtained.

The threshold voltage $U_{Th}$ can be taken from the intersection of black dashed line with the X-axis portion ($V_{GS}$).

In order to calculate the electrical properties of the OFET, the following equations are employed:

$$\mu = \frac{m^2 * 2L}{C_G * W} \quad C_G = \varepsilon_0 * \varepsilon_r \frac{1}{d} \quad U_{Th} = -1 * \frac{m}{b} \quad ON/OFF = \frac{I_D max}{I_D min}$$

where $\varepsilon_0$ is the vacuum permittivity of $8.85 \times 10^{-12}$ As/Vm. $\varepsilon_r=2,6$ for Polystyrene and d is the thickness of the dielectric. The width over length ratio W/L is 10.

Figure 1:
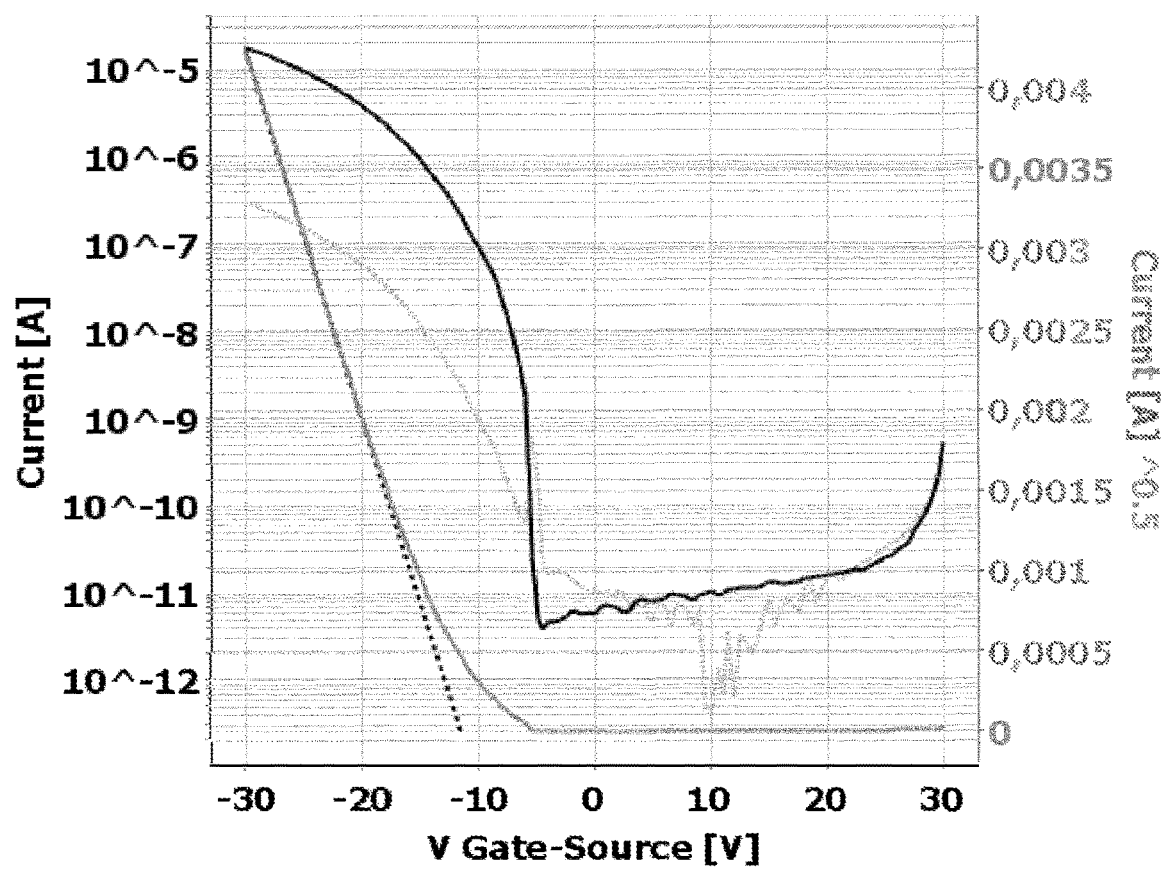
FIG. 1 show representative transfer characteristics of an FET fabricated from polymer P-1 with $V_{GS}$=30 V to −30 V at 0.5 V step size with $V_{DS}$=−30 V. Drain current (black solid curve), Gate current (dotted grey curve), Square root of drain current (grey solid curve), and fitted slope of square root (dashed black curve).
Figure 2:
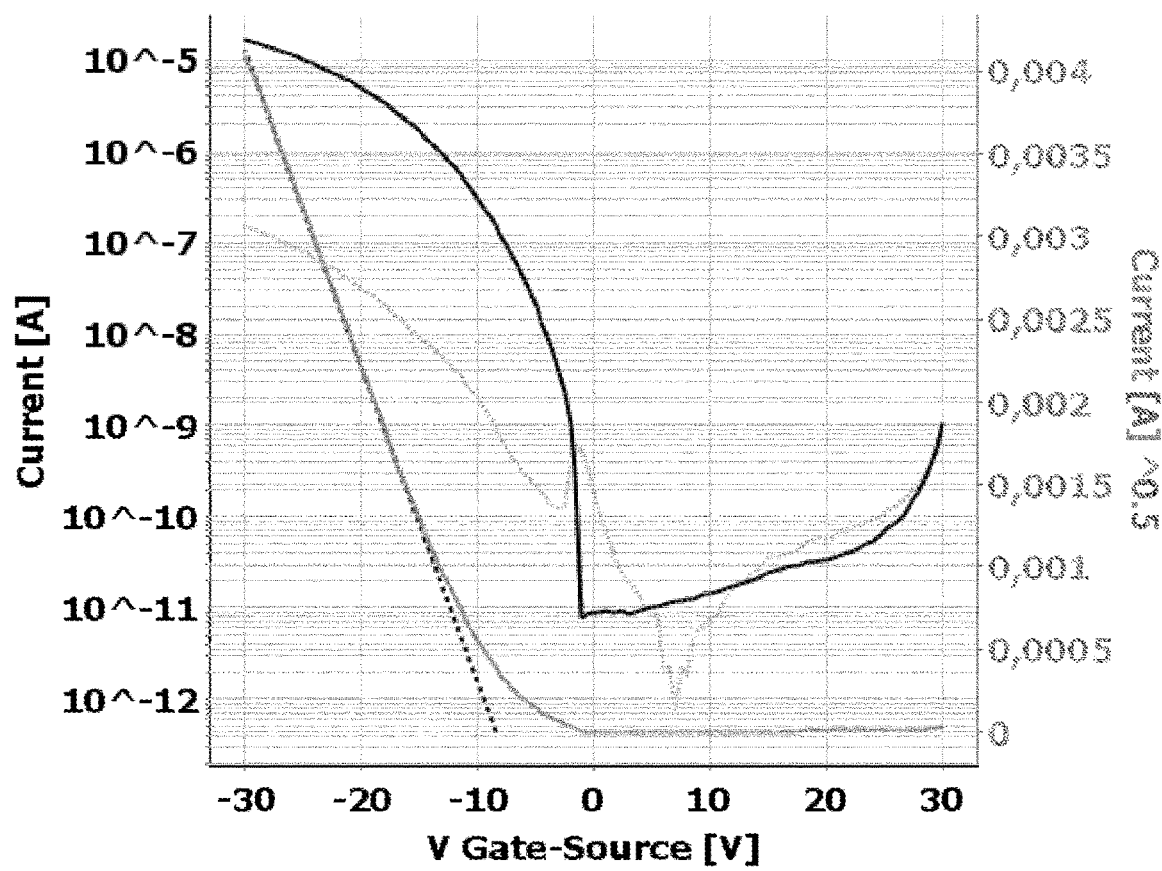
FIG. 2 show representative transfer characteristics of an FET fabricated from polymer P-2 with $V_{GS}$=30 V to −30 V at 0.5 V step size with $V_{DS}$=−30 V. Drain current (black solid curve), Gate current (dotted grey curve), Square root of drain current (grey solid curve), and fitted slope of square root (dashed black curve).
Figure 3:
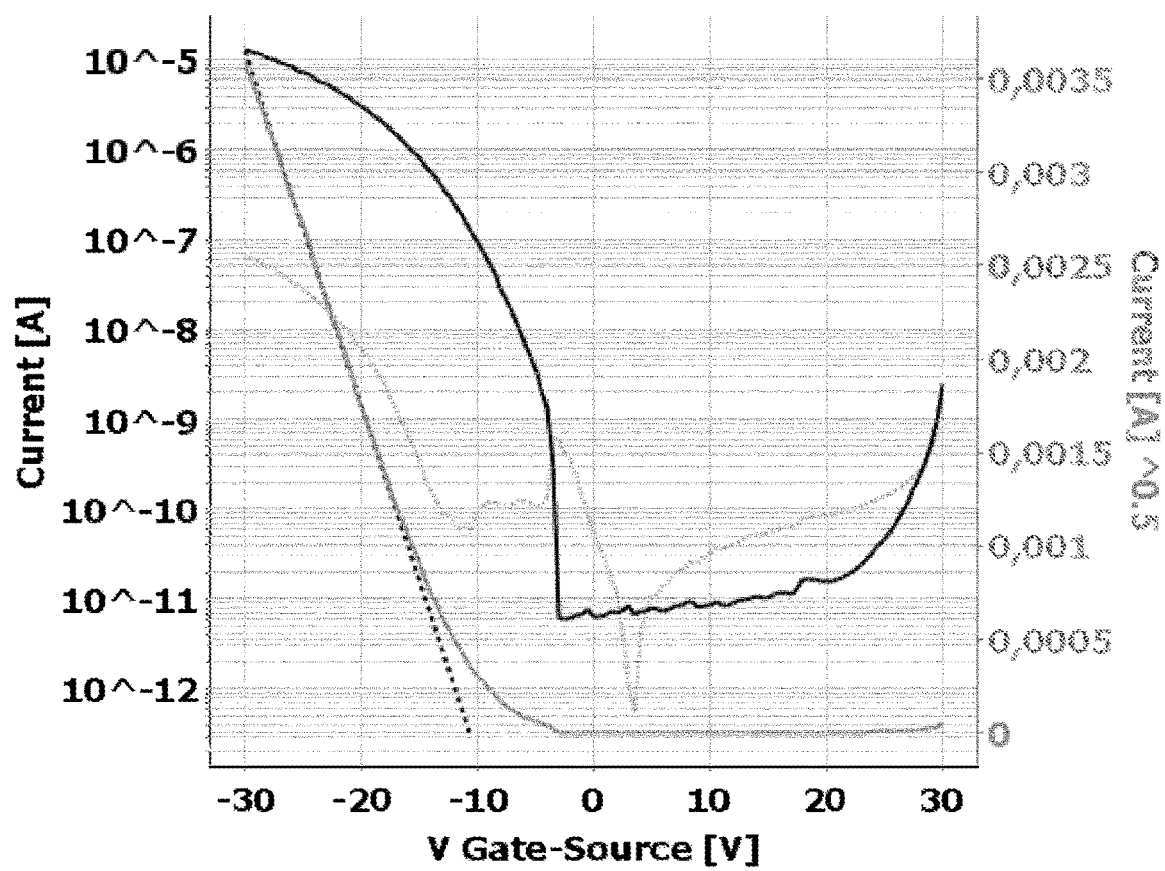
FIG. 3 show representative transfer characteristics of an FET fabricated from polymer P-3 with $V_{GS}$=30 V to −30 V at 0.5 V step size with $V_{DS}$=−30 V. Drain current (black solid curve), Gate current (dotted grey curve), Square root of drain current (grey solid curve), and fitted slope of square root (dashed black curve).
Figure 4:
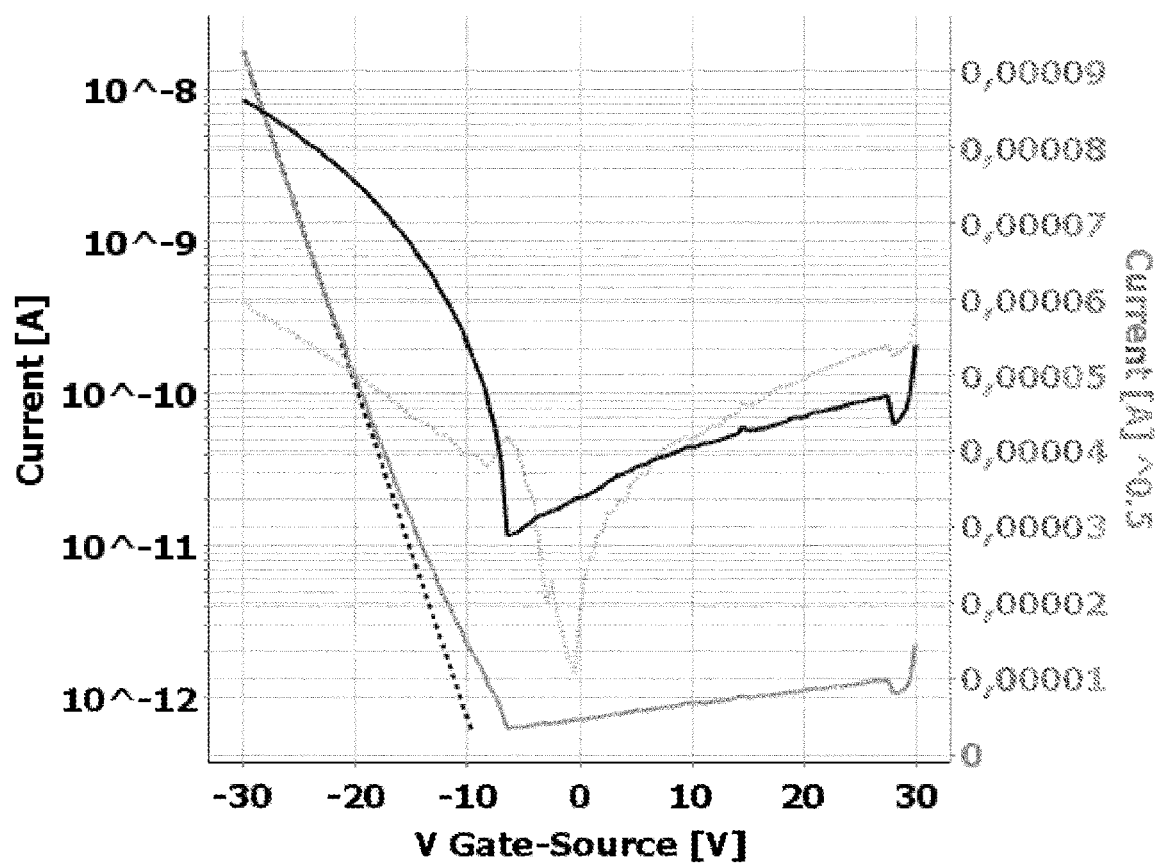
FIG. 4 show representative transfer characteristics of an FET fabricated from polymer P-4 with $V_{GS}$=30 V to −30 V at 0.5 V step size with $V_{DS}$=−30 V. Drain current (black solid curve), Gate current (dotted grey curve), Square root of drain current (grey solid curve), and fitted slope of square root (dashed black curve).

The following mobilities, threshold voltages and ON/OFF ratios are the average values obtained for the respective compound. The number of TFTs entering the calculation of the average is given in the table:

| Compound | Number of TFTs | Field-effect mobility µ [cm²/Vs] | Threshold voltage $U_{TH}$ [V] | ON/OFF ratio |
|---|---|---|---|---|
| P-1 | 20 | 2.0 | −11 | 4E6 |
| P-2 | 19 | 1.4 | −8.5 | 4E6 |
| P-3 | 18 | 1.4 | −10.7 | 2E6 |
| P-4 | 13 | 7E-4 | −8.9 | 8E2 |

The invention claimed is:

1. A polymer suitable as a semiconducting material, comprising a unit of formulae (1c):

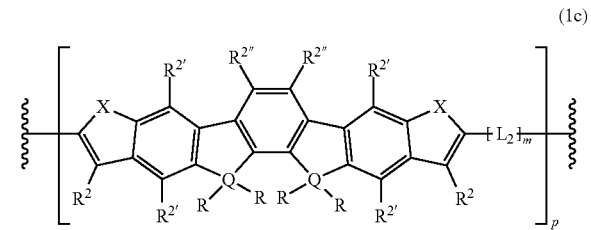

wherein:
X is S;
Q is C;
$L^2$ is selected from the group consisting of $C_{6-30}$-arylene, 5 to 30 membered heteroarylene,

$C_{6-30}$-arylene and 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)-R^{31}$, $C(O)-OR^{31}$, $C(O)-R^{31}$, $NR^{31}R^{32}$, $NR^{31}-C(O)R^{32}$, $C(O)-NR^{31}R^{32}$, $N[C(O)R^{31}][C(O)R^{32}]$, $SR^{31}$, halogen, CN, $SiR^{Siv}R^{Siw}R^{Six}$ and OH,

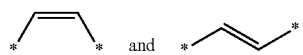

can be substituted with one or two substituents $R^4$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)$—$R^{41}$, $C(O)$—$NR^{41}R^{42}$, $C(O)$—$OR^{41}$ and CN, $R^{31}$, $R^{32}$, $R^{41}$ and $R^{42}$ are independently from each other and at each occurrence selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$; and at least two $CH_2$-groups, but not adjacent $CH_2$-groups of $C_{1-30}$-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl can be replaced by O, S, OC(O), CO, $NR^i$ or $NR^i$—CO, $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$, $R^{Siv}$, $R^{Siw}$, $R^{Six}$ are independently from each other selected from the group consisting of H, $C_{1-20}$-alkyl, $C_{2-20}$-alkenyl, $C_{2-20}$-alkynyl, $C_{5-6}$-cycloalkyl, phenyl and O—Si(CH$_3$)$_3$, $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-10}$-aryl, and 5 to 14 membered heteroaryl, $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $C_{6-14}$-aryl and 5 to 14 membered heteroaryl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $R^k$ and $R^l$ are independently selected from the group consisting of H, $C_{1-10}$-alkyl, $C_{2-10}$-alkenyl and $C_{2-10}$-alkynyl, $C_{1-10}$-alkyl, $C_{2-10}$-alkenyl and $C_{2-10}$-alkynyl can be substituted with one to five substituents selected from the group consisting of halogen, CN and $NO_2$, $R^2$, $R^{2'}$ and $R^{2''}$ are each occurrence selected from the group consisting of hydrogen, unsubstituted $C_{1-30}$-alkyl and halogen, R is at each occurrence unsubstituted $C_{1-50}$-alkyl, $C_{3-50}$-alkenyl, or $C_{3-50}$-alkynyl, m is 0, 1, 2, 3 or 4, and p is 2 to 1000.

2. The polymer according to claim 1, wherein:

$R^2$, $R^{2'}$ and $R^{2''}$ are at each occurrence hydrogen, and R is at each occurrence $C_{1-36}$-alkyl.

3. The polymer of claim 1, wherein:

$L^2$ is selected from the group from the group consisting of $C_{6-30}$-arylene and 5 to 30 membered heteroarylene, and

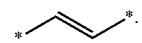

$C_{6-30}$-arylene and 5 to 30 membered heteroarylene can be substituted with one to six substituents $R^3$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $OR^{31}$, $OC(O)$—$R^{31}$, $C(O)$—$OR^{31}$, $C(O)$—$R^{31}$, $NR^{31}R^{32}$, $NR^{31}$—$C(O)R^{32}$, $C(O)$—$NR^{31}R^{32}$, $SR^{31}$, halogen, CN, $SiR^{Siv}R^{Siw}R^{Six}$ and OH,

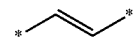

can be substituted with one or two substituents $R^4$ at each occurrence selected from the group consisting of $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C(O)$—$R^{41}$, $C(O)$—$NR^{41}R^{42}$, $C(O)$—$OR^{41}$ and CN, $R^{31}$, $R^{32}$, $R^{41}$ and $R^{42}$ are independently from each other and at each occurrence selected from the group consisting of H, $C_{1-30}$-alkyl, $C_{2-30}$-alkenyl, $C_{2-30}$-alkynyl, $C_{5-12}$-cycloalkyl, $C_{6-18}$-aryl and 5 to 20 membered heteroaryl, $C_{1-30}$-alkyl, $C_{2-30}$-alkenyl and $C_{2-30}$-alkynyl can be substituted with one to ten substituents independently selected from the group consisting of $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R][C(O)R^i]$, $SR^i$, halogen, CN, $SiR^{Siv}R^{Siw}R^{Six}$ and $NO_2$; and at least two $CH_2$-groups, but not adjacent $CH_2$-groups of $C_{1-30}$n-alkyl, $C_{2-30}$-alkenyl and $C_{2-30}$-alkynyl can be replaced by O or S, $C_{5-12}$-cycloalkyl can be substituted with one to six substituents independently selected from the group consisting of $C_{1-20}$-alkyl, $C_{2-20}$-alkenyl and $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R^i][C(O)R^j]$, $SR^i$, halogen, CN, $SiR^{Siv}R^{Siw}R^{Six}$ and $NO_2$; and one or two $CH_2$-groups, but not adjacent $CH_2$-groups, of $C_{5-12}$-cycloalkyl can be replaced by O, S, OC(O), CO, $NR^i$ or $NR^i$—CO, $C_{6-18}$-aryl and 5 to 20 membered heteroaryl can be substituted with one to six substituents independently selected from the group consisting of $C_{1-20}$-alkyl, $C_{2-20}$-alkenyl, $C_{2-20}$-alkynyl, $C_{5-8}$-cycloalkyl, $C_{6-14}$-aryl, 5 to 14 membered heteroaryl, $OR^i$, $OC(O)$—$R^j$, $C(O)$—$OR^i$, $C(O)$—$R^i$, $NR^iR^j$, $NR^i$—$C(O)R^j$, $C(O)$—$NR^iR^j$, $N[C(O)R][C(O)R^j]$, $SR^i$, halogen, CN, $SiR^{Siv}R^{Siw}R^{Six}$ and $NO_2$, $R^{Siv}$, $R^{Siw}$, $R^{Six}$ are independently from each other selected from the group consisting of H, $C_{1-20}$-alkyl, $C_{2-20}$-alkenyl, $C_{2-20}$-alkynyl, $C_{5-8}$-cycloalkyl, phenyl and O—$Si(CH_3)_3$, $R^i$ and $R^j$ are independently selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^k$, $OC(O)$—$R^l$, $C(O)$—$OR^k$, $C(O)$—$R^k$, $NR^kR^l$, $NR^k$—$C(O)R^l$, $C(O)$—$NR^kR^l$, $N[C(O)R^k][C(O)R^l]$, $SR^k$, halogen, CN, and $NO_2$, $R^k$ and $R^l$ are independently selected from the group consisting of H, $C_{1-10}$-alkyl, $C_{2-10}$-alkenyl and $C_{2-10}$-alkynyl, and $C_{1-10}$-alkyl, $C_{2-10}$-alkenyl and $C_{2-10}$-alkynyl can be substituted with one to five substituents selected from the group consisting of halogen, CN and $NO_2$.

4. The polymer of claim 3, wherein:

$L^2$ is selected from the group from the group consisting of $C_{6-30}$-arylene and 5 to 30 membered heteroarylene, and

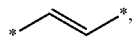

$C_{6-30}$-arylene and 5 to 30 membered heteroarylene is selected from the group consisting of

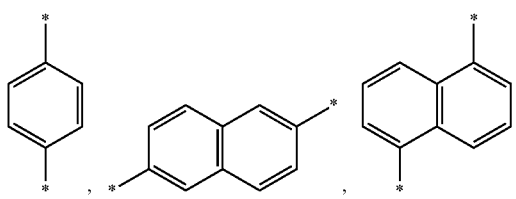

-continued

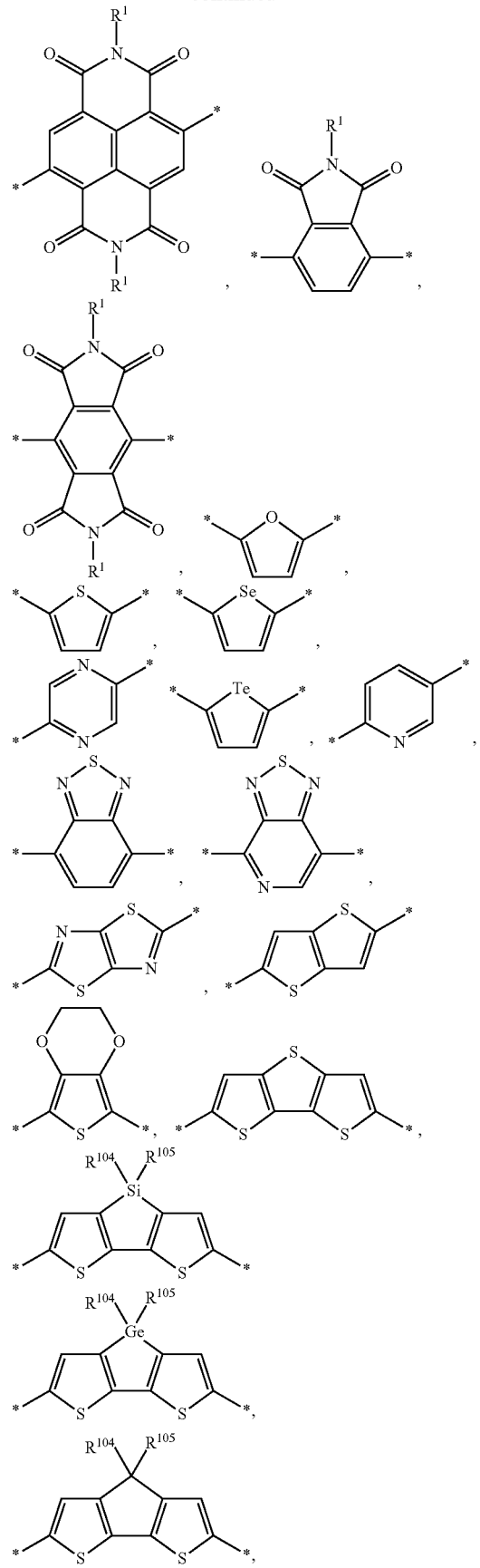

-continued

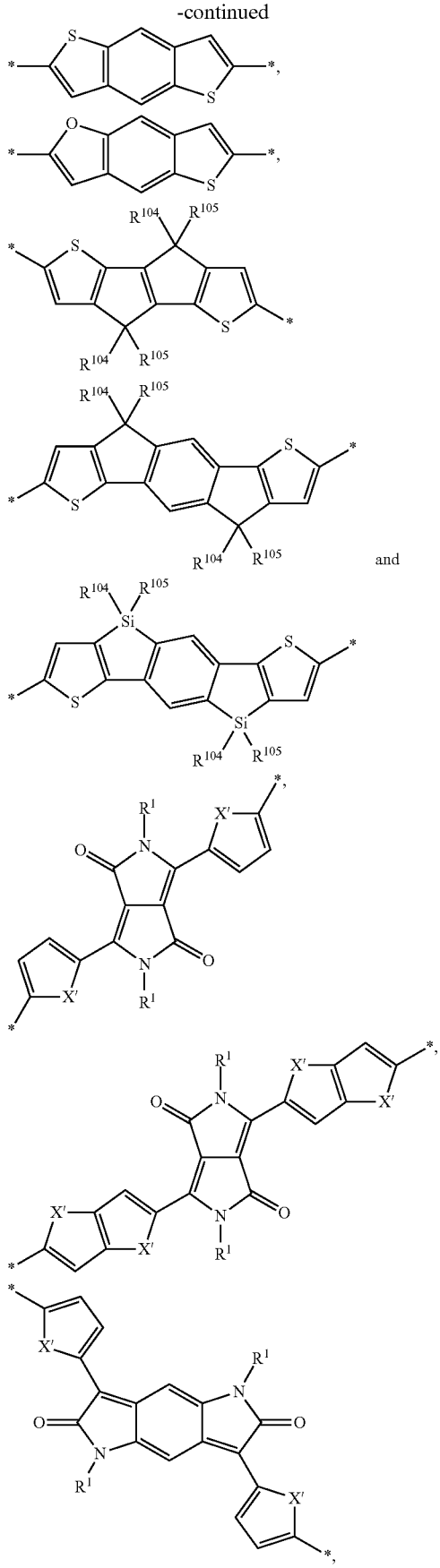

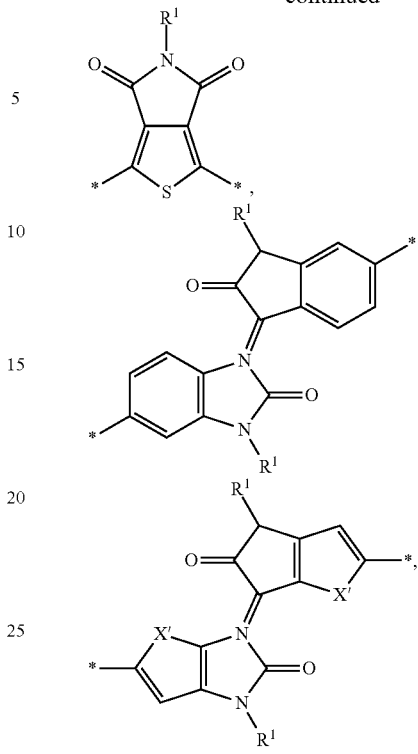

$R^{104}$ and $R^{105}$ are independently and at each occurrence selected from the group consisting of H, $C_{1-20}$-alkyl, $C_{2-20}$-alkenyl, $C_{2-20}$-alkynyl, $C_{5-8}$-cycloalkyl, $C_{6-14}$-aryl, and 5 to 14 membered heteroaryl, or $R^{104}$ and $R^{105}$, if attached to the same atom, together with the atom, to which they are attached, form a 5 to 12 membered ring system, $C_{1-20}$-alkyl, $C_{2-20}$-alkenyl and $C_{2-20}$-alkynyl can be substituted with one to five substituents selected from the group consisting of $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, $C_{5-8}$-cycloalkyl can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, $C_{6-14}$-aryl and 5 to 14 membered heteroaryl can be substituted with one to five substituents independently selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, 5 to 12 membered ring system can be substituted with one to five substituents selected from the group consisting of $C_{1-10}$-alkyl, $C_{2-10}$-alkenyl, $C_{2-10}$-alkynyl, $C_{5-6}$-cycloalkyl, $C_{6-10}$-aryl, 5 to 10 membered heteroaryl, $OR^s$, $OC(O)$—$R^t$, $C(O)$—$OR^s$, $C(O)$—$R^s$, $NR^sR^t$, $NR^s$—$C(O)R^t$, $C(O)$—$NR^sR^t$, $N[C(O)R^s][C(O)R^t]$, $SR^s$, halogen, CN, and $NO_2$, $R^s$ and $R^t$ are independently selected from the group consisting of H, $C_{1-10}$-alkyl, $C_{2-10}$-alkenyl and $C_{2-10}$-alkynyl, $C_{1-10}$-alkyl, $C_{2-10}$-alkenyl and $C_{2-10}$-alkynyl can be substituted with one to five substituents selected from the group consisting of halogen, CN and $NO_2$, $C_{6-30}$-arylene and 5 to 30 membered heteroarylene can be substituted with one to six substituents $R^3$ at each occurrence selected from the group consisting of $C_{1-30}$-alkyl and halogen,

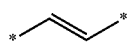

can be substituted with one or two substituents $R^4$ at each occurrence selected from the group consisting of $C_{1-30}$-alkyl, C(O)—$R^{41}$, C(O)—$OR^{41}$ and CN, $R^{41}$ is at each occurrence $C_{1-30}$-alkyl, and X' is S.

5. The polymer of claim 4, wherein: $L^2$ is selected from the group consisting of

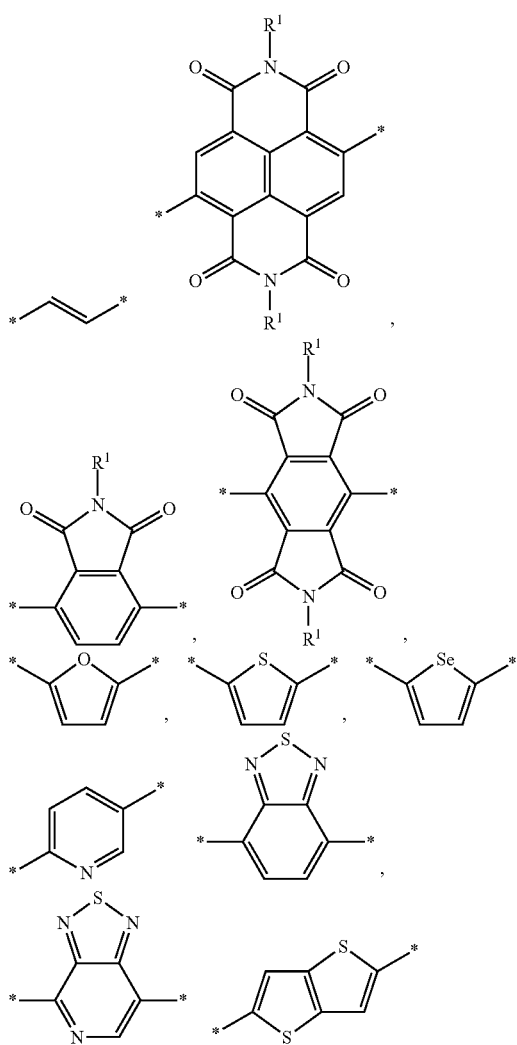

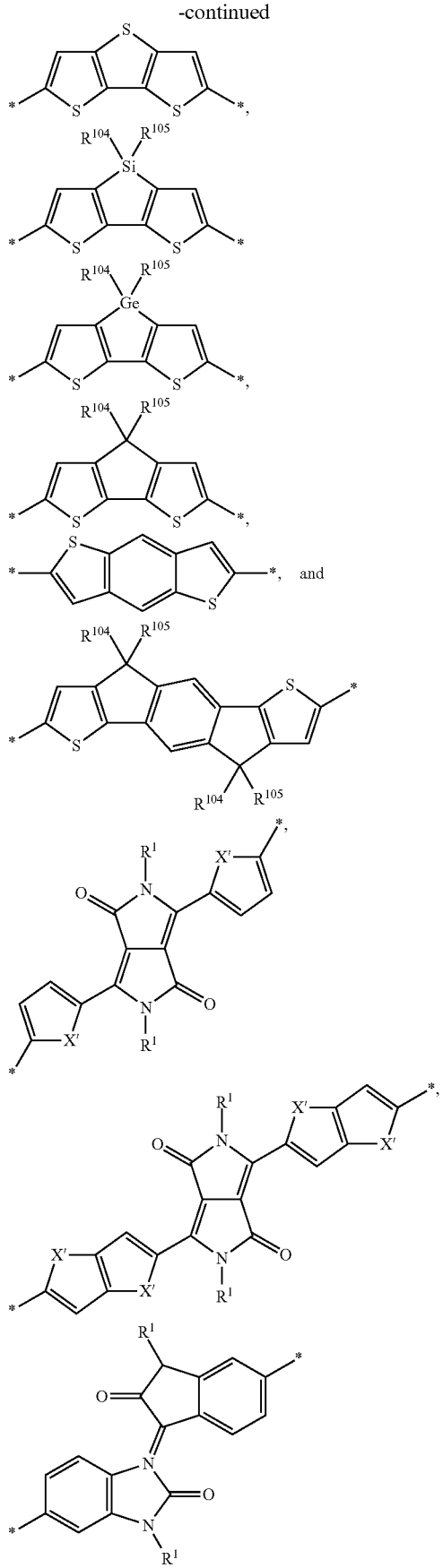

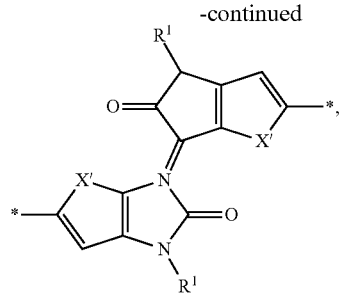
and
X' is S.
6. The polymer of claim 5, wherein: L² is selected from the group consisting of
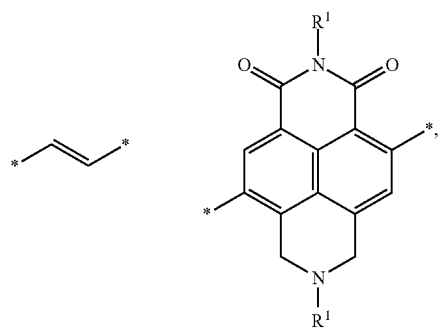
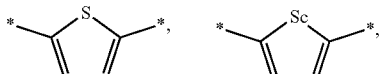
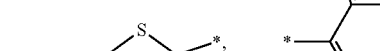
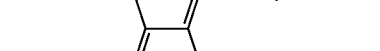
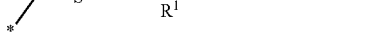
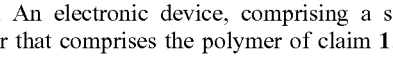
7. The polymer of claim 1, wherein m is 0, 1 or 2.
8. An electronic device, comprising a semiconducting layer that comprises the polymer of claim 1.
* * * * *